US010786380B2

(12) United States Patent
Baker et al.

(10) Patent No.: US 10,786,380 B2
(45) Date of Patent: Sep. 29, 2020

(54) BARIATRIC DEVICE AND METHOD

(71) Applicant: BFKW, LLC, Grand Rapids, MI (US)

(72) Inventors: Randal S. Baker, Ada, MI (US);
James A. Foote, Ada, MI (US); Paul R. Kemmeter, Ada, MI (US);
Frederick J. Walburn, Grand Rapids, MI (US); Peter M. Wilson,
Killingworth, CT (US); Adam I. Lehman, Northford, CT (US); Barry J. Smith, Kennett Square, PA (US);
Robert J. Chappolini, Phoenix, MD (US)

(73) Assignee: BFKW, LLC, Ada, MI (US)

( * ) Notice: Subject to any disclaimer, the term of this patent is extended or adjusted under 35 U.S.C. 154(b) by 175 days.

(21) Appl. No.: 15/844,111

(22) Filed: Dec. 15, 2017

(65) Prior Publication Data
US 2018/0104080 A1    Apr. 19, 2018

Related U.S. Application Data

(60) Continuation of application No. 13/965,617, filed on Aug. 13, 2013, now Pat. No. 9,872,787, which is a
(Continued)

(51) Int. Cl.
*A61F 5/00*    (2006.01)
*A61B 17/00*    (2006.01)
(Continued)

(52) U.S. Cl.
CPC ...... *A61F 5/0079* (2013.01); *A61B 17/00234* (2013.01); *A61B 17/0401* (2013.01);
(Continued)

(58) Field of Classification Search
CPC ........ A61F 5/0076–0079; A61F 5/0003–0086; A61B 2017/00818
See application file for complete search history.

(56) References Cited

U.S. PATENT DOCUMENTS 4,403,604 A    9/1983    Wilkinson et al.
4,607,618 A    8/1986    Angelchik
(Continued)

FOREIGN PATENT DOCUMENTS

EP    0760696 B1    8/2001
EP    1808888 A2    7/2007
(Continued)

OTHER PUBLICATIONS

Dixon et al. "Health Outcomes of Severely Obese Type 2 Diabetic Subjects 1 Year After Laparoscopic Adjustable Gastric Banding". 2002. Diabetic Care 25:358-363. (Year 2002).
(Continued)

*Primary Examiner* — Thaddeus B Cox
(74) *Attorney, Agent, or Firm* — Gardner, Linn, Burkhart & Ondersma LLP

(57)    ABSTRACT

A bariatric device includes an esophageal member having an esophageal surface that is configured to generally conform to the shape and size of a portion of the esophagus and an anchoring technique anchoring the esophageal member to the portion of the esophagus. The bariatric device includes a cardiac member having a cardiac surface that is configured to generally conform to the shape and size of a portion of the cardiac portion of the stomach and a connector connected with the esophageal member and the cardiac member to cause strain to be applied by the cardiac member to the cardiac portion of the stomach. The strain applied by the cardiac member to the cardiac portion of the stomach causes satiety in the absence of food. The connector is adapted to pass through the gastroesophageal junction while leaving a
(Continued)

continuous portion of the gastroesophageal junction substantially unrestrained.

23 Claims, 73 Drawing Sheets

Related U.S. Application Data division of application No. 12/539,112, filed on Aug. 11, 2009, now Pat. No. 8,529,431, which is a continuation-in-part of application No. PCT/US2008/053912, filed on Feb. 14, 2008.

(60) Provisional application No. 61/159,143, filed on Mar. 11, 2009, provisional application No. 61/107,511, filed on Oct. 22, 2008, provisional application No. 60/931,109, filed on May 21, 2007, provisional application No. 60/921,930, filed on Apr. 5, 2007, provisional application No. 60/901,457, filed on Feb. 14, 2007.

(51) Int. Cl.
*A61F 2/04* (2013.01)
*A61B 17/04* (2006.01)
*A61B 17/064* (2006.01)

(52) U.S. Cl.
CPC ........ *A61B 17/0469* (2013.01); *A61B 17/064* (2013.01); *A61B 17/0643* (2013.01); *A61F 2/04* (2013.01); *A61F 5/0076* (2013.01); *A61F 5/0083* (2013.01); *A61B 2017/00818* (2013.01); *A61B 2017/0404* (2013.01); *A61B 2017/0464* (2013.01); *A61B 2017/0647* (2013.01); *A61B 2017/0649* (2013.01); *A61F 2002/045* (2013.01)

(56) References Cited

U.S. PATENT DOCUMENTS

| | | |
|---|---|---|
| 5,234,454 A | 8/1993 | Bangs |
| 5,306,300 A | 4/1994 | Berry |
| 5,366,504 A | 11/1994 | Andersen et al. |
| 5,507,755 A | 4/1996 | Gresl et al. |
| 5,662,713 A | 9/1997 | Andersen et al. |
| 5,741,279 A | 4/1998 | Gordon et al. |
| 5,820,584 A | 10/1998 | Crabb |
| 6,146,416 A | 11/2000 | Andersen et al. |
| 6,264,700 B1 | 7/2001 | Kilcoyne et al. |
| 6,280,415 B1 | 8/2001 | Johnson |
| 6,312,437 B1 | 11/2001 | Kortenbach |
| 6,355,070 B1 | 3/2002 | Andersen et al. |
| 6,398,802 B1 | 6/2002 | Yee |
| 6,432,040 B1 | 8/2002 | Meah |
| 6,447,533 B1 | 9/2002 | Adams |
| 6,544,291 B2 | 4/2003 | Taylor |
| 6,558,400 B2 | 5/2003 | Deem et al. |
| 6,572,627 B2 | 6/2003 | Gabbay |
| 6,656,194 B1 | 12/2003 | Gannoe et al. |
| 6,675,809 B2 | 1/2004 | Stack et al. |
| 6,736,828 B1 | 5/2004 | Adams et al. |
| 6,740,121 B2 | 5/2004 | Geitz |
| 6,746,460 B2 | 6/2004 | Gannoe et al. |
| 6,755,869 B2 | 6/2004 | Geitz |
| 6,773,440 B2 | 8/2004 | Gannoe et al. |
| 6,800,081 B2 | 10/2004 | Parodi |
| 6,802,868 B2 | 10/2004 | Silverman et al. |
| 6,845,776 B2 | 1/2005 | Stack et al. |
| 6,916,332 B2 | 7/2005 | Adams |
| 6,960,233 B1 | 11/2005 | Berg et al. |
| 6,981,978 B2 | 1/2006 | Gannoe |
| 6,994,095 B2 | 2/2006 | Burnett |
| 6,994,715 B2 | 2/2006 | Gannoe et al. |
| 7,025,791 B2 | 4/2006 | Levine et al. |
| 7,033,373 B2 | 4/2006 | de la Torre et al. |
| 7,033,384 B2 | 4/2006 | Gannoe et al. |
| 7,037,344 B2 | 5/2006 | Kagan et al. |
| 7,044,979 B2 | 5/2006 | Silverman et al. |
| 7,066,945 B2 | 6/2006 | Hashiba et al. |
| 7,083,629 B2 | 8/2006 | Weller et al. |
| 7,083,630 B2 | 8/2006 | DeVries et al. |
| 7,087,088 B2 | 8/2006 | Berg et al. |
| 7,097,650 B2 | 8/2006 | Weller et al. |
| 7,097,665 B2 | 8/2006 | Stack et al. |
| 7,111,627 B2 | 9/2006 | Stack et al. |
| 7,146,984 B2 | 12/2006 | Stack et al. |
| 7,152,607 B2 | 12/2006 | Stack et al. |
| 7,211,114 B2 | 5/2007 | Bessler et al. |
| 7,220,284 B2 | 5/2007 | Kagan et al. |
| 7,232,461 B2 | 6/2007 | Ramer |
| 7,347,875 B2 | 3/2008 | Levine et al. |
| 7,431,725 B2 | 10/2008 | Stack et al. |
| 7,445,010 B2 | 11/2008 | Kugler et al. |
| 7,449,024 B2 | 11/2008 | Stafford |
| 7,682,330 B2 | 3/2010 | Meade et al. |
| 7,704,264 B2 | 4/2010 | Ewers et al. |
| 7,708,752 B2 | 5/2010 | Durgin |
| 7,753,870 B2 | 7/2010 | Demarais et al. |
| 7,771,382 B2 | 8/2010 | Levine et al. |
| 7,794,447 B2 | 9/2010 | Dann et al. |
| 7,815,589 B2 | 10/2010 | Meade et al. |
| 7,815,591 B2 | 10/2010 | Levine et al. |
| 7,846,174 B2 | 12/2010 | Baker et al. |
| 7,922,650 B2 | 4/2011 | McWeeney et al. |
| 7,976,488 B2 | 7/2011 | Levine et al. |
| 7,981,163 B2 | 7/2011 | Meade et al. |
| 8,029,455 B2 | 10/2011 | Stack et al. |
| 8,043,355 B2 | 10/2011 | Shin et al. |
| 8,100,931 B2 | 1/2012 | Baker et al. |
| 8,137,301 B2 | 3/2012 | Levine et al. |
| 8,162,871 B2 | 4/2012 | Levine et al. |
| 8,282,598 B2 | 10/2012 | Belhe et al. |
| 8,372,087 B2 | 2/2013 | Baker et al. |
| 8,447,403 B2 | 5/2013 | Sharma et al. |
| 8,506,477 B2 | 8/2013 | Waller et al. |
| 8,529,431 B2 | 9/2013 | Baker et al. |
| 8,672,831 B2 | 3/2014 | Baker et al. |
| 8,721,528 B2 | 5/2014 | Ho et al. |
| 8,778,011 B2 | 7/2014 | Ryan |
| 8,784,436 B2 | 7/2014 | Ho et al. |
| 8,801,599 B2 | 8/2014 | Baker et al. |
| 8,894,670 B2 | 11/2014 | Baker et al. |
| 9,055,998 B2 | 6/2015 | Baker |
| 9,060,844 B2 | 6/2015 | Kagan et al. |
| 9,198,789 B2 | 12/2015 | Baker et al. |
| 9,375,338 B2 | 6/2016 | Baker et al. |
| 9,414,948 B2 | 8/2016 | Baker et al. |
| 9,545,326 B2 | 1/2017 | Baker et al. |
| 9,839,545 B2 | 12/2017 | Baker et al. |
| 9,872,787 B2 | 1/2018 | Baker et al. |
| 10,182,901 B2 | 1/2019 | Baker et al. |
| 10,271,940 B2 | 4/2019 | Baker et al. |
| 2001/0011543 A1 | 8/2001 | Forsell |
| 2001/0020189 A1 | 9/2001 | Taylor |
| 2002/0032487 A1 | 3/2002 | Dua et al. |
| 2002/0091395 A1 | 7/2002 | Gabbay |
| 2003/0040804 A1 | 2/2003 | Stack et al. |
| 2003/0040808 A1 | 2/2003 | Stack et al. |
| 2003/0065359 A1 | 4/2003 | Weller et al. |
| 2003/0109935 A1 | 6/2003 | Geitz |
| 2003/0199989 A1 | 10/2003 | Stack et al. |
| 2003/0212450 A1 | 11/2003 | Schlick |
| 2004/0044357 A1 | 3/2004 | Gannoe et al. |
| 2004/0087976 A1 | 5/2004 | DeVries et al. |
| 2004/0092892 A1 | 5/2004 | Kagan et al. |
| 2004/0106987 A1 | 6/2004 | Palasis et al. |
| 2004/0116999 A1 | 6/2004 | Ledergerber |
| 2004/0117031 A1 | 6/2004 | Stack et al. |
| 2004/0122456 A1* | 6/2004 | Saadat ............ A61B 17/00234 606/157 |
| 2004/0138761 A1 | 7/2004 | Stack et al. |
| 2004/0143342 A1 | 7/2004 | Stack et al. |

(56) References Cited

U.S. PATENT DOCUMENTS

| | | |
|---|---|---|
| 2004/0148034 A1 | 7/2004 | Kagan et al. |
| 2004/0153167 A1* | 8/2004 | Stack .................. A61F 5/0089 623/23.65 |
| 2004/0167583 A1* | 8/2004 | Knudson ................ A61N 1/05 607/40 |
| 2004/0172141 A1 | 9/2004 | Stack et al. |
| 2004/0210111 A1 | 10/2004 | Okada |
| 2004/0220682 A1 | 11/2004 | Levine et al. |
| 2005/0004582 A1 | 1/2005 | Edoga et al. |
| 2005/0043683 A1 | 2/2005 | Ravo |
| 2005/0080395 A1 | 4/2005 | Levine et al. |
| 2005/0096728 A1 | 5/2005 | Ramer |
| 2005/0125020 A1 | 6/2005 | Meade et al. |
| 2005/0177181 A1* | 8/2005 | Kagan ............. A61B 17/00234 606/151 |
| 2005/0192629 A1 | 9/2005 | Saadat et al. |
| 2005/0197715 A1 | 9/2005 | Kugler et al. |
| 2005/0228504 A1 | 10/2005 | Demarais |
| 2005/0245788 A1 | 11/2005 | Gerber |
| 2005/0245957 A1 | 11/2005 | Starkebaum et al. |
| 2005/0247320 A1 | 11/2005 | Stack et al. |
| 2005/0251165 A1 | 11/2005 | Vaughan et al. |
| 2005/0251176 A1 | 11/2005 | Swanstrom et al. |
| 2005/0283235 A1 | 12/2005 | Kugler et al. |
| 2006/0020277 A1 | 1/2006 | Gostout et al. |
| 2006/0036293 A1 | 2/2006 | Whitehurst et al. |
| 2006/0064120 A1 | 3/2006 | Levine et al. |
| 2006/0074473 A1 | 4/2006 | Gertner |
| 2006/0089571 A1 | 4/2006 | Gertner |
| 2006/0142844 A1 | 6/2006 | Lowe et al. |
| 2006/0149307 A1 | 7/2006 | Durgin |
| 2006/0151568 A1* | 7/2006 | Weller ............... A61B 17/0218 227/175.1 |
| 2006/0155375 A1 | 7/2006 | Kagan et al. |
| 2006/0161139 A1 | 7/2006 | Levine et al. |
| 2006/0190019 A1 | 8/2006 | Gannoe et al. |
| 2006/0247721 A1 | 11/2006 | Maschino et al. |
| 2006/0253131 A1 | 11/2006 | Wolniewicz, III |
| 2006/0253142 A1 | 11/2006 | Bjerken |
| 2006/0264699 A1 | 11/2006 | Gertner |
| 2006/0265082 A1 | 11/2006 | Meade et al. |
| 2007/0005147 A1 | 1/2007 | Levine et al. |
| 2007/0010866 A1 | 1/2007 | Dann et al. |
| 2007/0088428 A1 | 4/2007 | Teichman |
| 2007/0112409 A1 | 5/2007 | Wu et al. |
| 2007/0123994 A1 | 5/2007 | Ortiz et al. |
| 2007/0166396 A1 | 7/2007 | Badylak et al. |
| 2007/0179590 A1 | 8/2007 | Lu et al. |
| 2007/0198035 A1 | 8/2007 | Threlkeld |
| 2007/0208429 A1 | 9/2007 | Leahy |
| 2007/0233221 A1 | 10/2007 | Raju |
| 2007/0260112 A1 | 11/2007 | Rahmani |
| 2007/0270742 A1* | 11/2007 | Guetty ................ A61F 5/0003 604/103.05 |
| 2007/0276432 A1 | 11/2007 | Stack et al. |
| 2007/0293716 A1 | 12/2007 | Baker et al. |
| 2008/0015523 A1 | 1/2008 | Baker |
| 2008/0015618 A1 | 1/2008 | Sonnenschein et al. |
| 2008/0015633 A1 | 1/2008 | Abbott et al. |
| 2008/0065122 A1 | 3/2008 | Stack et al. |
| 2008/0065136 A1 | 3/2008 | Young |
| 2008/0215076 A1 | 9/2008 | Baker |
| 2008/0312678 A1 | 12/2008 | Pasricha |
| 2009/0138071 A1 | 5/2009 | Cheng et al. |
| 2009/0177215 A1 | 7/2009 | Stack et al. |
| 2009/0187230 A1 | 7/2009 | Dilorenzo |
| 2009/0240340 A1 | 9/2009 | Levine et al. |
| 2009/0248171 A1 | 10/2009 | Levine et al. |
| 2009/0270818 A1 | 10/2009 | Duke |
| 2010/0010298 A1 | 1/2010 | Bakos et al. |
| 2010/0030017 A1 | 2/2010 | Baker et al. |
| 2010/0063518 A1 | 3/2010 | Baker et al. |
| 2010/0114124 A1 | 5/2010 | Kelleher et al. |
| 2010/0114130 A1 | 5/2010 | Meade et al. |
| 2010/0198237 A1 | 8/2010 | Baker et al. |
| 2010/0256775 A1 | 10/2010 | Belhe et al. |
| 2010/0280313 A1 | 11/2010 | Gasche et al. |
| 2011/0004146 A1 | 1/2011 | Priplata et al. |
| 2011/0009690 A1 | 1/2011 | Belhe et al. |
| 2011/0092879 A1 | 4/2011 | Baker et al. |
| 2011/0264234 A1 | 10/2011 | Baker et al. |
| 2012/0083871 A1 | 4/2012 | Ryan |
| 2012/0089168 A1 | 4/2012 | Baker et al. |
| 2012/0095497 A1 | 4/2012 | Babkes et al. |
| 2012/0191213 A1 | 7/2012 | Baker et al. |
| 2012/0191215 A1 | 7/2012 | Baker et al. |
| 2012/0203061 A1 | 8/2012 | Birk |
| 2012/0289991 A1 | 11/2012 | Baker |
| 2013/0123811 A1 | 5/2013 | Baker et al. |
| 2013/0296913 A1 | 11/2013 | Foote et al. |
| 2013/0324902 A1 | 12/2013 | Miller et al. |
| 2014/0018611 A1 | 1/2014 | Baker et al. |
| 2014/0114230 A1 | 4/2014 | Baker et al. |
| 2014/0121585 A1 | 5/2014 | Baker et al. |
| 2014/0309681 A1 | 10/2014 | Baker et al. |
| 2015/0025313 A1 | 1/2015 | Baker et al. |
| 2015/0039092 A1 | 2/2015 | Baker et al. |
| 2015/0182239 A1 | 7/2015 | Baker et al. |
| 2016/0038325 A1 | 2/2016 | Baker et al. |
| 2016/0151233 A1 | 6/2016 | Baker et al. |
| 2016/0262867 A1 | 9/2016 | Baker et al. |
| 2016/0324671 A1 | 11/2016 | Baker et al. |
| 2017/0172723 A1 | 6/2017 | Foote et al. |

FOREIGN PATENT DOCUMENTS

| | | |
|---|---|---|
| EP | 2240215 B1 | 1/2014 |
| JP | 2660101 | 6/1997 |
| JP | 2006-103873 A | 4/2006 |
| JP | 2007508053 A | 4/2007 |
| JP | 2011509758 A | 3/2011 |
| RU | 2045233 C1 | 10/1995 |
| RU | 94026119 A | 8/1996 |
| RU | 2386455 | 4/2010 |
| WO | WO 93/22986 | 11/1993 |
| WO | WO 94/12136 | 6/1994 |
| WO | WO 01/35834 A1 | 5/2001 |
| WO | WO 01/85034 A1 | 11/2001 |
| WO | WO 02/060328 A1 | 8/2002 |
| WO | WO 02/094105 A2 | 11/2002 |
| WO | WO 2004/019826 A1 | 3/2004 |
| WO | WO 2004/064680 A1 | 8/2004 |
| WO | WO 2004/064685 | 8/2004 |
| WO | WO 2005/037152 A1 | 4/2005 |
| WO | WO 2006/044640 A1 | 4/2006 |
| WO | WO 2006/078672 A1 | 7/2006 |
| WO | WO 2007/092390 A2 | 8/2007 |
| WO | WO 2008/100984 A2 | 8/2008 |
| WO | WO 2008/101048 A2 | 8/2008 |
| WO | WO 2008/101078 A2 | 8/2008 |
| WO | WO 2009/048398 A1 | 4/2009 |
| WO | WO 2009/091899 A2 | 7/2009 |
| WO | 2010117641 | 10/2010 |
| WO | WO 2011/056608 A1 | 5/2011 |
| WO | WO 2011/063307 A1 | 5/2011 |
| WO | WO 2011/097209 A1 | 8/2011 |
| WO | WO 2011/116025 A1 | 9/2011 |
| WO | WO 2012/044917 A1 | 4/2012 |
| WO | 2012136249 | 10/2012 |
| WO | WO 2012/162114 A1 | 11/2012 |
| WO | WO 2013/090190 A1 | 6/2013 |
| WO | WO 2013/134227 A1 | 9/2013 |
| WO | WO 2015/031077 A1 | 3/2015 |
| WO | WO 2016/109346 A1 | 7/2016 |

OTHER PUBLICATIONS

International Search Report of the International Searching Authority from corresponding Patent Cooperation Treaty (PCT) Patent Application No. PCT/US12/38480, dated Jul. 30, 2012.

(56) References Cited

OTHER PUBLICATIONS

International Preliminary Report on Patentability and Written Opinion of the International Searching Authority from corresponding Patent Cooperation Treaty (PCT) Patent Application No. PCT/US12/38480, dated Nov. 29, 2013.
"Obesity: Super-Sized Medical Device Market", Start-Up, Mar. 2003, Technology Strategies (Long Article), pp. 1-10 and a cover page.
Andrew S. Lowe, M.D. and Maria B. Sheridan, M.D., "Esphogeal Stenting", Seminars in Interventional Radiology, vol. 21, No. 3, 2004, pp. 157-166.
"Polyflex® Espohageal Stent", Silicone Covered Stent, Boston Scientific, three pages (2003).
Andrew F.R. Dixon, Johgn B. Dixon, and Paul E. O'Brien, "Laparoscopic Adjustable Gastric Banding Induces Prolonged Satiety: A Randomized Blind Crossover Study", The Journal of Clinical Endocrinology & Metabolism , pp. 813-819, 2005.
Roman, S. et al., "Intragastric balloon for 'non-morbid' obesity: a retrospective evaluation of tolerance and efficacy," Obes. Surg., 2004, 14(4), 539-44, abstract, [on-line], [found Apr. 17, 2009, from Pubmed database].
Busetto, L. et al., "Preoperative weight loss by intragastric balloon in super-obese patients treated with laparoscopic gastric banding: a case-control study," Obes Surg., 2004, 14(5), 671-6, abstract, [on-line], [found Apr. 17, 2009, from Pubmed database].

Summary of Official Action dated Oct. 29, 2009, from the Israel Patent Office in a patent application corresponding to the present application.
Lowe, Andrew S., M.D. and Sheridan, Maria B., M.D., "Esophageal Stenting," annotated by Israel Patent Office (2004).
Abstract and claims of U.S. Pat. No. 6,960,233 annotated by the Israel Patent Office (Nov. 1, 2005).
Schembre, Drew, "Advances in Esophageal Stenting: the Evolution of Fully Covered Stents for Malignant and Benign Disease," Adv. Ther., Springer Healthcare, Apr. 1, 2010, pp. 1-13.
International Preliminary Report on Patentability and Written Opinion of the International Searching Authority from corresponding Patent Cooperation Treaty (PCT) Patent Application No. PCT/US08/53912, dated Aug. 19, 2009.
International Preliminary Report on Patentability and Written Opinion of the International Searching Authority from corresponding Patent Cooperation Treaty (PCT) Patent Application No. PCT/US05/36991, dated Mar. 6, 2006.
S. Fukudo, T. Nomura, M. Hongo, "Impact of corticotropin-releasing hormone on gastrointestinal motility and adrenocorticotropic hormone in normal controls and patients with irritable bowel syndrome", Jan. 19, 1998.
D.G. Maxton, D.F. Martin, P.J. Whorwell, M. Godfrey. "Abdominal distension in female patients with irritable bowel syndrome: exploration of possible mechanisms", Aug. 3, 1990.

\* cited by examiner

BARIATRIC DEVICE AND METHOD

CROSS REFERENCE TO RELATED APPLICATIONS

The present application is a continuation of U.S. patent application Ser. No. 13/965,617, filed Aug. 13, 2013, which is division of U.S. patent application Ser. No. 12/539,112, filed Aug. 11, 2009, now U.S. Pat. No. 8,529,431, which claims priority from U.S. provisional patent application Ser. No. 61/107,511, filed on Oct. 22, 2008, and U.S. provisional patent application Ser. No. 61/159,143, filed on Mar. 11, 2009; and U.S. patent application Ser. No. 12/539,112, filed Aug. 11, 2009, is a continuation-in-part of International Patent Cooperation Treaty Application No. PCT/US08/53912, filed on Feb. 14, 2008, which claims priority from U.S. provisional patent application Ser. No. 60/901,457, filed on Feb. 14, 2007; U.S. provisional patent application Ser. No. 60/921,930, filed on Apr. 5, 2007; and U.S. provisional patent application Ser. No. 60/931,109, filed on May 21, 2007, the disclosures of which are hereby incorporated herein by reference in their entireties.

BACKGROUND OF THE INVENTION

The present invention is directed to a bariatric device and method of causing weight loss in a recipient.

Obesity is a large and increasing problem in the United States and worldwide. In round numbers, from the period encompassing the year 1990 to the period encompassing the year 2000, the prevalence of overweight people (BMI greater than 25) increased from 56 percent of United States adults to 65 percent and the prevalence of obese adults (BMI greater than 30) increased from 23 percent to 30 percent. Likewise, the prevalence of overweight children and adolescents (ages 6-19 years) increased from 11 percent in the period encompassing the year 1990 to 16 percent in the period encompassing the year 2000. The increasing prevalence of excess body mass among children and adolescents will make the problem even greater when they reach adulthood. The problem is not limited to the United States. Between 10 percent and 20 percent of European men are obese and between 10 percent and 25 percent of European women are obese. Numerous medical conditions are made worse by obesity including Type II diabetes, stroke, gallbladder disease and various forms of cancer. Approximately 500,000 people in North America and Western Europe are estimated to die from obesity-related diseases every year and obesity is estimated to affect more than one billion adults worldwide. Therefore, there is a pressing and unmet need for a solution to the epidemic problem.

SUMMARY OF THE INVENTION

The present invention provides a bariatric device and method of causing weight loss in a recipient that fulfills this pressing and unmet need in an effective and minimally invasive manner. A bariatric device and method of causing weight loss in a recipient according to an aspect of the invention includes providing an esophageal member, a cardiac member and a connector connected with the esophageal member and the cardiac member. The esophageal member has an esophageal surface that is configured to generally conform to the shape and size of a portion of the esophagus. The cardiac member has a cardiac surface that is configured to generally conform to the shape and size of a portion of the cardiac portion of the stomach. Receptors are stimulated in order to influence a neuro-hormonal mechanism in the recipient sufficient to cause weight loss including positioning the esophageal surface at the esophagus and the cardiac surface at the cardiac portion of the stomach. This causes at least partial satiety by augmenting fullness caused by food and simulating fullness in the absence of food.

The connector may be positioned at the GE junction and be adapted to leave a contiguous portion of the GE junction substantially unrestrained. This contiguous portion of the GE junction may be at least half of the GE junction, may be at least 75% of the GE junction and may be at least 90% of the GE junction. The contiguous portion of the GE junction may be at the angle of His.

The connector may include a tension member, such as a semi-rigid strap. The strap may be positioned within the GE junction opposite the angle of His. The strap may be made substantially of Nitinol.

The connector may include a tether. The tether may extend at least partially external the GE junction. The tether may be connected with the esophageal member and the cardiac member either in situ or external the recipient. The tether may be adjacent the angle of His. A clamp may be provided to secure at least one end of the tether. The clamp may include a body and a plurality of through-openings in the body, the through-openings receiving the tether and allowing one-way movement of the body along the tether. In this manner, the body may be movable in one direction along the tether and resists movement in an opposite direction.

The connector may include a plurality of the tethers. The tethers may be positioned either on a same side of the GE junction or on opposite sides of the GE junction. The tether(s) may be made from (i) substantially non-coated silk, (ii) Ethibond suture, (iii) ePTFE or (iv) an elastic material. The tether(s) may include a tissue attachment surface or a tissue ingrowth surface.

The esophageal member may have a reinforced tether attachment wall portion. The esophageal member may have an outer surface that defines a tissue attachment portion. The esophageal member may include a cage and an impervious cover over the cage. The cage may be formed from an elongated member that is joined at junctions by ferrules. The cage may be made up of an elongated member that is formed as an interwoven spiral. The cage may be covered with at least one flexible sleeve. The elongated member may be a Nitinol wire. Distal and/or proximal end portions of the cage may be flared.

The cardiac member may include a generally planar member defining the cardiac surface. The planar member may include a through-opening adapted to be positioned at the GE junction and a sealing flange surrounding the through-opening. The planar member may include a stiffening mesh and a generally flexible material surrounding the mesh. The planar member may include ribs that provide stiffening to the planar member or may include a surface feature to resist slippage of a deployment tool during tether driving. The cardiac member may be radiopaque in whole or in part.

The esophageal member, the cardiac member and the connector may be defined by an elongated member that is at least partially spirally wound. A surface cover may be provided over at least the esophageal member and the cardiac member. The connector may be defined by a portion of the elongated member that is not spirally wound.

The connector may be longitudinally adjustable. A ratchet mechanism may be provided to provide the longitudinal adjustability to the connector. The ratchet mechanism may be adjustable in situ.

The connector may include an adjustable tether. The adjustable tether may include a filament and a tube surrounding the filament to facilitate lengthwise movement of the filament.

The cardiac member may include a central portion and a surface extending from the central portion. The surface may be compressible toward itself for deployment and biased away from itself. The surface may be defined by lobes that are formed from elongated members.

The bariatric device may be deployed transorally. Manipulation lines may extend from the esophageal member and/or the cardiac member external the recipient to assist in deployment.

The bariatric device may be substantially non-restrictive to food passage.

The amount of stimulation to the receptors may be adjustable, such as by adjusting the connector and/or by selecting the bariatric device from among a plurality of bariatric devices of different sizes.

A unidirectional clamp and method of endoluminally restraining an end of a medical filament includes providing a body having at least three openings in body. An end portion of the filament is passed through two of the at least three openings to form a loop in the filament. A filament end is passed through another of the opening and under the loop.

A bariatric device and method of causing weight loss in a recipient, according to another aspect of the invention, includes providing at least one cardiac member that is configured to stimulate receptors at a portion of the cardiac region of the stomach. An anchor is provided to engage the cardiac region of the stomach to anchor the at least one cardiac member. In this manner, the cardiac member is capable of influencing a neurohormonal mechanism in the recipient.

The at least one cardiac member may define a cardiac surface and the anchor may hold the cardiac surface against the cardiac region of the stomach.

The anchor may be a plurality of anchors that are distributed about the cardiac region of the stomach with the at least one cardiac member applying a force between adjacent ones of the anchors. The at least one cardiac device may be an endless band that applies a contraction force to the plurality of anchors. Alternatively, the at least one cardiac device may be expansion devices, such as expansion springs, that apply an expansion force between adjacent ones of the anchors.

The anchor may include a surface that facilitates tissue attachment and/or tissue ingrowth.

The cardiac member may be configured to the size and shape of the cardiac region of a recipient with altered anatomy, such as a recipient who has undergone a gastric bypass procedure, a vertical banded gastroplasty, a sleeve gastrorectomy, a duodenal switch, or the like.

These and other objects, advantages and features of this invention will become apparent upon review of the following specification in conjunction with the drawings.

DESCRIPTION OF THE PREFERRED EMBODIMENT

Figure 1:
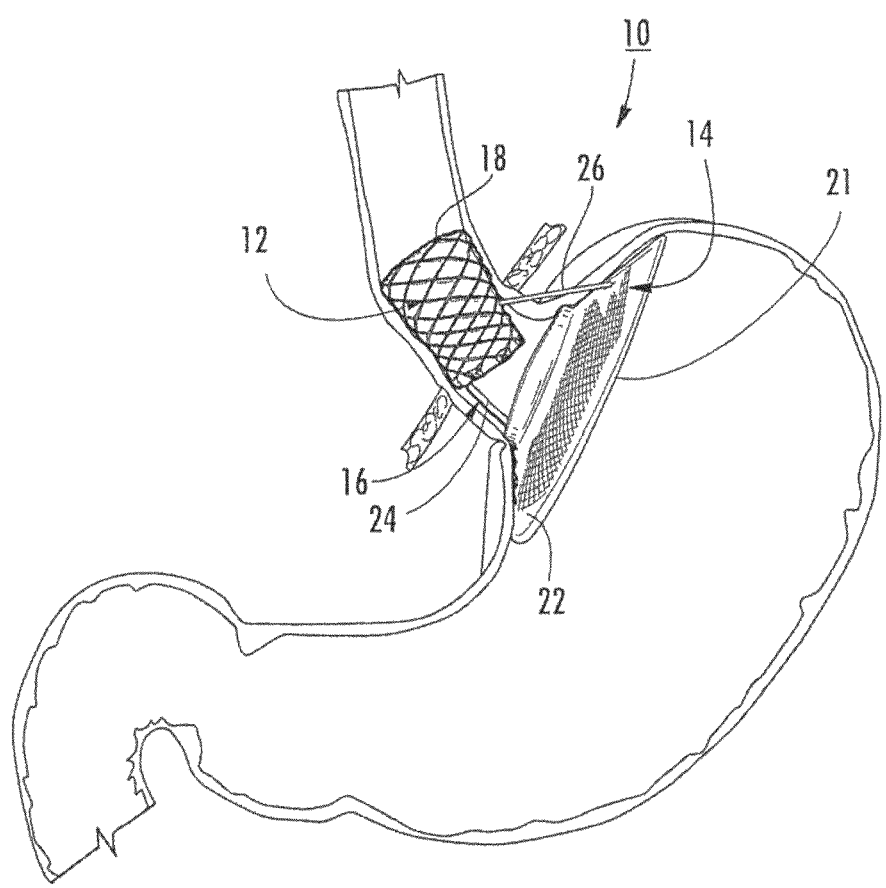
FIG. 1 is a front elevation of a bariatric device deployed in a recipient.

Referring now specifically to the drawings, and the illustrative embodiments depicted therein, a bariatric device, such as an endoluminal bariatric device 10 includes an esophageal member 12, a cardiac member 14, and a connector 16 that is connected with esophageal member 12 and cardiac member 14 (FIGS. 1-14). Esophageal member 12 has a wall 18 defining an esophageal surface 20 that is configured to generally conform to the shape and size of a portion of the esophagus, namely, at the abdominal portion of the esophagus adjacent the gastroesophageal (GE) junction. While illustrated as cylindrical in shape, wall 18 may be other shapes, such as a portion of a cylinder, or the like. Cardiac member 14 includes a body 21 defining a cardiac surface 22 that is configured to generally conform to the shape and size of at least a portion of the cardiac portion of the stomach. Connector 16, which is illustrated as a system of connector members, joins the esophageal and cardiac members. Connector 16 may include a tension member 24 which may be a semi-rigid strap which passes through the GE junction. Connector 16 may include one or more tethers 26 which may be attached to the esophageal and cardiac members and pass from the esophageal member to the cardiac member outside of the GE junction. As will be described in more detail below, this is accomplished by passing tether 26 through wall 18 of esophageal member 12 through the wall of the esophagus, through the wall of the stomach at the cardiac region, and through body 21 of the cardiac member.

Figure 2:
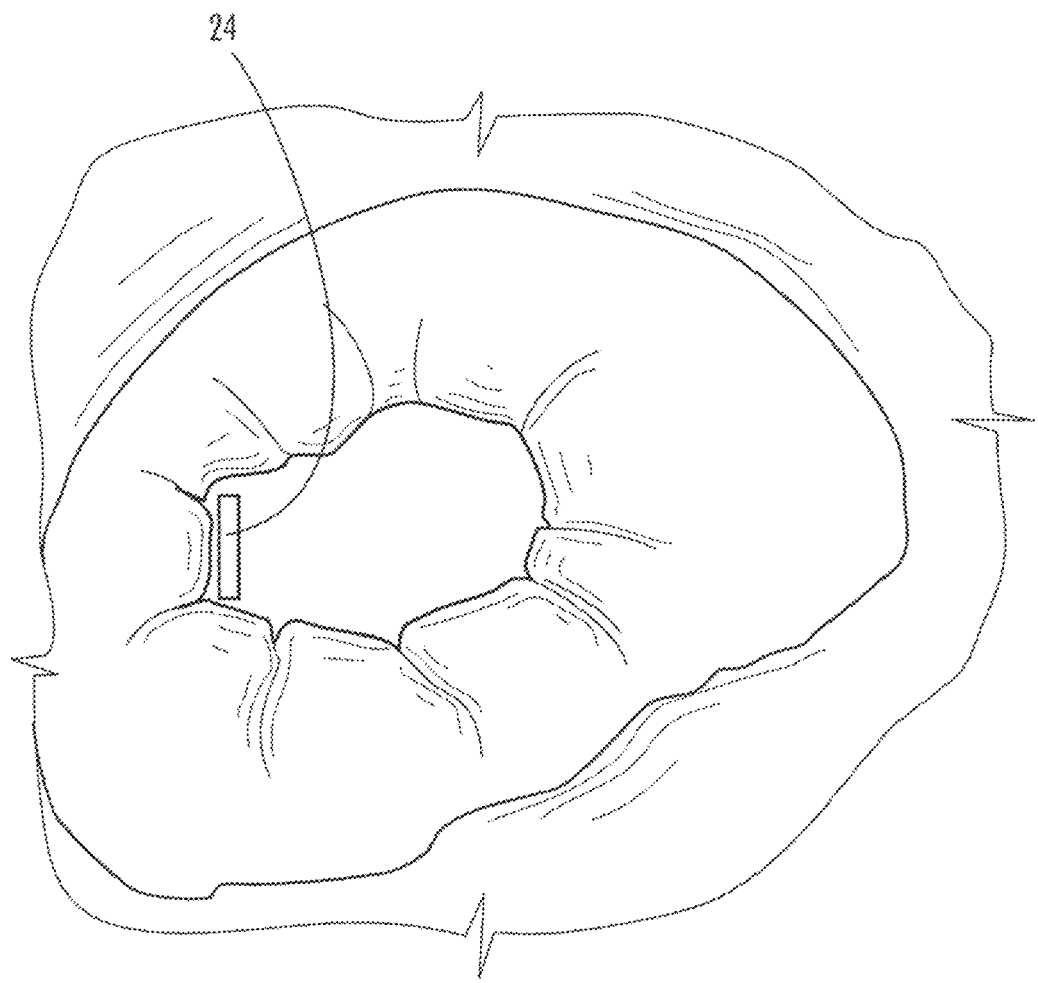
FIG. 2 is an illustration of a recipient's gastroesophageal (GE) junction in a dilated state with a bariatric device in place.
Figure 3:
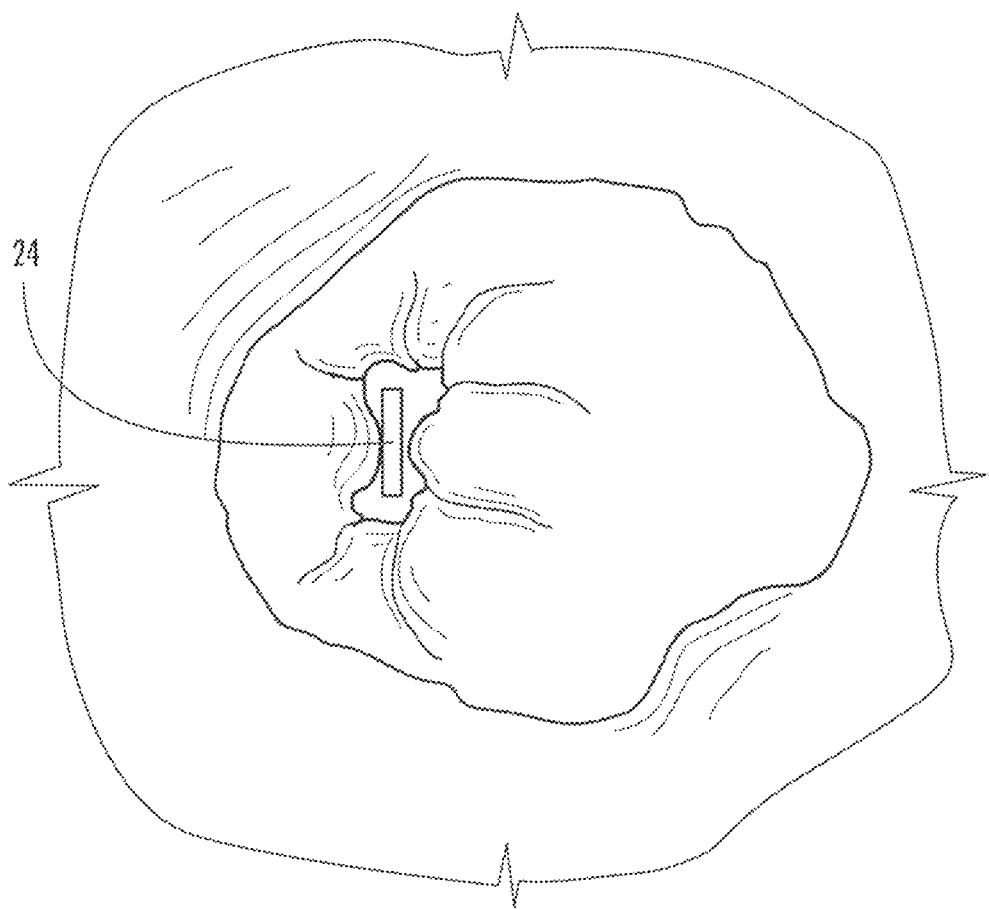
FIG. 3 is the same view as FIG. 2 with the GE junction in a constricted state.
Figure 4:
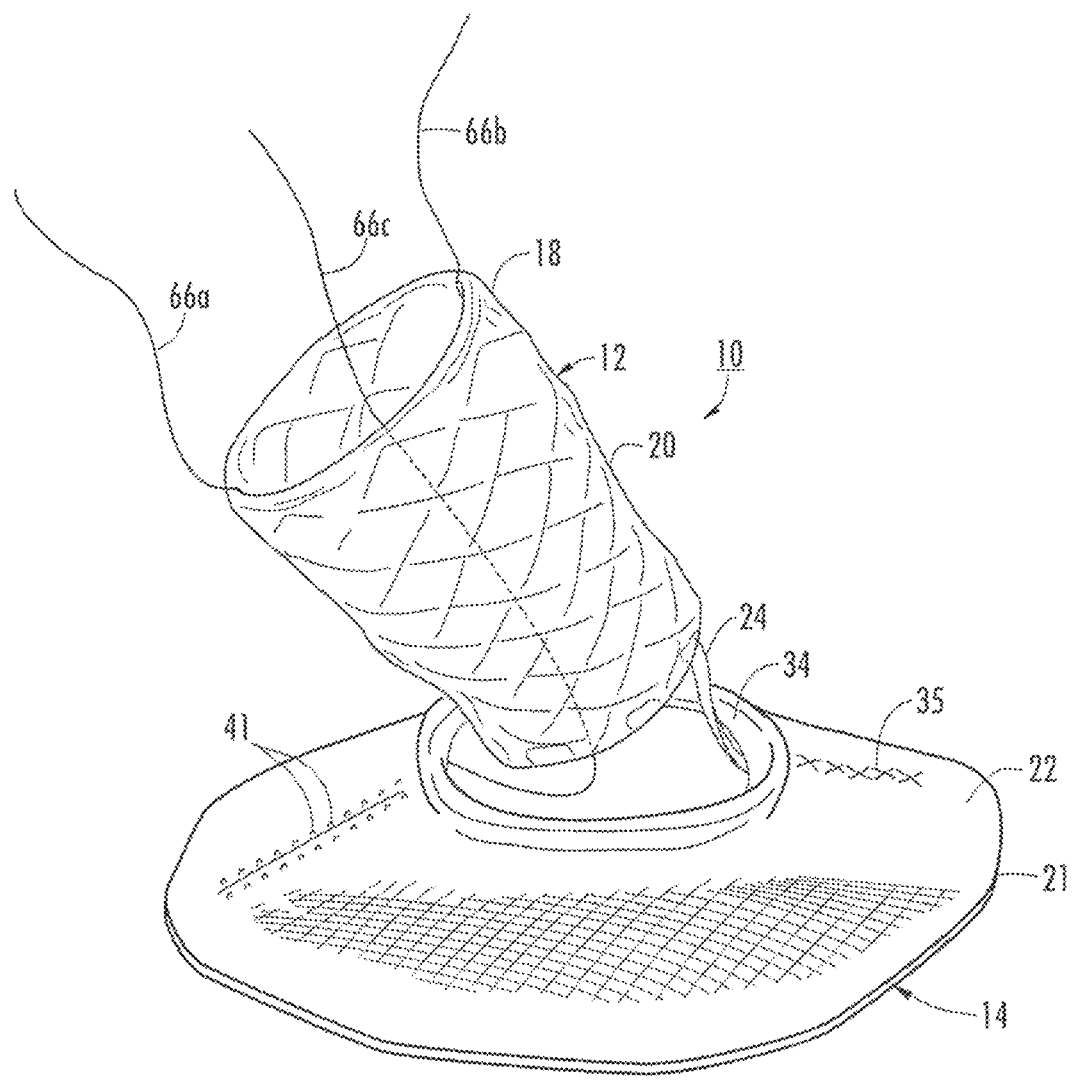
FIG. 4 is a perspective view of the bariatric device in FIG. 1 prior to deployment.
Figure 5:
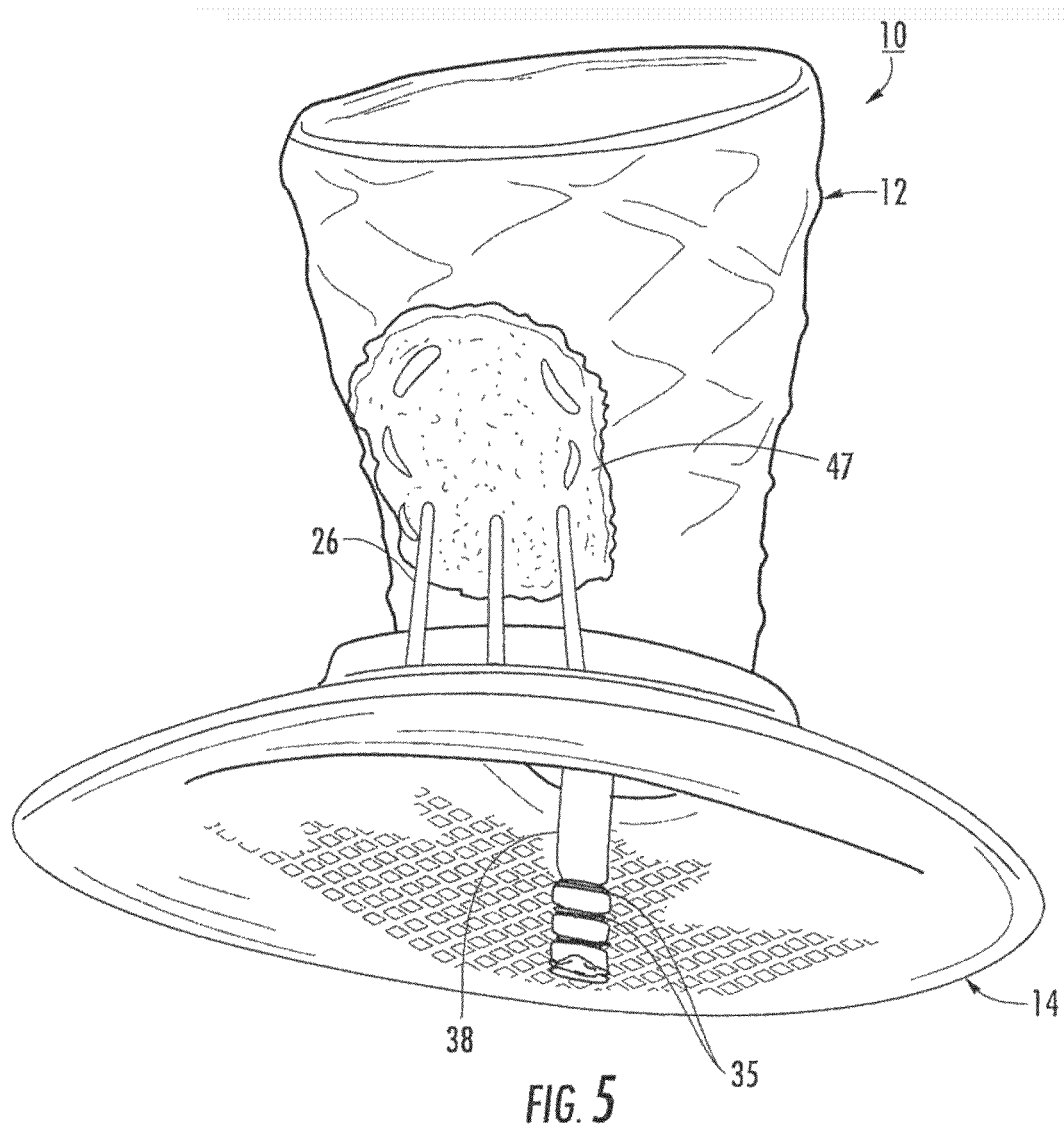
FIG. 5 is a perspective view of the bariatric device in FIG. 1 as deployed in a recipient as viewed from the angle of His.
Figure 6:
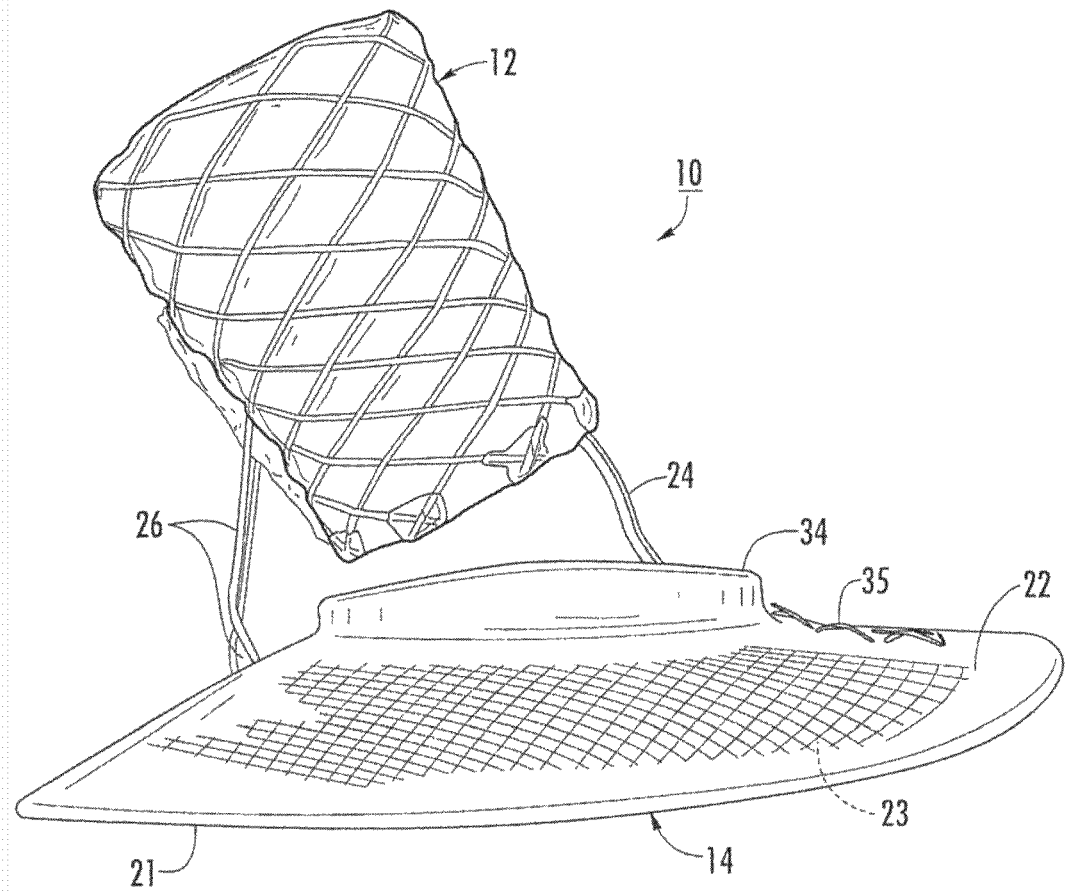
FIG. 6 is a rear elevation of the bariatric device in FIG. 1.
Figure 7:
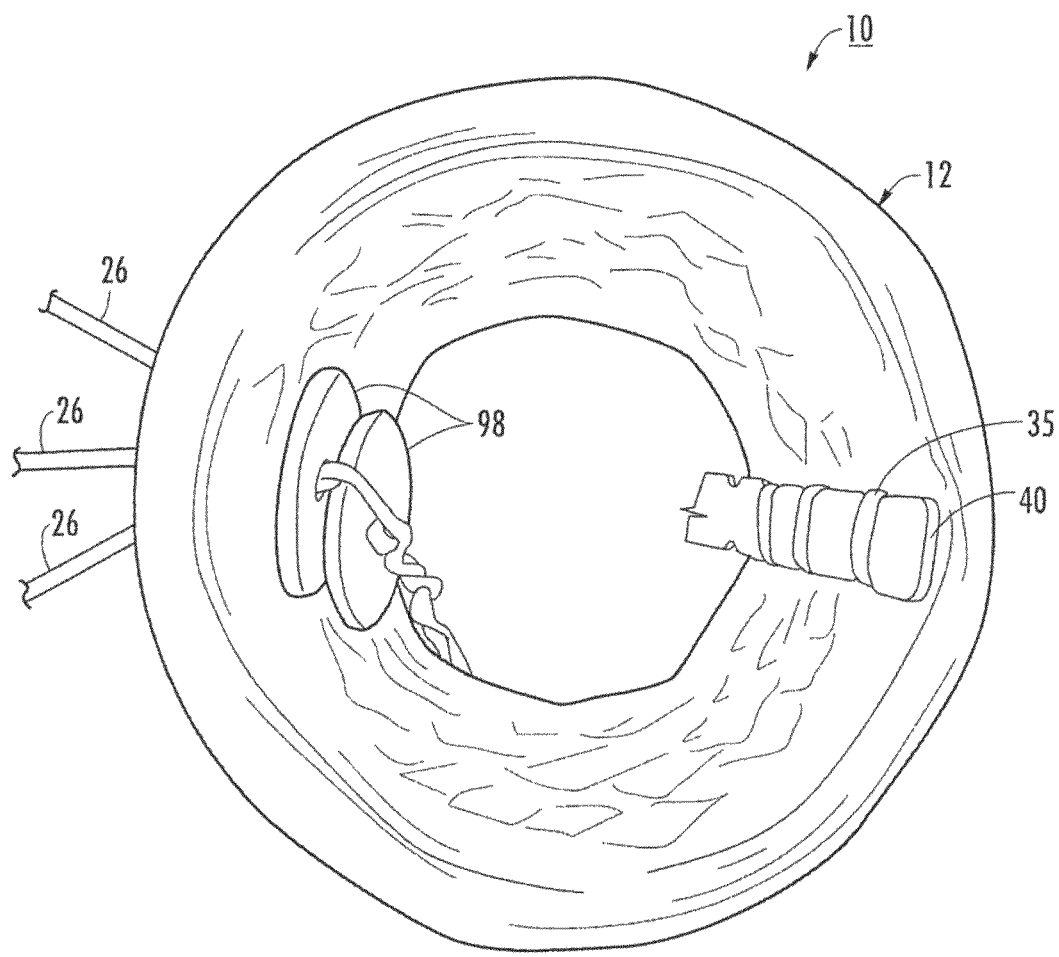
FIG. 7 is a proximal view of the bariatric device in FIG. 1.
Figure 8:
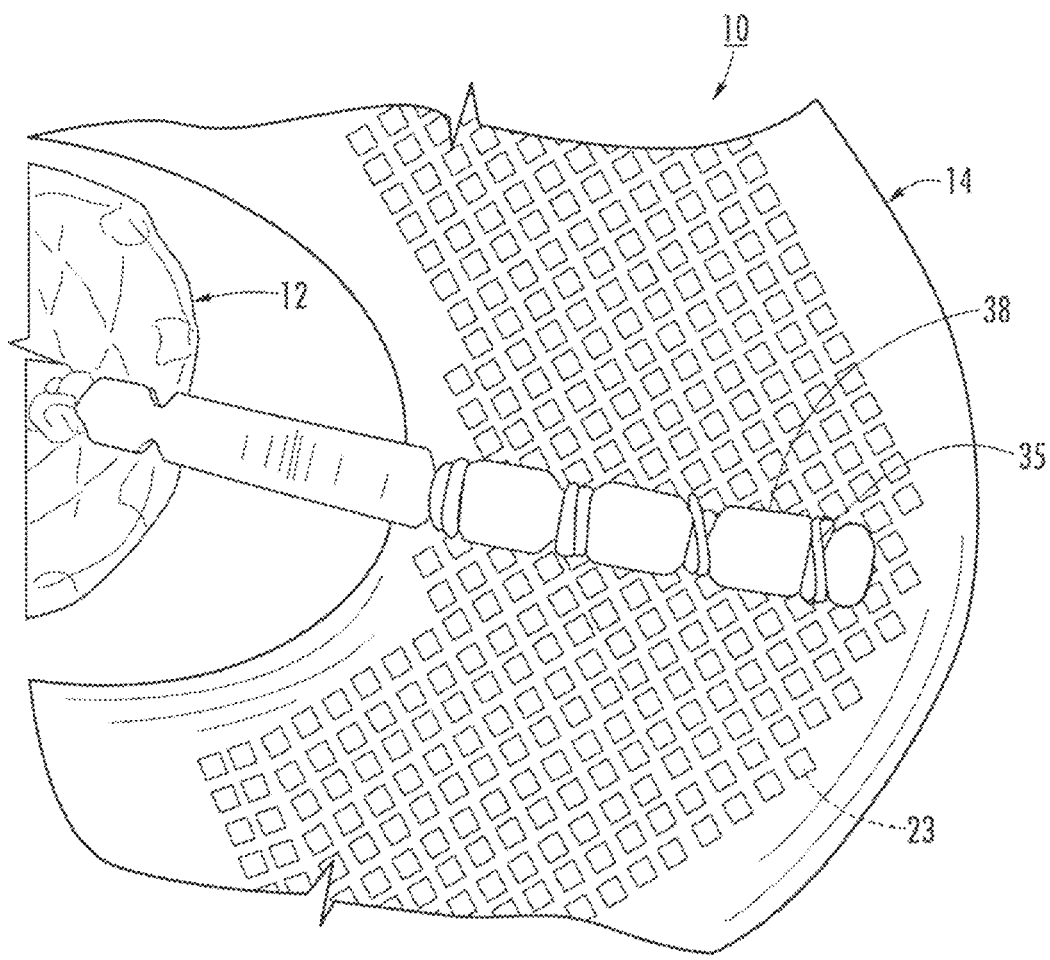
FIG. 8 is a distal view of the bariatric device in FIG. 1.
Figure 9:
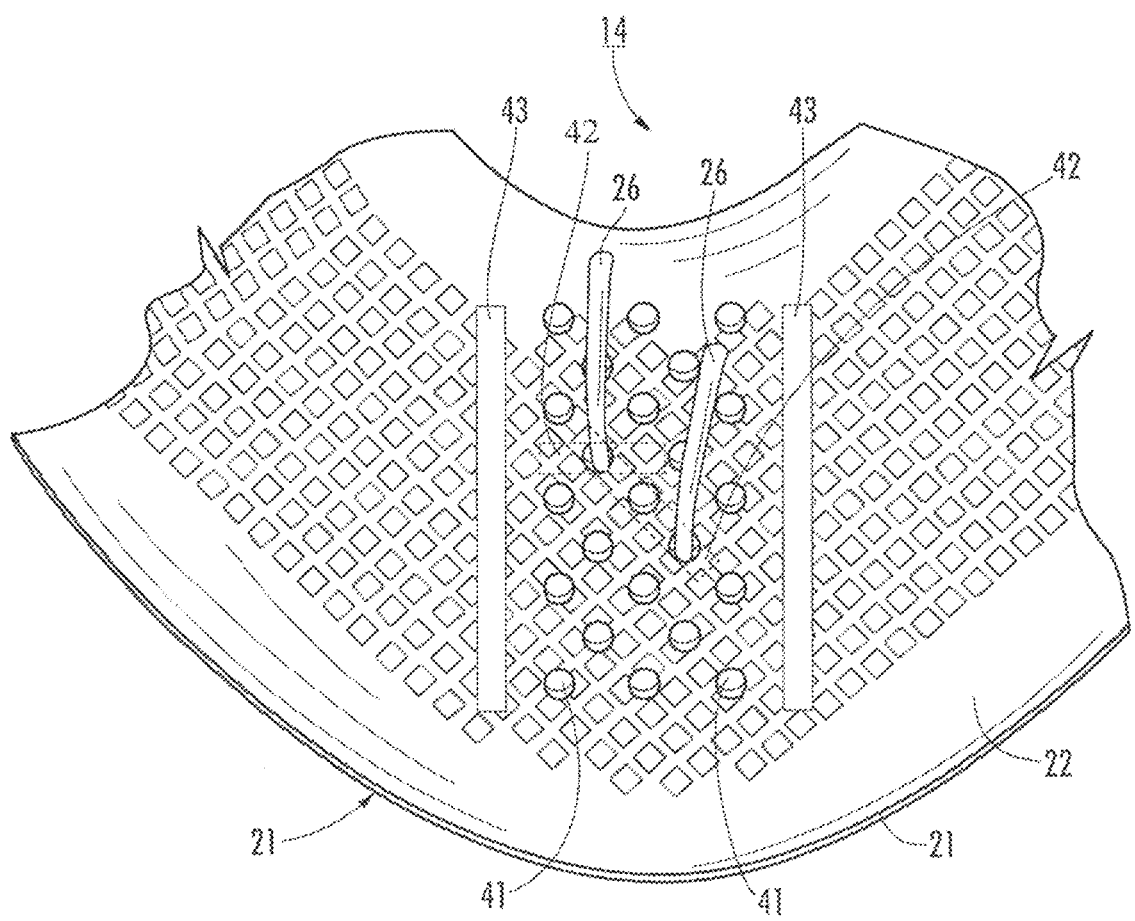
FIG. 9 is another distal view of the bariatric device in FIG. 1.

In the illustrated embodiments, connector 16 leaves most of the GE junction unrestrained. As best seen by comparing FIGS. 2 and 3, tension member 24 may be positioned opposite the angle of His. The portion of the pseudo-sphincter of the GE junction at the angle of His is relatively unrestrained by the connector and can constrict against the remainder of the pseudo-sphincter and tension member 24 as best seen in FIG. 3. Tension member 24 may include an inwardly curved portion 28 that allows the portion of the GE junction pseudo-sphincter opposite the angle of His to assume a relatively normal posture, again as illustrated in FIGS. 2 and 3. As best illustrated in FIG. 1, tether(s) 26 passes outside of the GE junction pseudo-sphincter through the walls of the esophagus and stomach. Once again, the pseudo-sphincter of the GE junction is allowed to constrict in a relatively unrestrained manner because the tether(s) do not significantly interfere with the pseudo-sphincter of the GE junction. Thus, connector 16 allows the GE junction to dilate for the passage of food (FIG. 2) and constrict when food is not passing (FIG. 3) in order to resist passage of stomach contents into the esophagus. Also, the GE junction pseudo-sphincter is allowed to function in a relatively normal manner for the purposes of belching, vomiting, and the like.

Figure 31:
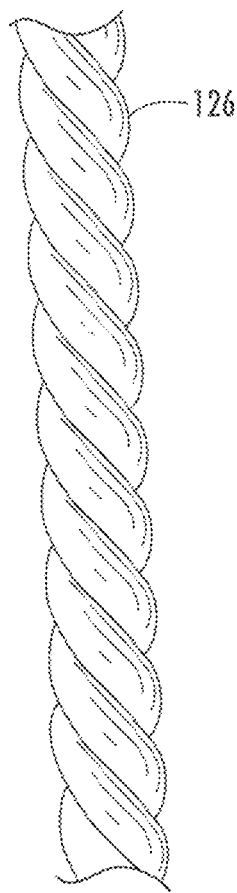
FIG. 31 is a perspective view of an alternative embodiment of a tether.

In the illustrated embodiment, most of the GE junction pseudo-sphincter is allowed to operate without substantial restraint. Indeed, at least 75 percent, and even 90 percent, of the GE junction may be unrestrained in order to function in a relatively normal fashion. In the illustrative embodiment, tension member 24 is made of 0.014 inch super-elastic Nitinol sheet. Because the tension member is in the form of a relatively thin semi-flexible strap, it is able to be folded back for the purpose of inserting the bariatric device through the esophagus for deployment, in a manner that will be described in more detail below. Tether(s) 26 may be an elongated filament, such as an uncoated silk suture, an Ethibond suture, an ePTFE suture, an elastic line, or the like. As will be described in more detail below, if desired, tether(s) 26 may be within a sheath to allow the filament to move lengthwise, for example, to facilitate subsequent adjustment of the spacing between the esophageal and cardiac members to adjust the degree of satiety. An uncoated silk suture may produce fibrous tissue, which may prevent lateral drift of the tether through the tissue at the GE junction. Alternatively, a tether 126 may be used having a surface that promotes tissue attachment and/or tissue ingrowth (FIG. 31) to prevent lateral drift of the tether.

As will be described in more detail below, connector 16 may be generally in tension and cardiac surface 22 stimulates mechanoreceptors in the cardiac region of the recipient in order to influence a neurohormonal feedback mechanism of the recipient sufficient to cause the recipient to lose weight. While the precise manner of causing this effect is not completely known, it may result from an increase in the metabolic rate of the recipient and may cause at least partial satiety by augmenting fullness caused by food and simulating fullness in the absence of food, as described in commonly assigned International Publication No. WO 2006/044640 A1 entitled BARIATRIC DEVICE AND METHOD, the disclosure of which is hereby incorporated herein by reference in its entirety. As described in WO '640, this may be accomplished without mechanically restricting the food intake, such as by inserting a restriction device in the esophagus, GE junction, or the like, utilized in prior art bariatric devices. Esophageal surface 20 may additionally contribute to satiety and/or increase in metabolic rate, but its primary function is to work in collaboration with connector 16 and cardiac member 14 to resist distal migration of bariatric device 10. Also, connector 16, particularly tension member 24, may apply pressure at a portion of the GE junction and, thereby, assist in generating satiety.

As previously described, cardiac surface 22 of cardiac member 14 and the esophageal surface of the esophageal member are configured to stimulate mechanoreceptors at the abdominal portion of the esophagus, the esophageal-gastric junction and/or the cardia of the recipient. The mechanoreceptors stimulated may be tension receptors, which are sensitive to contraction and elongation; stretch receptors, which are sensitive to elongation only; and/or baroreceptors, which are stimulated by change in pressure. This stimulation may be accomplished by cardiac surface 22 and esophageal surface 20 exerting a strain, such as an outward pressure, typically a generally radial outward pressure, to the wall of the cardiac region of the stomach and the abdominal portion of the esophagus. This may be accomplished, at least in part, by the connector 16 transmitting forces between the esophageal member and the cardiac member to press cardiac surface 22 against the cardia. It may also be accomplished, at least in part, by configuring the wall of the esophageal member to create an interference fit with the abdominal portion of the esophagus. The bariatric device may, alternatively, apply an inward force on the abdominal portion of the abdominal portion of the esophagus, the esophageal-gastric junction and/or cardia. The bariatric device may, alternatively, apply a longitudinal force, such as a proximal/distal force, to the abdominal portion of the esophagus, the esophageal-gastric junction and/or the cardia.

The strain exerted by the bariatric device influences receptors of the neurohormonal feedback mechanism of the neurohormonal system, also known as the neuroendocrine system, present at the esophagus and/or stomach to cause weight loss. The strain that influences the neurohormonal feedback mechanism present at the abdominal portion of the esophagus, the esophageal-gastric junction and/or the cardiac portion of the stomach is intended to be relatively consistent over as large an area as reasonably possible. In contrast to prior proposed devices, such as restriction devices, which require that the recipient ingest food in order to influence neurohormonal feedback mechanisms, the embodiments of the bariatric devices disclosed herein is effective in the absence of food. It also augments fullness caused by food.

Tension member 24 interconnects the esophageal and cardiac members, as previously described, and may also serve as a location for fastening of the bariatric device, such as to the muscularis at the GE junction, such as by using conventional sutures passed around the strap or by specialized clips (not shown) that can be deployed in situ to connect the strap with the recipient. Tether(s) 26 serves to resist distal migration because the tether passes through the esophageal wall and the stomach wall and creates a sort of sandwiching of the esophageal wall and the stomach wall between esophageal surface 20 and cardiac surface 22. This is due, in part, to the upward extension of the cardia at the angle of His to be somewhat parallel to the esophageal wall. Connector 16 also serves to bring cardiac surface 22 into engagement with the cardia in order to stimulate the neuroreceptors, which are dominant in the cardia. Thus, it is seen that esophageal member 12, cardiac member 14, and connector 16 all operate in unison to resist distal migration of bariatric device 10 while causing satiety and thereby weight loss in the recipient.

Cardiac member 14 may be made of a generally resilient material having sufficient flexibility to allow it to be compacted to pass through the esophagus while having sufficient rigidity to allow it to transmit strain from connector 16 to the cardiac region of the stomach. In the illustrated embodiment, body 21 of cardiac member 14 is made from a molded silicone, such as 60 durometer LSR silicone with an embedded mesh such as a fabric mesh 23 of the type that is known in the art, such as a precision woven polypropylene 35.5× 35.5 mesh. The mesh increases tear resistance and stiffness. Body 21 may include a proximally raised portion 34 defining a flange. Flange 34 is configured to fit against the GE junction. This causes food to be directed through-opening 36 in body 21 while resisting the food passing between cardiac surface 22 and the wall of the stomach. In the illustrated embodiment, cardiac member 14 may be configured to apply a nominal strain on an order of magnitude of 6.5 PSI to the cardia, although the actual pressure may vary depending on installation factors, such as tension on the tether(s), or the like. In the illustrated embodiments, cardiac member 14 is configured to engage the cardia and not the fundus of the stomach. The cardia is resistant to dilation due to its structure while the fundus is subject to dilation. Therefore, cardiac member 14 stimulates the mechanoreceptors without causing substantial dilation.

Figure 13:
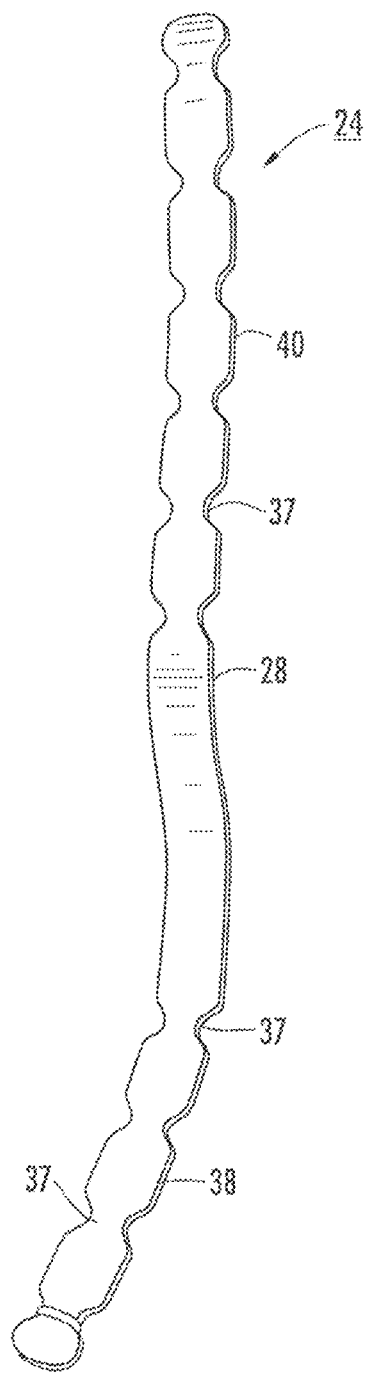
FIG. 13 is a perspective view of a tension member.
Figure 13A:
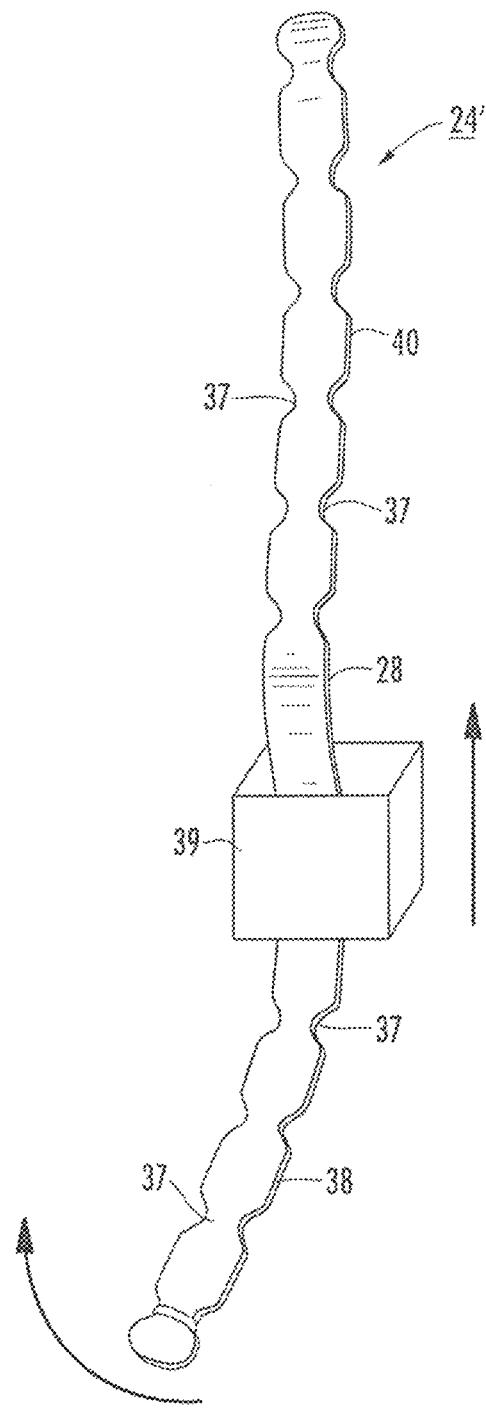
FIG. 13a is the same view as FIG. 13 of an alternative embodiment thereof.
Figure 14:
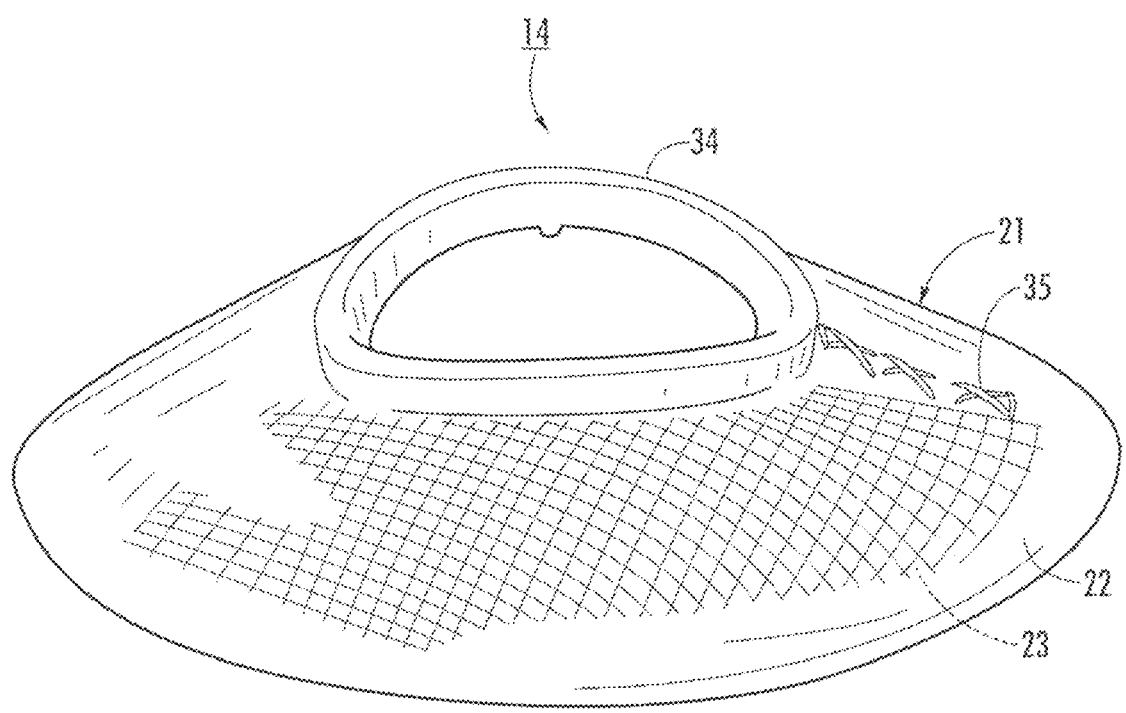
FIG. 14 is a perspective view of a cardiac member.

Tension member 24 may pass through-opening 36 and has an extension 38 that fastens to body 21 of the cardiac member opposite cardiac surface 22, such as by suture material 35 (FIG. 13). Grooves 37 may be provided to stabilize the suture material. Extension 38 may also be attached to body 21 by being inset molded, and/or using fasteners, or the like. Tension member 24 additionally includes a proximal extension 40 that attaches to wall 18 of esophageal member 12 using similar techniques. An alternative embodiment of a tension member 24' is illustrated as including an adjustment mechanism 39 (FIG. 13a). Adjustment mechanism 39 may adjust either the relative angle between extension 38 and proximal extension 40 or may adjust the length of extension 38 relative to proximal extension 40. Adjustment mechanism 39 may be operable by a physician transorally to adjust the orientation of cardiac member 21 with respect to esophageal member 12. This allows the bariatric device to conform to the recipient's anatomy and to apply a desired pressure to the cardiac region of the stomach. Alternatively, adjustment mechanism 39 may be adjusted by a control of the type disclosed in International Publication No. WO 2006/044640 A1 entitled BARIATRIC DEVICE AND METHOD, the disclosure of which is hereby incorporated herein by reference in its entirety.

Figure 18:
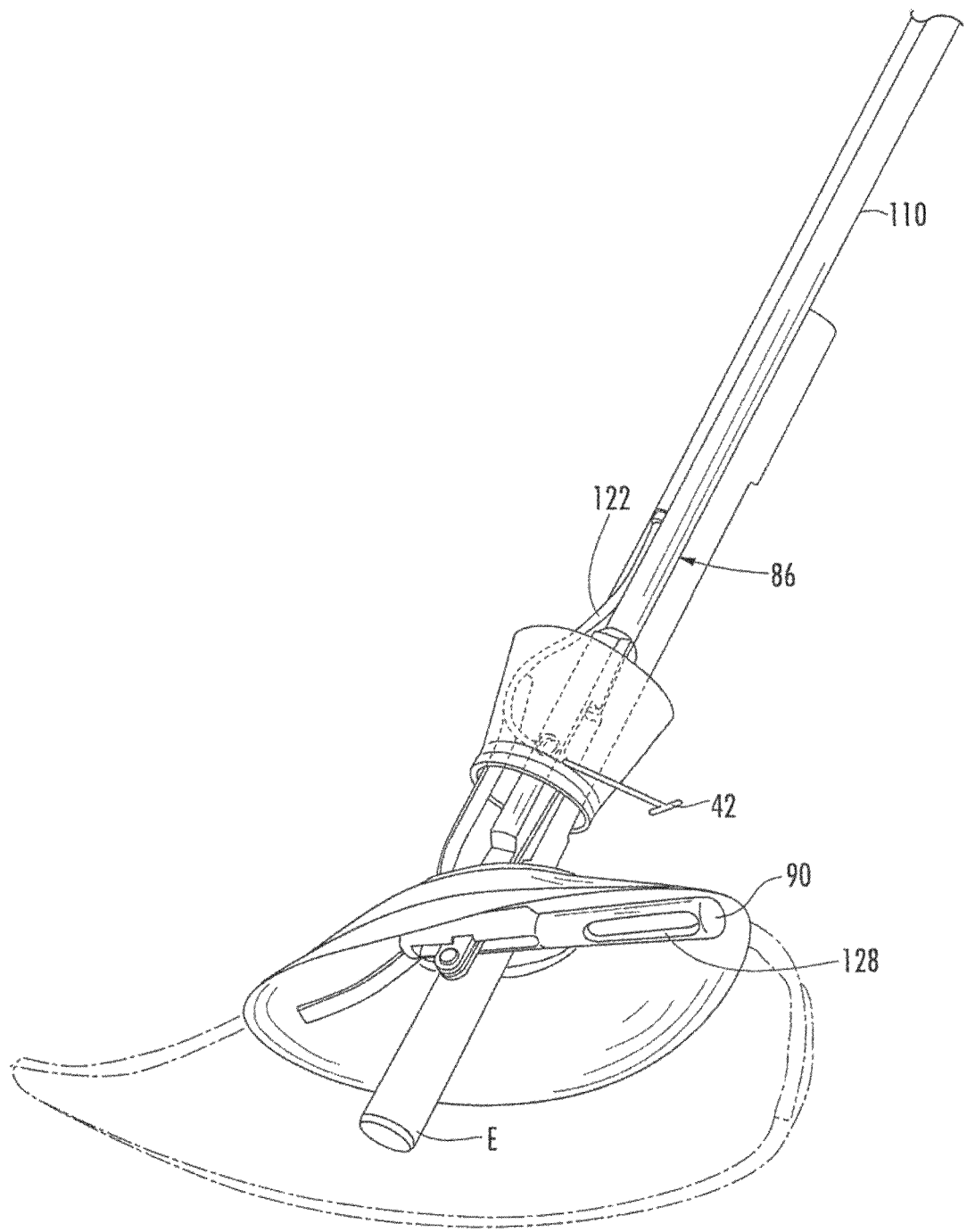
FIG. 18 is a perspective view of a medical device fixation tool fixing a bariatric device.
Figure 19:
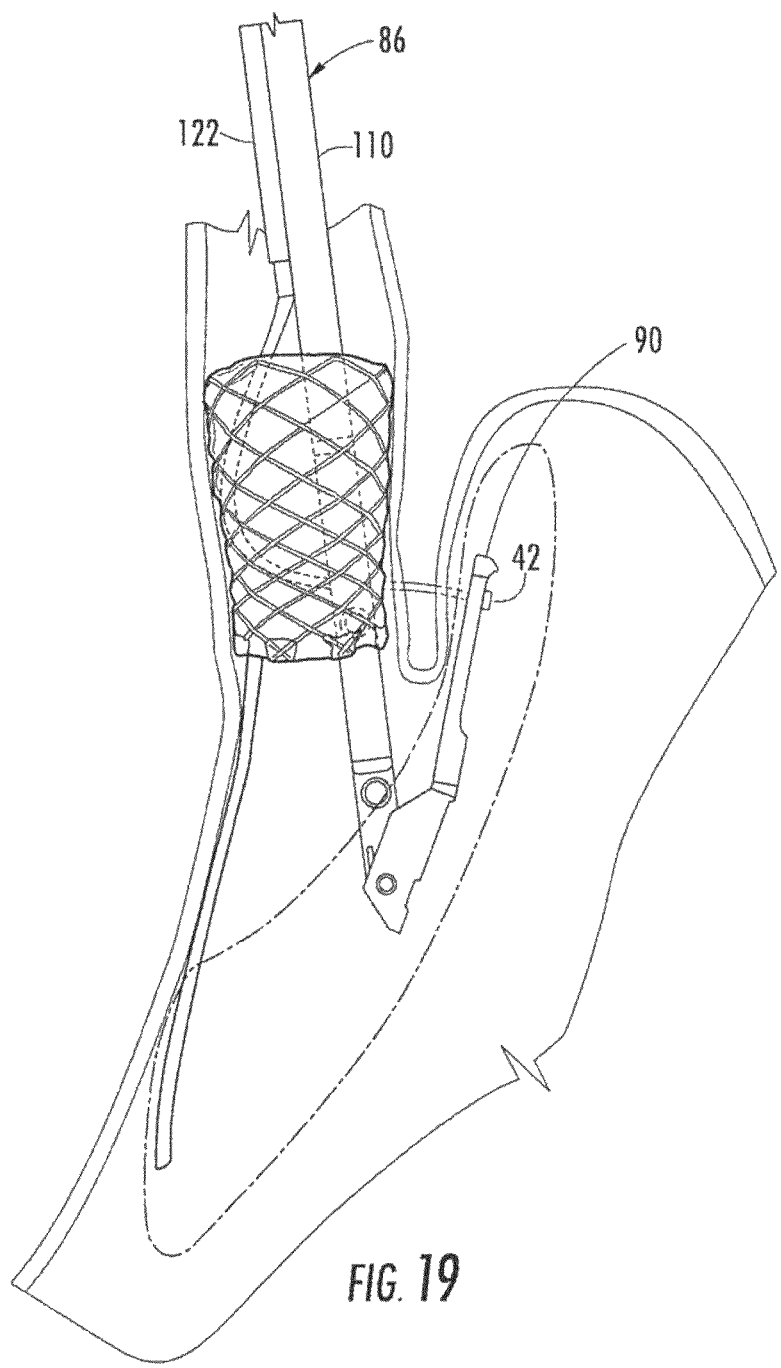
FIG. 19 is an elevation of the medical device fixation tool fixing the bariatric device in FIG. 18.
Figure 20:
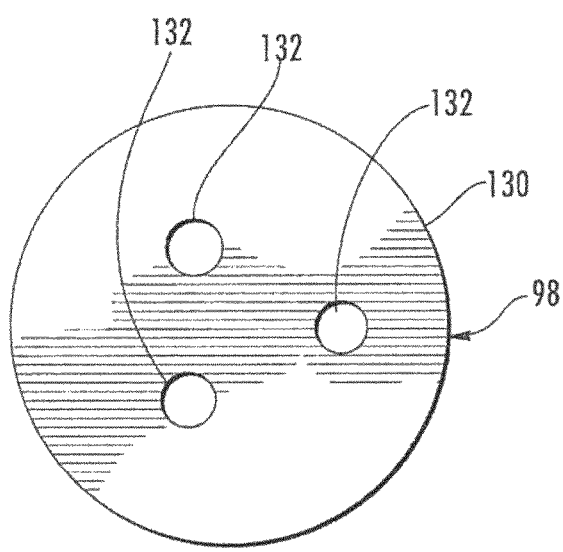
FIG. 20 is an elevation of a tether clamp.

Tether 26 may be held in place proximately by a tether clamp, such as a button 98, on an interior surface of wall 18 of esophageal member 12 and may be held in place distally by a tether clamp, such as a T-fastener, against a surface of body 21 opposite cardiac surface 22. In the illustrated embodiment, a T-fastener 42 is attached to the distal and of each tether and is passed through esophageal wall 18 and cardiac member body 21 utilizing a medical device fixation tool, or tether device, 86. Tether device 86 is described in detail in commonly assigned International Patent Application No. PCT/US2008/053962, filed on Feb. 14, 2008, entitled MEDICAL DEVICE FIXATION TOOL AND METHOD OF FIXATION OF A MEDICAL DEVICE, and in U.S. provisional patent application Ser. No. 60/901,457 filed on Feb. 14, 2007, and U.S. provisional patent application Ser. No. 60/921,930, filed on Apr. 5, 2007, entitled BARIATRIC DEVICE AND METHOD, the disclosures of which are hereby incorporated herein by reference in their entirety. Suffice it to say that tether device 86 may include a cardiac support 90 that is positioned by a shaft 110 within the recipient's stomach. Cardiac support 90 may be pivoted between a deployment position aligned with shaft 110 and a use position supporting the cardiac member 21 by an actuator (not shown) as illustrated in FIGS. 18 and 19. A needle firing actuator, or needle driver, 122 is capable of propelling a needle carrying T-fastener 42 through wall 18 through cardiac member body 21 and through an opening 128 in cardiac support 90. Alternatively, T-fastener 42 can have a pointed end and be driven directly by needle driver 122 through wall 18 and body 21. Once T-fastener 42 is through the cardiac member, proximal tension on tether 26 will seat T-fastener 42 and pull cardiac surface 22 against the cardia of the recipient.

Body 21 may be formed with a series of openings 41 at a portion of the body that is opposite from tension member 24. The needle driver 122 of the tether device may align with one of openings 41 thereby easing the passage of the tether through body 21. However, the nature of the material making up body 21 would accommodate passage of the tether without openings 21. One or more radiopaque surfaces 43 may be provided opposite tension member 24 or the entire body 21 could be radiopaque. These allow the physician to visualize the angle of cardiac surface 22 using fluoroscopy to assist in placement of the bariatric device in the recipient. Also, the angle between cardiac surface 22 and esophageal member 12 can be visualized if the esophageal member has any metallic or other radiopaque component. This allows the physician to determine if the cardiac surface and esophageal member are too close together, which could risk the bariatric device migrating, or too far apart, which could produce insufficient satiety. Also, a surface feature, such as an indentation and/or raised shoulders, could be formed on body 21 opposite cardiac surface 22 that conforms to support 90 to assist in maintaining alignment between support 90 and body 21 during driving of the needle through body 21.

Alternatively, a bariatric device 10' may be provided in which tether clamps in the form of buttons 98 are applied to tether(s) 26 after needles attached to tether(s) 26 passes through walls 18 and 21 and the recipient's esophageal wall and stomach wall in a manner that will be explained in more detail below (FIGS. 23-26).

Figure 10:
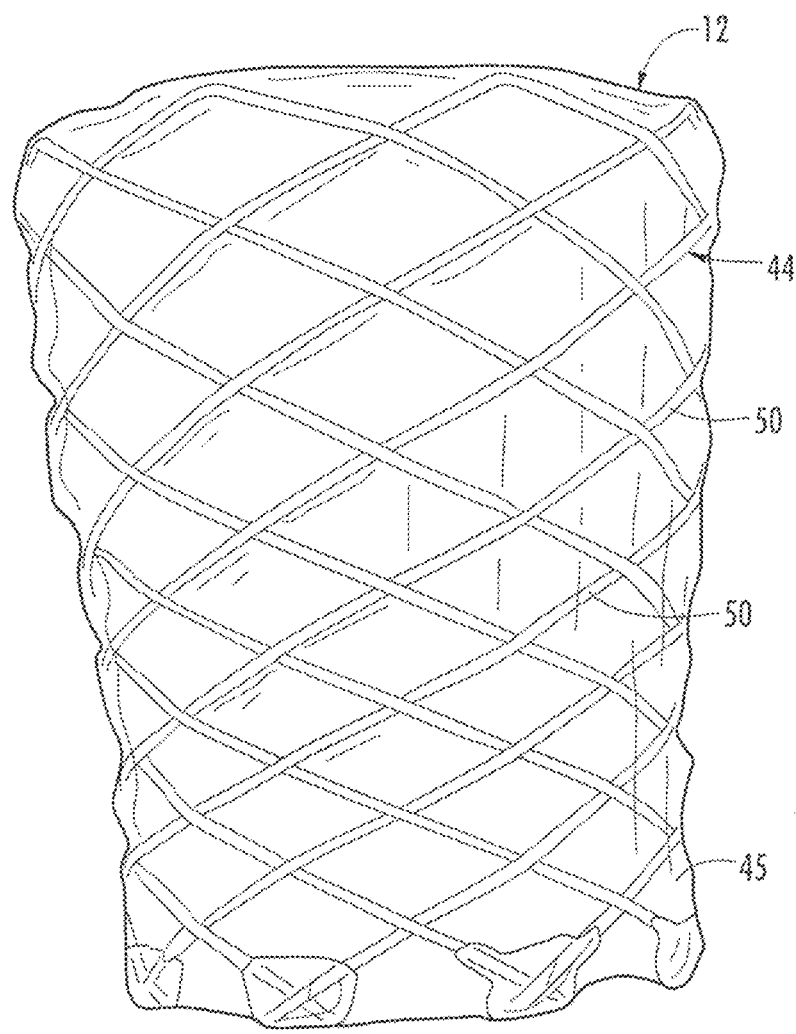
FIG. 10 is an elevation of an esophageal member.
Figure 11:
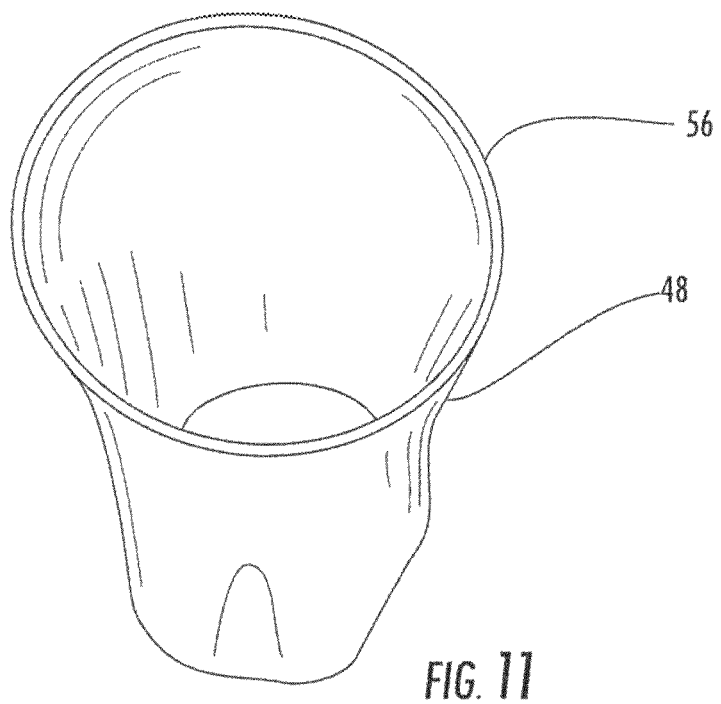
FIG. 11 is a perspective view of an outer sleeve of the esophageal member in FIG. 10.
Figure 12:
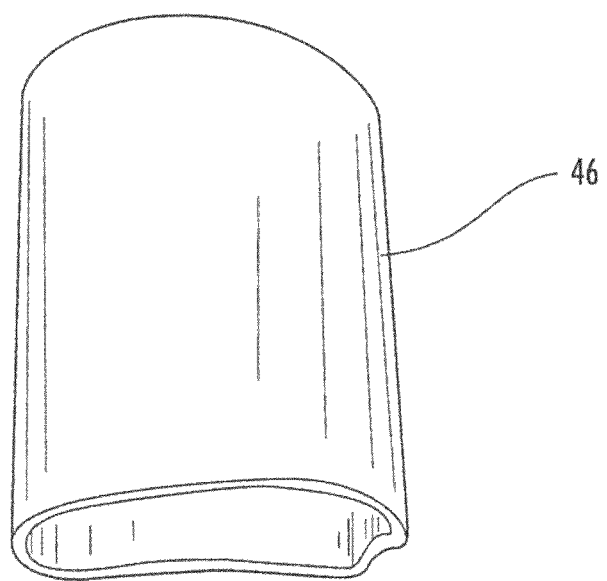
FIG. 12 is a perspective view of an inner sleeve of the esophageal member in FIG. 10.
Figure 27:
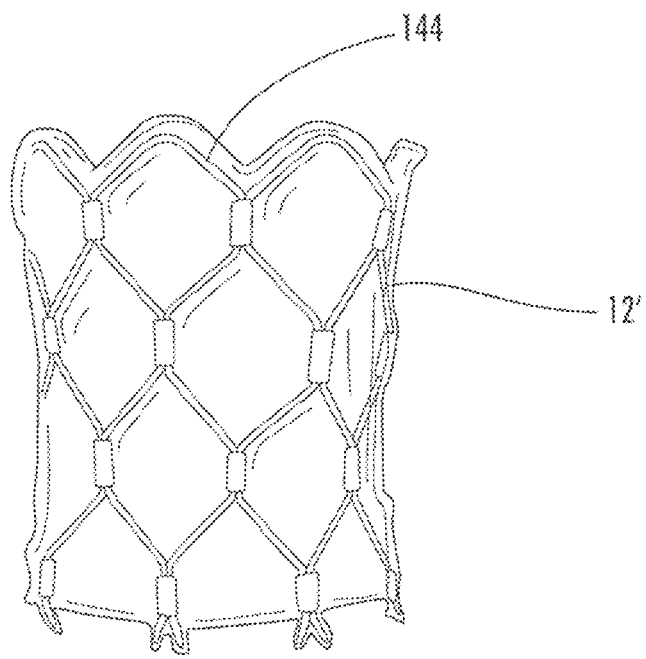
FIG. 27 is an elevation of an esophageal member of the bariatric device in FIG. 23.
Figure 28:
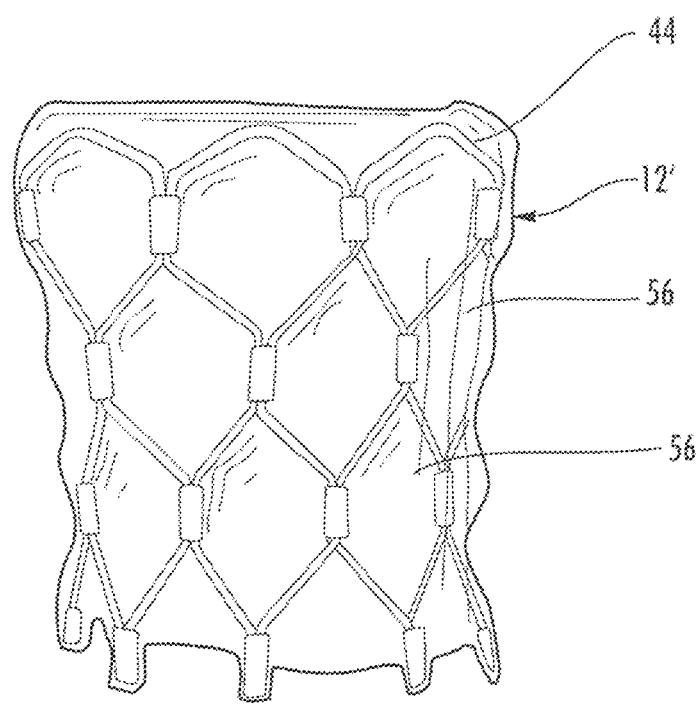
FIG. 28 is the same view as FIG. 27 of an alternative embodiment of an esophageal member.
Figure 29:
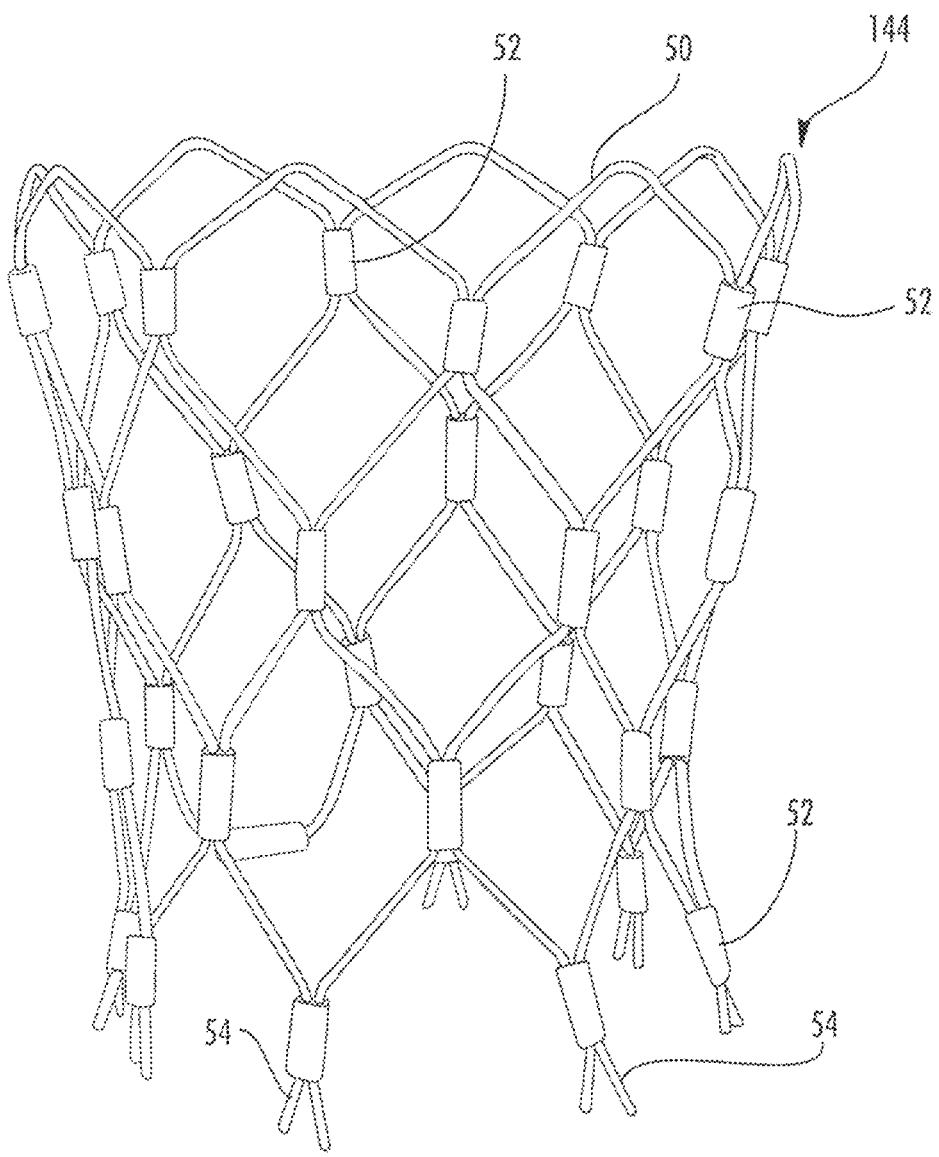
FIG. 29 is a perspective view of a cage structure used in the esophageal member in FIG. 27.

Esophageal member 12 may include a cage 44, and an impervious wall 45 covering cage 44. Wall 45 may be provided by an inner sleeve 46, and an outer sleeve 48 covering cage 44 (FIGS. 10-12). A pad 47 made from a tissue attachment or tissue ingrowth material may be provided on esophageal member 12 where the tethers enter the esophagus to long-term attachment. Pad 47 may be made of a polypropylene mesh. Cage 44 may be made from an elongated member 50, which, in the illustrated embodiment, is an elastic member, such as Nitinol wire. Member 50 is formed as an interwoven spiral, as illustrated in FIG. 10. Alternatively, esophageal member 12 may utilize a cage 144 in which the elongated member is formed as a lattice and joined at adjacent points, such as by ferrules 52 (FIGS. 27-29). Distal ends 54 of elongated members 50 may form distal tines 54 to resist distal migration of esophageal member 12. Esophageal member 12 may be outwardly flared proximally, in order to ensure contact with the esophageal wall, and may be outwardly flared distally in order to assist the engagement of tines 54 at the wall of the organ, such as the thick musculara adjacent the GE junction. Tines 54 may be slightly outwardly extending in order to ensure penetration of the organ wall. In the illustrated embodiment, tines 54 have a length of approximately 1.5 mm.

Figure 30:
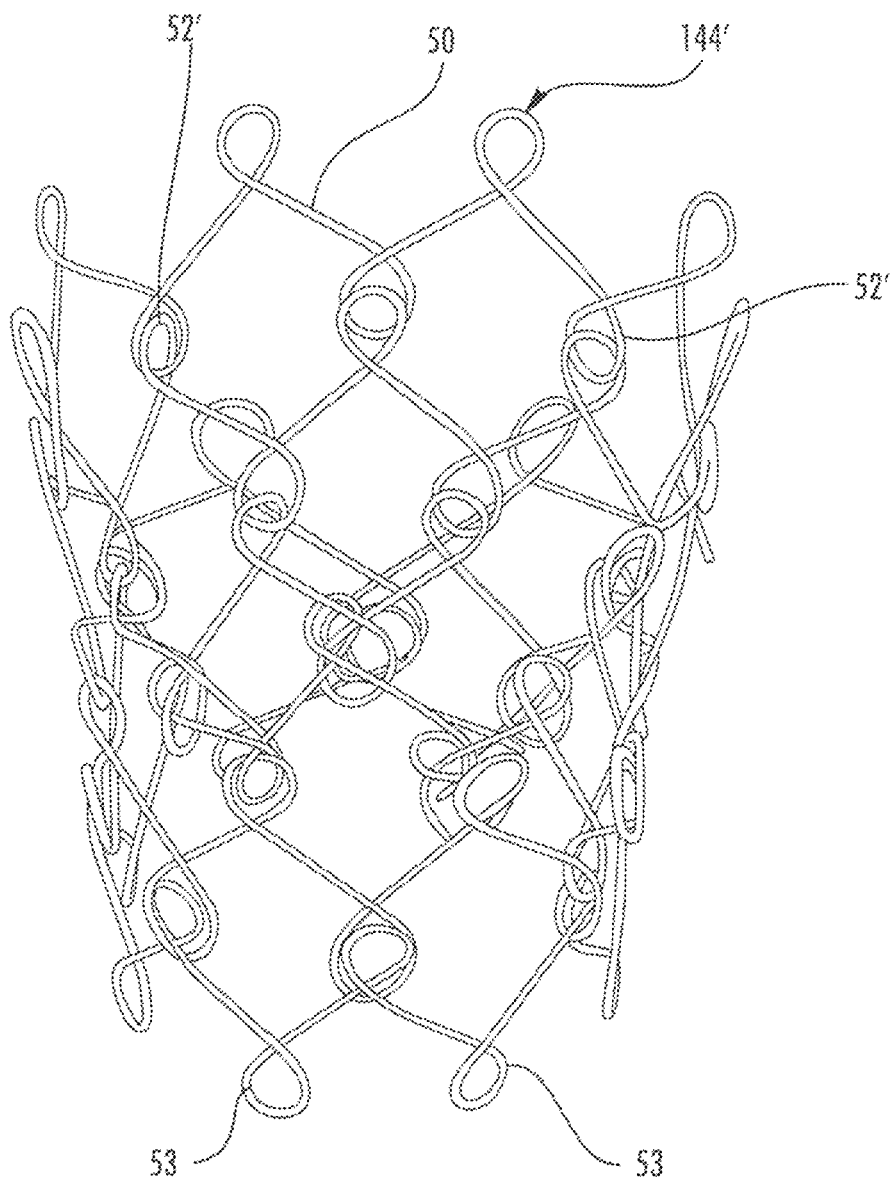
FIG. 30 is the same view as FIG. 29 of an alternative embodiment of an esophageal member cage structure.

An alternative embodiment of a cage 44' is made from an elongated member 50' that is formed into the three-dimensional structure without the requirement for separate ferrules to join adjacent portions of the structure (FIG. 30). This is accomplished by inter-looping the elongated member at adjacent portions, as illustrated at 52'. In the embodiment illustrated in FIG. 29, cage 44' does not include tines at a distal end portion thereof. Other embodiments will be apparent to the skilled artisan. For example, a circumferential ring (not shown) may be provided at a proximal portion of cage 44, 44' in order to provide for the transfer of axial forces around the perimeter of the cage. This may be useful, for example, in order to provide a grasping member should it be desired to remove the bariatric device, reposition the esophageal member, or the like. Due to the structure of cage 44, 44', a proximal force placed upon a proximal end thereof should result in a reduction in diameter in the cage that would allow the cage to be pulled into an overtube of the type that is known in the art. Once in the overtube, the esophageal member could be rotated or repositioned proximally or distally or the bariatric device removed. An alternative embodiment of a cage 144' includes a portion of elongated member 50 that is looped distally to define a tether attachment portion of wall 18. The purpose of loop 50 is to provide reinforcement to wall 18 to support attachment of the tether(s).

Esophageal member 12 may include an inner sleeve 46 and an outer sleeve 48 over cage 44, 144, 144' (FIGS. 11 and 12) defining wall 18. Each sleeve in the illustrated embodiment may be made of 0.005 thickness of silicone and may include an outer taper 56 proximally and/or distally in order to conform to the shape of cage 44, 44'. With inner sleeve 46 and outer sleeve 48 positioned over the cage, the sleeves may be joined. The inner and outer sleeves may be fused, or laminated, at all points where possible within the openings of the cage. In an alternative embodiment, inner and outer sleeves 46, 48 may be fused at smaller fusion areas which are smaller than the respective opening in the cage. This may be accomplished, by way of example, by forming an opening at corresponding portions of the inner and outer sleeves and fusing the sleeves at that area, such as by the use of a biologically compatible adhesive, such as a silicone adhesive, or the like. The amount of fusion, or lamination, may affect the amount of rigidity of the esophageal member in resisting lateral forces. This may be used, in combination with the structure of the cage and the diameter of the elongated member 50 to adjust the amount of strain placed by the esophageal member on the esophagus by the esophageal member. Although illustrated as made from Nitinol wire, esophageal, the cage may be made from other material, such as a polyetheretherkeytone polymer (PEEK), carbon fiber filament, or the like.

In the illustrated embodiment, esophageal member 12 is between 1.8 cm and 2.1 cm inner diameter with 2.2 cm flare at the proximal end portion. It may have a length of between 2 cm to 3 cm or more if needed for anchoring. However, a shorter length tends to reduce the likelihood of food forming an obstruction in the esophageal member. It should be understood that size may vary as a function of the size and anatomy of the recipient. Esophageal member 12 and/or cardiac member 14 may be affixed in whole or in part using the mucosal capture technique disclosed in commonly assigned International Application No. PCT/US08/53797 filed on Feb. 13, 2008, entitled MUCOSAL CAPTURE FIXATION OF MEDICAL DEVICE, the disclosure of which is hereby incorporated herein by reference in its entirety.

Figure 15A:
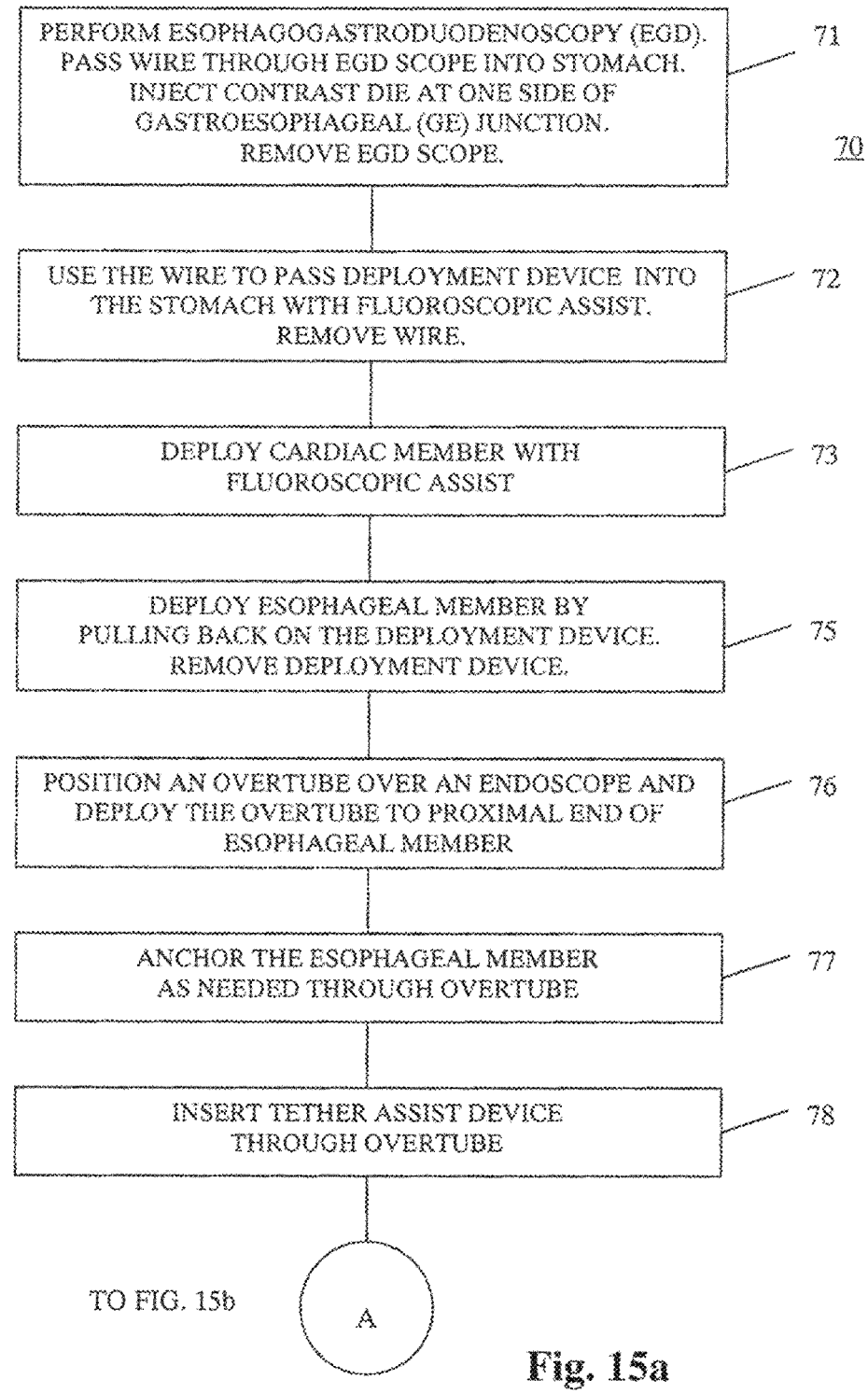
FIGS. 15a and 15b are a flowchart of a procedure for deployment of a bariatric device.
Figure 15B:
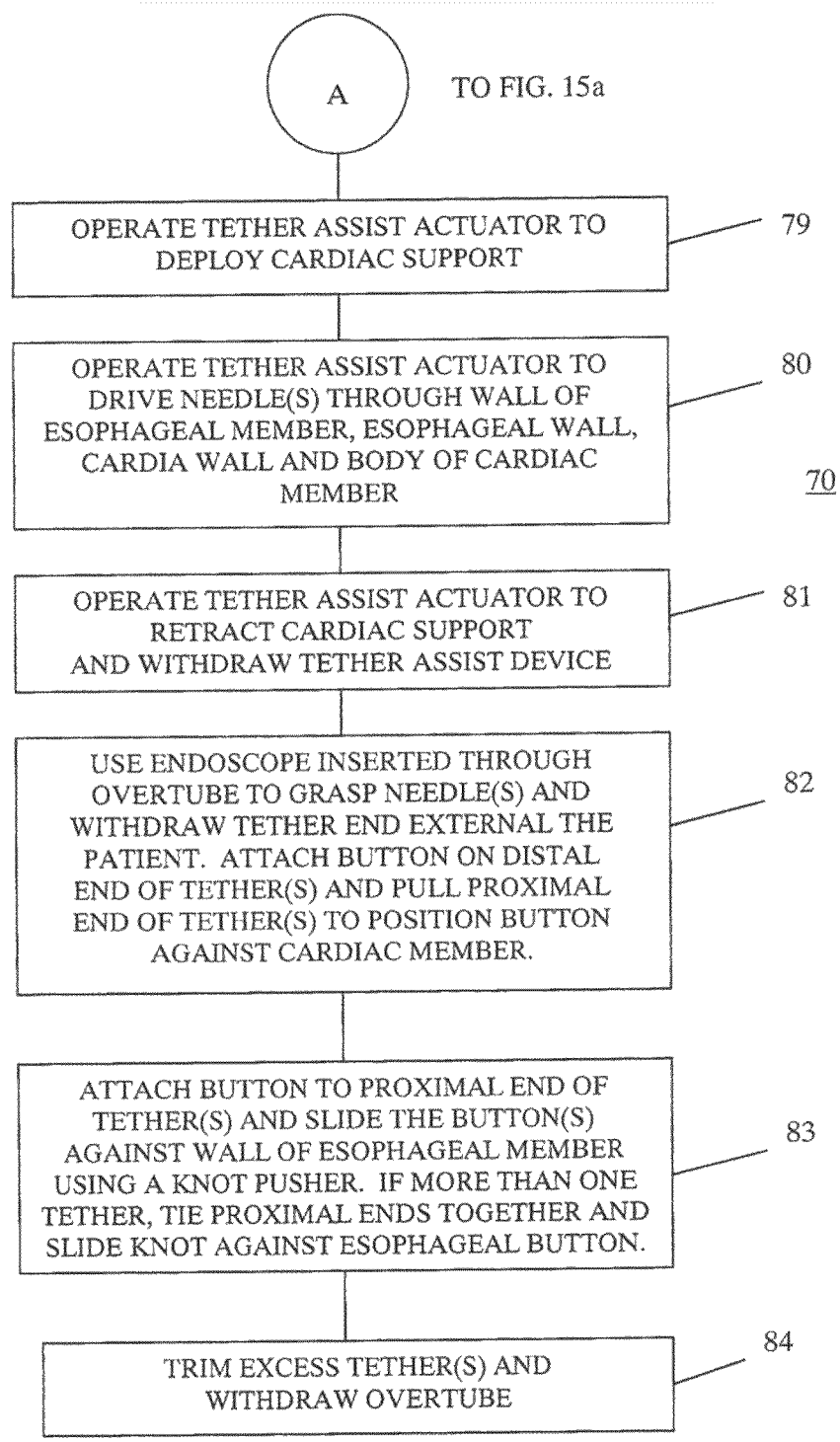

A bariatric device deployment procedure 70 may be used to deploy bariatric device 10 (FIGS. 15a and 15b). Deployment procedure 70 begins at 71, with the recipient sedated or anesthetized, by performing an esophageal gastroduodenoscopy (EGD) to inspect the recipient's esophagus and stomach and to pass a conventional EGD wire through an EGD scope into the stomach (72). The physician may inject contrast die at one side of the GE junction in order to assist in fluoroscopic visualization and the placement of the bariatric device. The EGD scope is removed and the wire is left in the recipient's esophagus.

Figure 17:
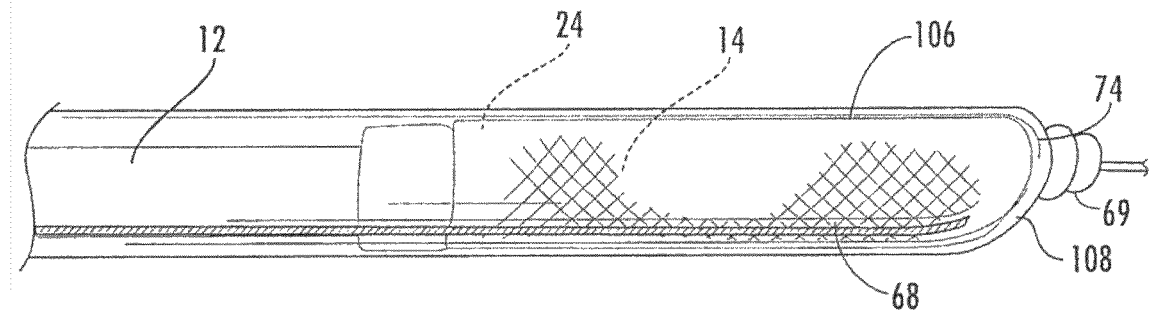
FIG. 17 is a perspective view of a bariatric device deployment member.

The wire may be used to pass a lubricated deployment device 74, as seen in FIG. 17, into the stomach utilizing fluoroscopy (73). The wire may be removed. The cardiac member is deployed distally at 75 utilizing a pusher inserted within deployment device 74. Because of the nature of the cardiac member, it will unfold once it is clear of the deployment device. The physician can use a marker 68 on the deployment device to align the bariatric device by rotation of the device until marker 68 is appropriately positioned. Alternately, the physician could rotate the device until tension member 24 either aligns with or is opposite the contrast die mark. With the cardiac device deployed in the stomach, the physician pulls back on the deployment device 74, which pulls the cardiac member against the cardia and deploys the esophageal member from the deployment device. The deployment device is then removed from the recipient (75).

A conventional overtube may be positioned over a conventional endoscope and deployed in the recipient's esophagus distally to the proximal end of esophageal member 12 (76). The overtube provides a pathway to the bariatric device to allow completion of deployment while minimizing risk of damage to the recipient's esophagus.

A tether assist device 86 (FIGS. 18 and 19) may be inserted through the overtube at 78. The tether assist device includes a cardiac support 90 that is deployed in a manner which will be described in more detail below (79). The tether assist device is actuated to drive needles connected with the tether filament through the wall 18 of the esophageal member, the wall of the recipient's esophagus, the wall of the recipient's stomach at the cardia, and body 21 of the cardiac member (80). The cardiac support is then retracted and the tether assist device is withdrawn at 81.

The distal end(s) of the tether filament(s) may be secured against the surface of cardiac member body 21 opposite the cardiac surface 22 by applying a proximal force to the tether until integral tether clamp 42 is against body 21 of the cardiac member. If a separate distal tether clamp is applied in situ, this may be accomplished by inserting an endoscope E through the overtube and through the esophageal member into the recipient's stomach to grasp and withdraw the tether end(s) external to the recipient (82). Alternatively, tether assist device 86 may retain the tether distal end(s) with the cardiac support so that withdrawal of the tether assist device also withdraws the tether end(s) external to the recipient. A tether clamp, such as a button 98, (FIGS. 23 and 25) may be fixed to the distal end of the tether filament(s) and the proximal end of the tether filament(s) pulled in order to position the tether clamp against the cardiac member (82). Another tether clamp, such as a button 98 may be attached to the proximal end of the tether(s), such as by a slipknot, as will be described in more detail below, and the clamp slid against the wall of the esophageal member, such as by using a knot pusher (83). The knot pusher may have a tapered end to ensure that the button may be pushed entirely against the wall of the esophageal member. Optionally, if more than one tether filament is used, the physician may tie the proximal ends of the tether filaments together and, using a knot pusher, slide the knot against the tether clamp at the esophagus. Excess tether filament may be trimmed and the overtube withdrawn at 84.

Figure 16A:
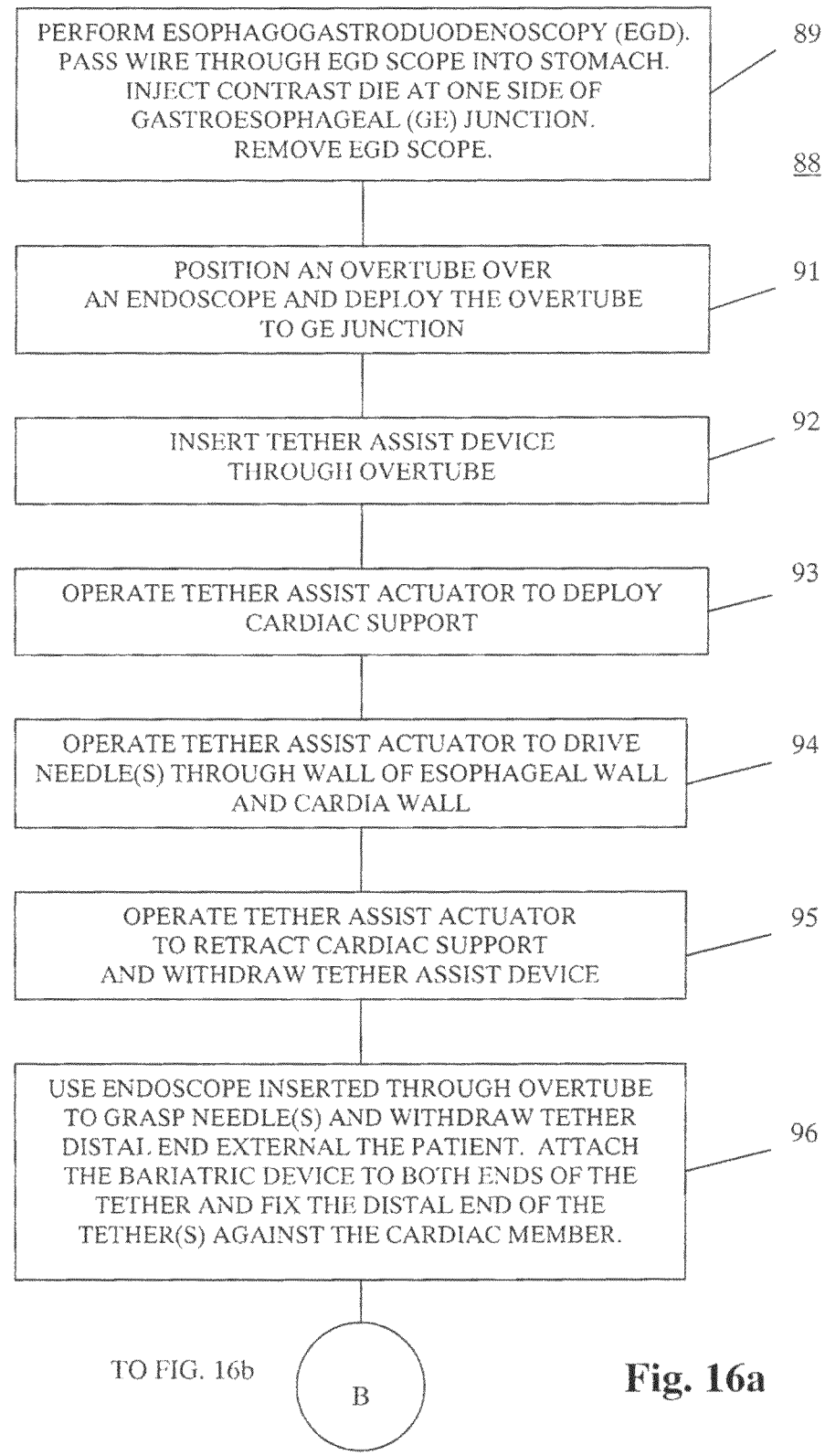
FIGS. 16a and 16b are a flowchart of an alternative procedure for deployment of a bariatric device.
Figure 16B:
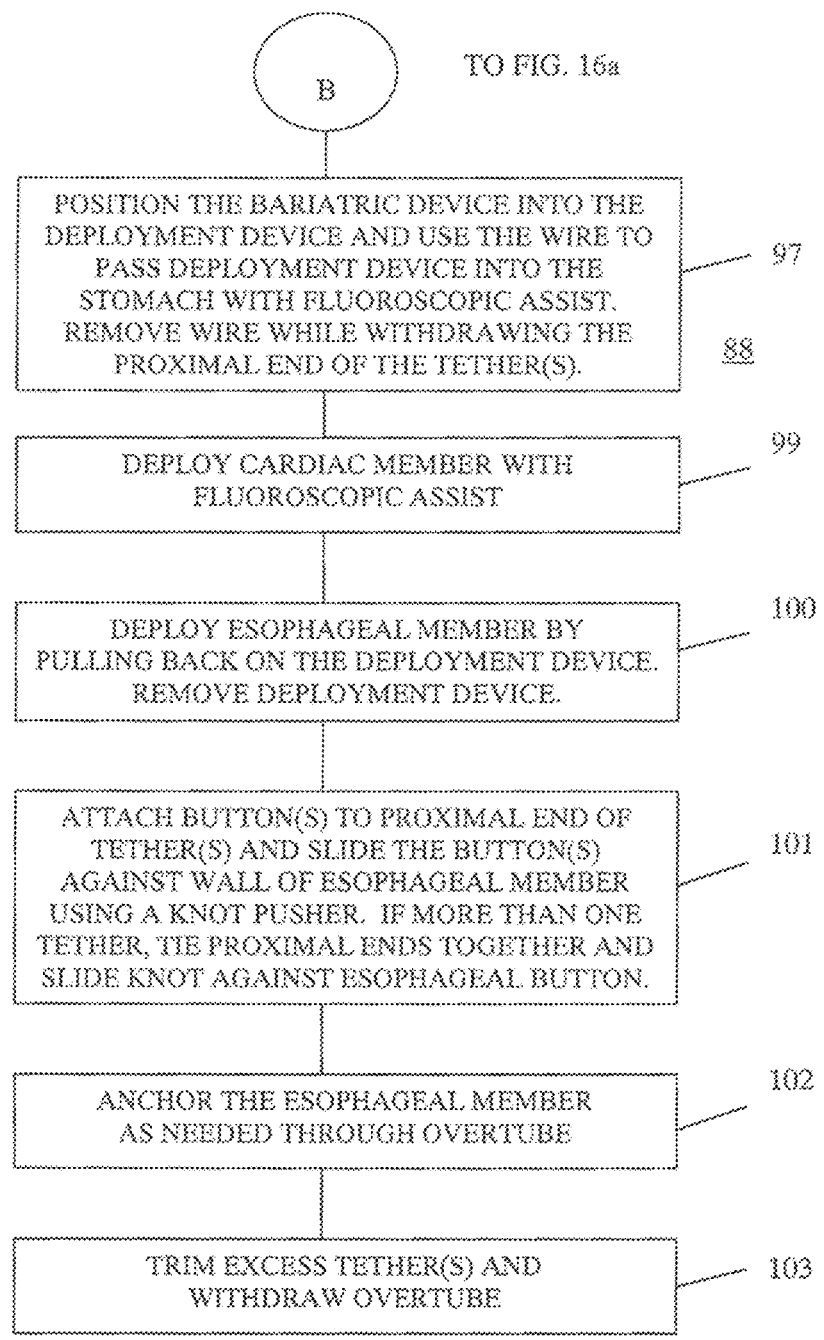

In an alternative embodiment (FIGS. 16a and 16b), in which the tether(s) is positioned in the recipient before the bariatric device is deployed, a bariatric device deployment procedure 88 begins with an EGD being performed (89) and an overtube being positioned over an endoscope and deployed to the proximal to the GE junction (91). The tether assist device is inserted through the overtube (92) and operated to deploy the cardiac support (93). The tether assist device is then operated at 94 to drive the needle(s) through the walls of the esophagus and the cardia. The tether assist actuator is operated at 95 to retract the cardiac support and to withdraw the tether assist device.

The tether needle(s) are withdrawn through the overtube to a location external the recipient (96). The bariatric device may be affixed to both ends of the tether(s). In particular, the proximal end of the tethers is inserted through openings in the esophageal member. The distal ends of the tether(s) are passed through the cardiac member and affixed to the cardiac member, such as using a button 98 as previously described. The bariatric device may then be positioned in the deployment device at 97 and the wire is used to pass the deployment device into the stomach with fluoroscopic assist. While the bariatric device is being deployed to the stomach, the physician takes up slack in the tether(s) by pulling on the proximal ends thereof.

The cardiac member is deployed (99) and the esophageal member is deployed (100) in a manner similar to that previously described. When slack is removed from the tether(s), the physician may attach a button to the proximal end of the tether(s) at 101 and slides the button(s) against the wall of the esophageal member, such as using a knot pusher. Appropriate tension is applied. If more than one tether is used, the physician may optionally tie the proximal ends together and slide the knot against the esophageal button. The esophageal member may then be anchored (102), as previously described, and excess tether material trimmed (103). Although two (2) tethers are illustrated, one or more than two may be used. If more than two tethers are used, they can be attached to the esophageal member and the cardiac member in a manner that distributes the force both laterally and longitudinally on each member.

Thus, it is seen that bariatric device deployment procedure 70, 88 is minimally invasive and can be performed transorally utilizing many tools that are conventionally used for EGD and endoscopy. The deployment procedure can be performed in a relatively short time, on the order of magnitude of the time required for an endoscopy, colonoscopy, or the like, such as less than one hour and even less than half an hour or less. Because the recipient is sedated, or minimally anesthetized, the recipient should tolerate the procedure much better than a more invasive procedure, such as gastric bypass surgery or other bariatric surgery. It should be understood, however, that bariatric device 10 can be deployed utilizing other techniques. For example, tethers 26 can be deployed utilizing a combination of laparoscopic and endoscopic procedures carried out with conventional instruments, rather than utilizing the tether assist device disclosed herein.

Deployment device 74 includes a tubular member 106 which may have a wall made of 1/32 inch PTFE with a cross section that is smaller than the recipient's esophagus, such as 11/16 inch outer diameter, and having a tapered distal end 108 to reduce a tendency to snare the esophagus while being inserted (FIG. 17). Bariatric device 10 may be folded with cardiac member 14 rolled and esophageal member 12 radially compressed. Tension member 24 may be flexed to position the esophageal and cardiac members in the deployment device in the position illustrated in FIG. 11. A balloon 69 may be inserted in the deployment device and inflated to further enhance the smooth contours of the delivery system. During deployment, tubular member 106 is lubricated and, as previously described, inserted into the stomach over a previously placed wire and guided using fluoroscopy. Once in position, balloon 69 can be deflated and the cardiac member may be deployed by an instrument inserted into the proximal end of the tubular member until the cardiac member exits the tube, at which time it will unravel to its deployed position. With the physician moving the deployment device proximally, the cardiac surface 22 will be moved into contact with the cardia and the esophageal member will begin to be deployed out the distal end of tubular member 106. Further proximal motion of the tubular member will fully deploy the esophageal member in the esophagus. Should it be desired to reposition the bariatric device, the physician can insert an overtube into the esophagus in a conventional manner, such as over an endoscope, and grasp a proximal end of cage 44, 144, 144' in order to reduce the diameter of the cage and position the overtube over the esophageal member 12. The bariatric device can then be rotated or, otherwise, moved and redeployed out of the end of the overtube.

Other deployment devices may be utilized. For example, rather than being confined within a tubular deployment tool, the bariatric device esophageal member and cardiac member may be compressed and retained in a compressed state by a cord wound around the members. Once in position, the cord can be removed from around each of the members by pulling on a cord to deploy that member, which then assumes its expanded state. Alternatively, the bariatric device members could be compressed at their respective positions on the tether assist device, with the cardiac member compressed about cardiac support 93 and the esophageal member compressed about the shaft of the tether assist device. In this manner, both the bariatric device and the tether assist device can be deployed simultaneously through an over-tube and the bariatric device expanded in the proper orientation to the tether assist device by pulling on the cord. This allows the physician to orient the bariatric device in the recipient by orienting the tether assist device.

One or more lines 66a, 66b, may be attached to the esophageal member and extend proximally outside the recipient to allow the physician to snug the bariatric device against the cardiac portion of the stomach. Another line 66c may be attached to cardiac member 21 and extend proximally through the esophageal member external the recipient. Line 66c allows the physician to position cardiac member 21 laterally and to hold it in place while the tethers are being applied. Lines 66a-66b may be made from sutures and may be color-coded. Once bariatric device 10 is fully deployed, lines 66a, 66b are severed at the device using endoscopic scissors, or the like.

While the tether clamp for the distal end of the tether(s) can be secured to the tether(s) external the recipient and drawn into position against the cardiac member or can be a fastener integrally formed with the distal end of the tether and driven to position by the tether tool, the proximal end of the tether(s) may be secured by a tether clamp 98 external the recipient and slid into engagement with the inner wall of the esophageal member along the tether filament once the bariatric device is deployed.

Figure 21:
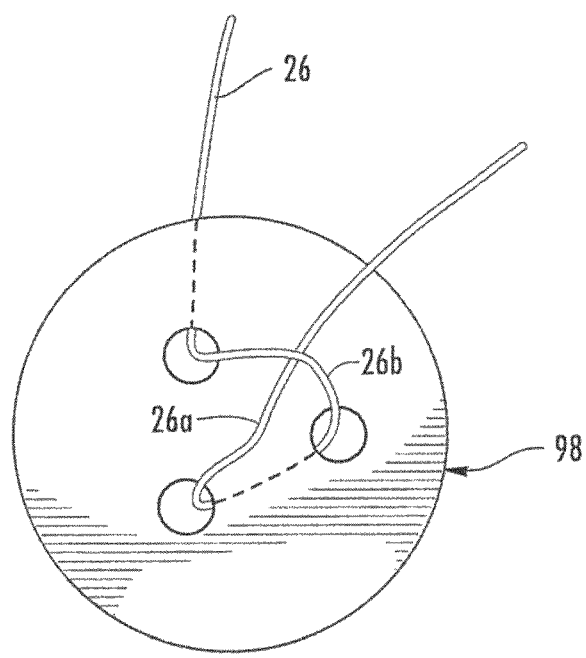
FIG. 21 is the same view as FIG. 19 illustrated with a tether.
Figure 22:
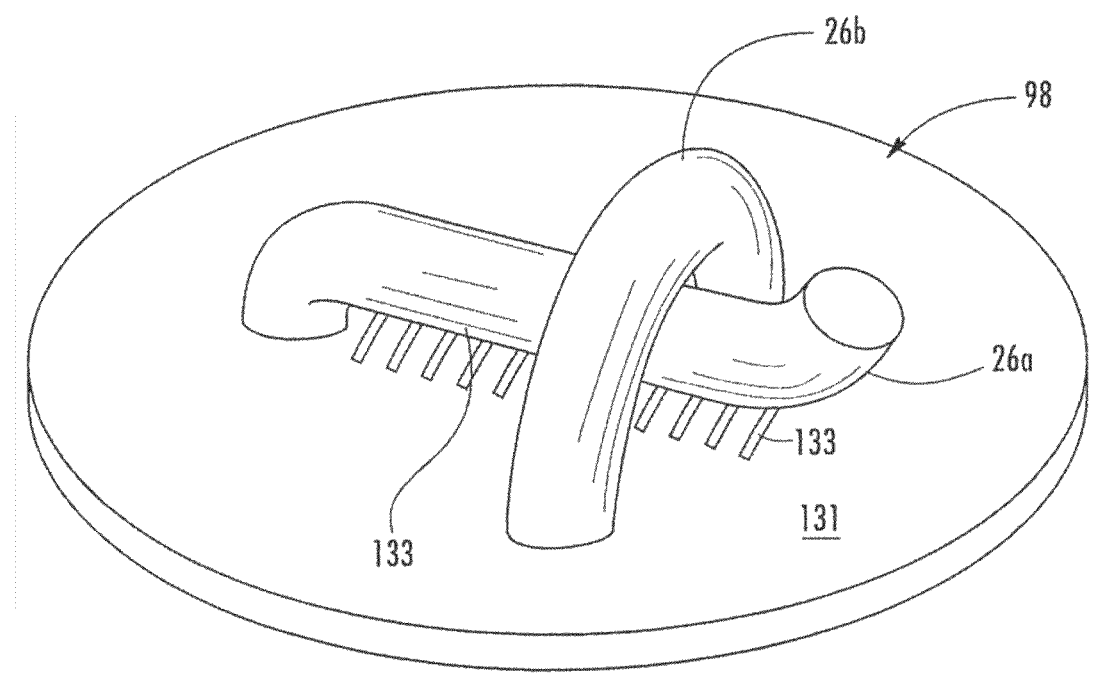
FIG. 22 is an enlarged perspective view of the tether clamp device of FIGS. 19 and 20.
Figure 23:
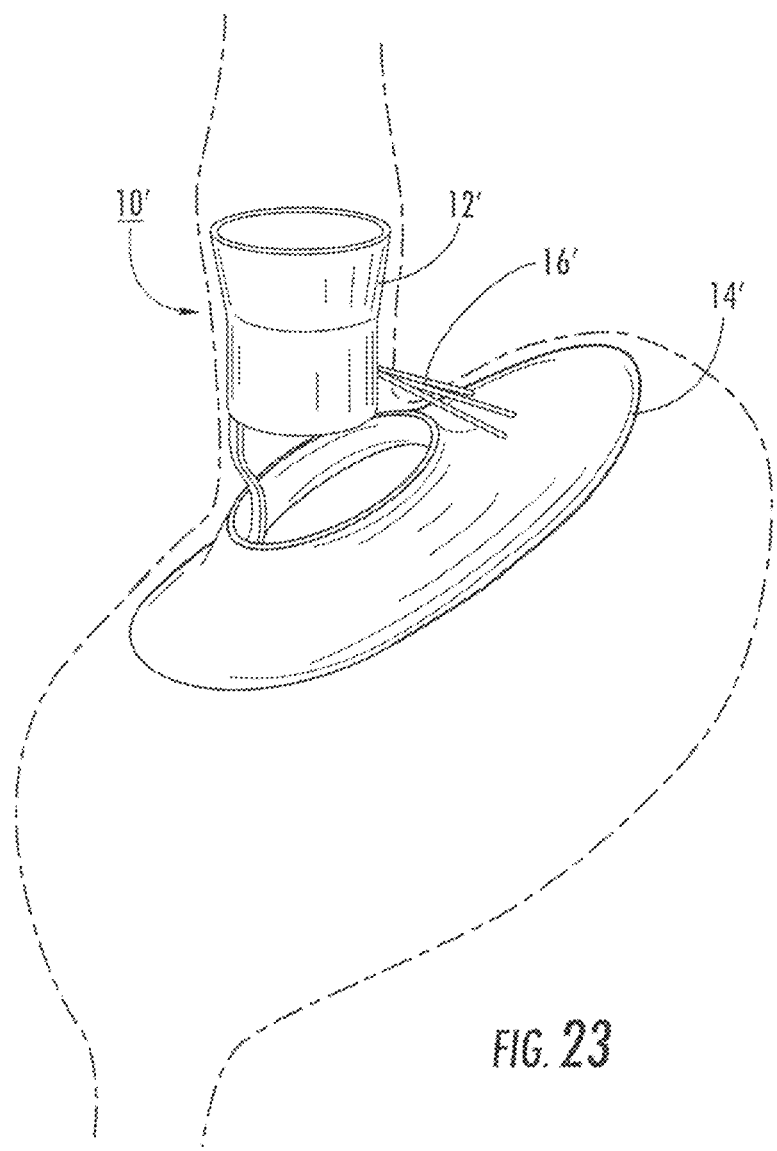
FIG. 23 is a perspective view of an alternative embodiment of a bariatric device deployed in a recipient.
Figure 24:
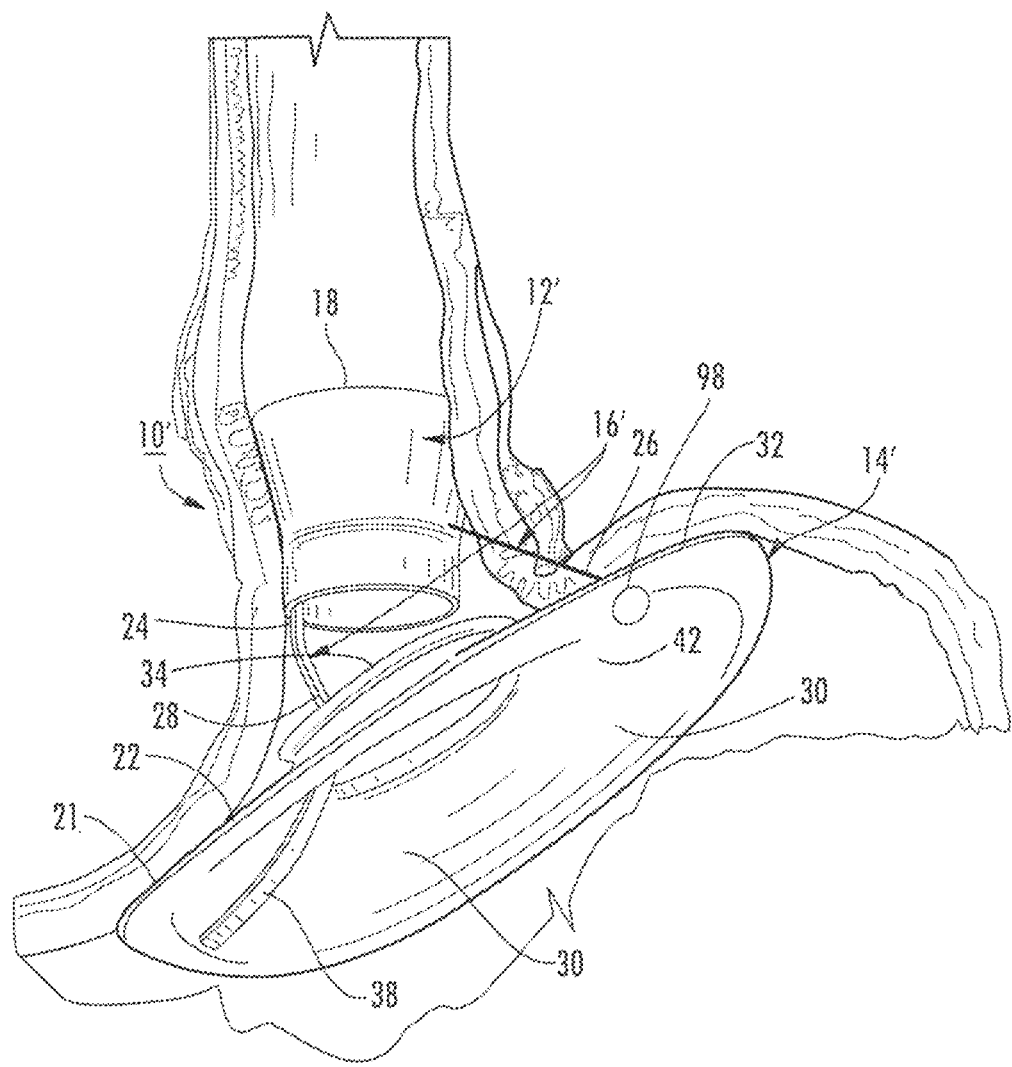
FIG. 24 is a perspective view of the bariatric device illustrated in FIG. 23 taken from a side and distal direction.
Figure 25:
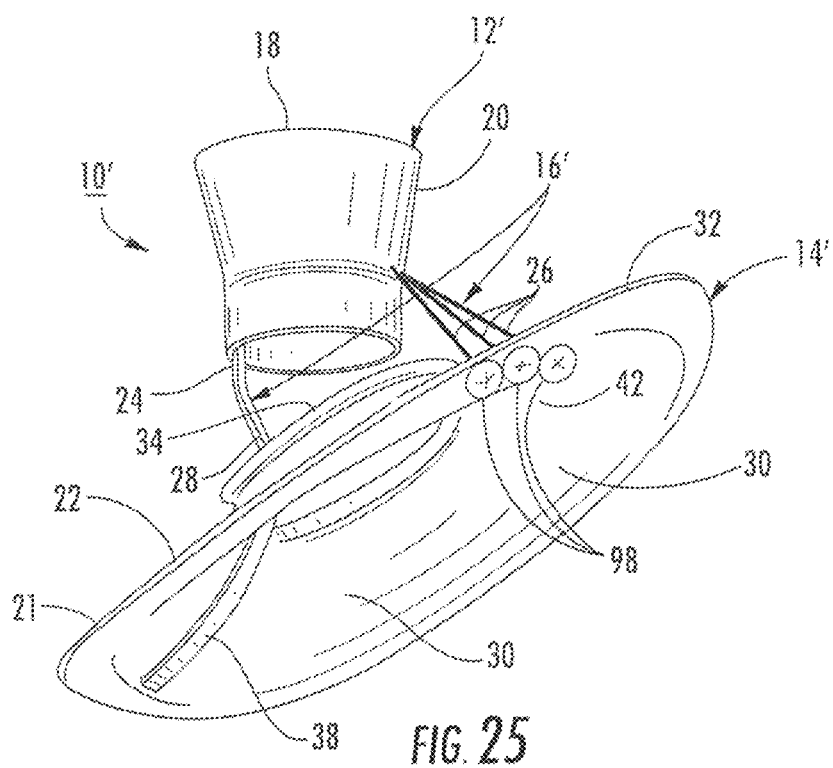
FIG. 25 is a perspective view of the bariatric device in FIG. 23 illustrating additional detail thereof.
Figure 26:
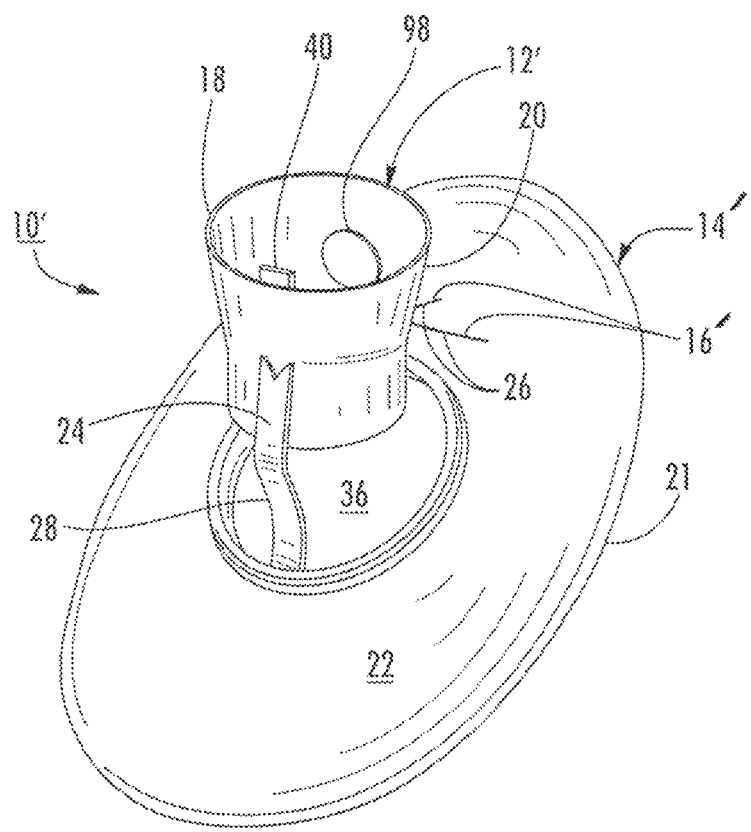
FIG. 26 is a perspective view of the bariatric device in FIGS. 22 through 24 illustrating additional details thereof.

In the illustrative embodiment, the tether clamp may be a button 98 in the form of a disk 130 containing a plurality, such as three (3), through-openings 132. Disk 130 may be made of a suitable material, such as polycarbonate, or the like. As illustrated in FIGS. 21 and 22, tether clamp 98 is attached to the proximal end of the tether by passing an end 26a of the tether under a loop 26b formed by the tether thereby forming a one-way clamp that operates similarly to a slipknot. This allows the tether clamp to be propelled along the tether from external the recipient to a position engaging the inner wall of the esophageal member and snugged up to a desired tension of the tether, using a conventional knot pusher, or the like. Although the tether clamp can move relatively freely in one direction for deployment, it resists movement in the other direction, thereby firmly engaging the inner wall of the esophageal member or cardiac member. A roughened portion 133 of the surface 131 of disk 130 may be provided to help lock the tether to resist movement of tether clamp 98. Also, an elongated extension of surface 131 (not shown) may be provided on either side of opening 132 to trap or pinch the end 26a of the tether. Tether clamp 98 causes tension between the esophageal member and the cardiac member via the tether, thereby both engaging the cardiac surface with the cardiac region of the stomach in order to activate receptors in the cardia, as well as to assist in anchoring bariatric device 10 in place. For additional stability, the physician may choose to tie a slipknot to the ends, if more than one tether is used, and slide the slipknot against the buttons 98 within the esophageal member using a knot pusher. The ends of the tether are trimmed and removed. The overtube can then be removed.

Once deployed, bariatric device 10 may be removed by inserting a conventional overtube in the esophagus and using endoscopic scissors, laparoscopic scissors, or the like, to clip the tether(s). The proximal portion of the esophageal member may be grasped, such as with a conventional grasping tool and pulled proximally. This reduces the diameter of the esophageal member allowing the esophageal member to fit within an overtube. The overtube may be moved distally around the esophageal member, thereby protecting the esophagus and GE junction as the remainder of the bariatric device is retrieved through the overtube. The entire overtube may then be removed, completing the removal procedure. If tissue apposition is used, a conventional ablation procedure may be used to remove the ingrown tissue, such as mucosa, to allow the bariatric device to be moved. Alternatively, bariatric device 10 may be made from bioabsorbable material and absorbed in the recipient's body.

Because of the use of the tether(s) and tissue ingrowth for anchoring, bariatric device 10 may be left in place for many months and even a year or longer. Because bariatric device 10 can be deployed for longer than just a few weeks, morbidly obese recipients can use bariatric device 10 to lose all or most of their excess bodyweight. The recipient may be provided with nutritional counseling in order to develop healthier eating habits during the period of satiety induced by bariatric device 10. Tension on the tether(s) and/or tension may be adjusted after deployment as needed to titrate the amount and rate of weight loss. Tension on the tether may be increased by sliding button 98 while grasping the tether or may be reduced by loosening or replacing the tether. As with any weight loss regiment, recipient's medications should be adjusted to account for the weight loss.

Although illustrated for use in deployment of bariatric device 10, tether clamps 98 may find other applications. Examples of such other applications include closure of fistulas, tightening of anastomosis, closure of leaks, tightening of a gastric pouch and closure of a gastrotomy. Other applications will be apparent to the skilled artisan.

An alternative embodiment of a bariatric device 10' includes an esophageal member 12' having a conically shaped proximal portion and a cardiac member 14' (FIGS. 23-26). Bariatric device 10' includes a connector 16' made up of a tension member 24 and a plurality of tethers 26. Tethers 26 are radially spaced apart in order to provide additional upward pressure on the cardiac member. Also, the force acting on each tether is reduced in order to reduce the likelihood of breakage and to provide redundancy should one of the tethers break.

Figure 32:
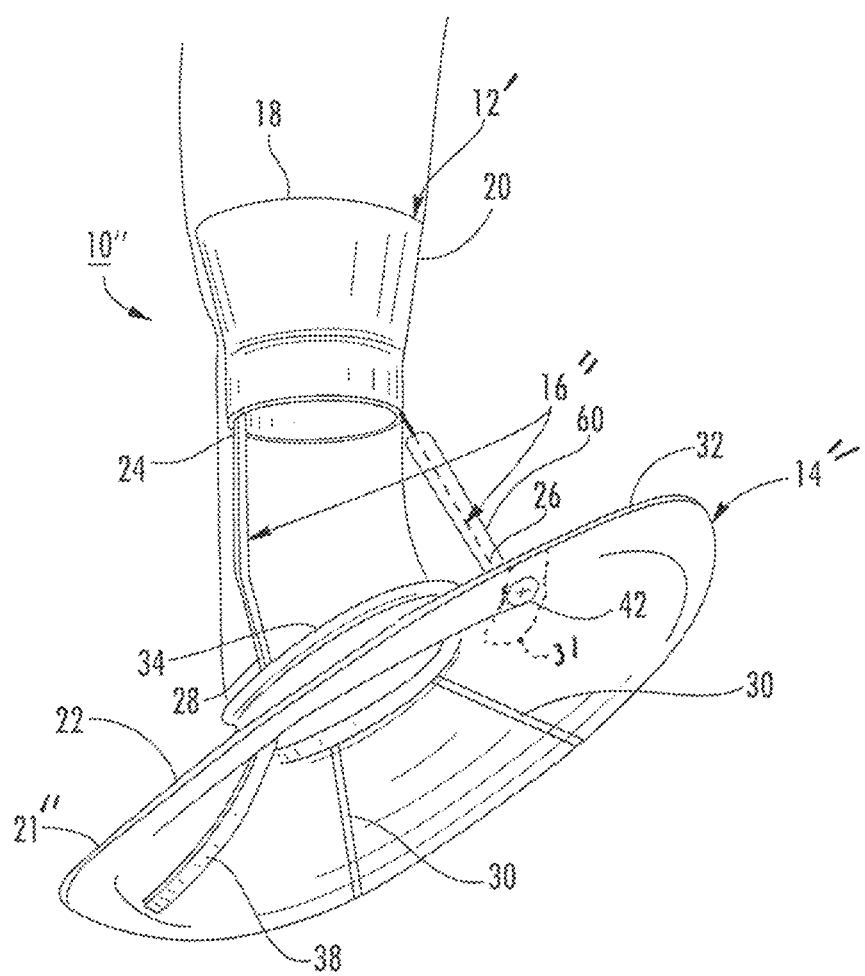
FIG. 32 is a perspective view of an alternative embodiment of a bariatric device.
Figure 33:
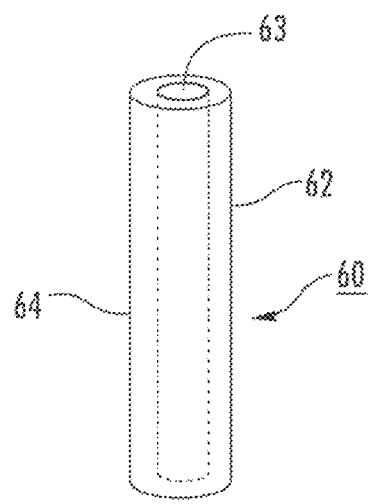
FIG. 33 is an elevation of a connector used with the bariatric device of FIG. 32.

An alternative embodiment of a bariatric device 10" may include a connector 16" having a tension member 24 and a tether 26 including an anchor 60. Anchor 60 may be made up of an elongated member 62 having an outer surface 64 that is configured to promote tissue attachment, tissue ingrowth and/or mucosal capture (FIGS. 32 and 33). Examples of such surface configuration are disclosed in commonly assigned International Patent Application Publication No. WO 06/044640A1, entitled BARIATRIC DEVICE AND METHOD and in commonly assigned provisional patent application Ser. Nos. 60/901,457 and 60/921,930 entitled BARIATRIC DEVICE AND METHOD by Baker et al., the disclosures of which are hereby incorporated herein by reference. Anchor 60 extends from the lower esophagus to the cardiac region of the stomach through a passage extending outward of the GE junction. As previously described, this allows normal functioning of the GE junction. Elongated member 62 has a through-opening, or lumen 63, that facilitates passage of tether 26. This ensures that the tether will not experience lateral migration. Also, the tether may be allowed to move longitudinally to provide adjustability to the strain exerted by the esophageal and/or cardiac portions. Bariatric device 10" also includes a cardiac member 14" having a plurality of ribs 30 that are spaced radially about body 21" in order to impart additional stiffness to body 21" if desired. Also, body 21" may include a surface feature 31 that is recessed to the approximate footprint of cardiac member support 90 to enhance engagement of support 90 with body 21" during tether deployment In use, anchor 60 can be positioned by the physician either as part of the procedure to deploy bariatric device 10". Alternatively, anchor 60 can be positioned several weeks before placement of the rest of the device. This allows time for tissue ingrowth to take place to firmly hold the anchor in place. When the rest of the device is subsequently positioned, the physician can rely on the anchor being firmly positioned.

Figure 34:
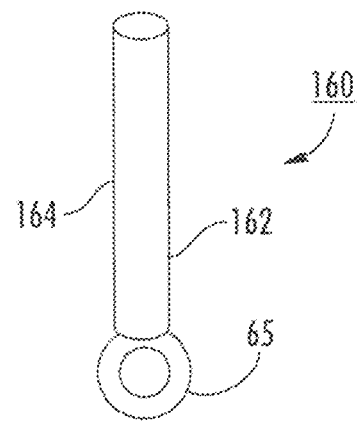
FIG. 34 is the same view as FIG. 33 of an alternative embodiment thereof.

In another embodiment, an anchor 160 includes an elongated member 162 having an outer surface 164 that is configured to promote tissue attachment, tissue ingrowth and/or mucosal capture (FIG. 34). Anchor 160 further includes one or more attachment mechanisms 65, which is illustrated as a loop but may be other configuration that allows attachment to elongated member 162, such as by a fastener, or the like. Anchor 160 is illustrated without a lumen but may have one depending upon the application. With one or more anchors 160 positioned in the manner previously described, it may serve as a mechanism for attachment of a cardiac portion. The anchor(s) allow strain to be placed on the cardiac region of the stomach by a fastening system between the cardiac portion and the attachment mechanism 65. This facilitates a bariatric device having primarily only a cardiac member. Because the bariatric device does not pass at all through the GE junction, there is no interference with normal function of the GE junction. Also, there is no need for engagement with the esophagus.

While described as applying an outward force on the cardiac portion of the stomach, the bariatric device may, alternatively, apply an inward force on the cardia as would be apparent to the skilled artisan. This may be accomplished in various fashions, such as by providing tissue attachment, tissue ingrowth and/or mucosal capture openings on the cardiac member.

Figure 35:
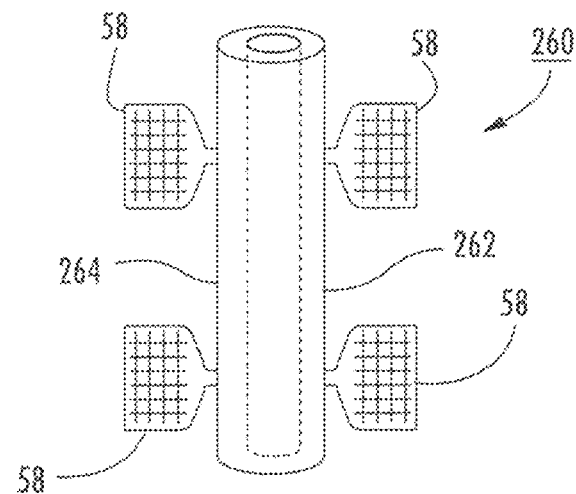
FIG. 35 is the same view as FIG. 33 of another alternative embodiment thereof.

In another embodiment, an anchor 260 includes an elongated member 262 having one or more appendages 58 extending from an outer surface 264 (FIG. 35). Appendages 58 are configured to promote tissue attachment, tissue ingrowth and/or mucosal capture. This allows appendages 58 to become firmly attached in the wall of the stomach and/or esophagus, thus retaining anchor 260. Outer surface 264 may optionally include tissue attachment, tissue ingrowth and/or mucosal capture openings.

Figure 36:
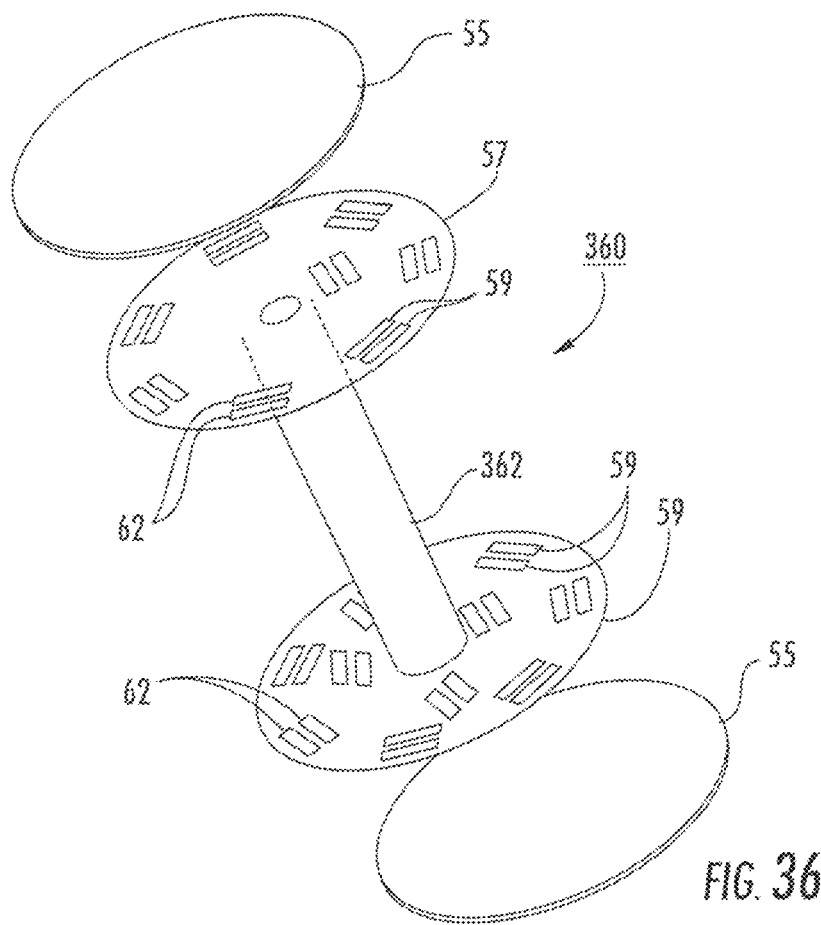
FIG. 36 is the same view as FIG. 33 of yet another alternative embodiment thereof.

In yet another embodiment, an anchor 360 includes an elongated member 362 having plates 57 at one or more ends of the elongated member (FIG. 36). Each plate 57 includes mucosal capture openings 59. The mucosal capture openings may be evenly spaced or may be in pairs to promote mucosal bridging. Once anchor 360 is positioned, the mucosa of the esophagus bulges the openings 59 of one plate 57 and the mucosa of the stomach bulges the openings 59 of the other plate 57. This mucosal capture provides a more rapid retaining of anchor 360 in position as disclosed in the '457 and '930 provisional patent applications. The mucosal capture can be expedited by using agents to promote scaring together of the mucosal portions across the bridge, such as by fibrosis growth. In the illustrated embodiment, a retainer, such as a cap, 55 may be provided to fit over each plate 57 after the mucosa enters openings 62. This applies a pressure on the mucosa to retain the mucosa and may further force the mucosa together to stimulate bridging together of the mucosa. Caps 55 can be retained on plate 57, such as by snap fit or other known techniques.

Anchor 360 may be removable. This is accomplished because the captured mucosa can be removed, such as by ablation, chemical cautery, ultrasound, laser, or the like. One or both plates 57 can be made removable from elongated member 362. This allows anchor 360 to be removable and, hence, the method reversible notwithstanding the use of mucosal capture.

Figure 37:
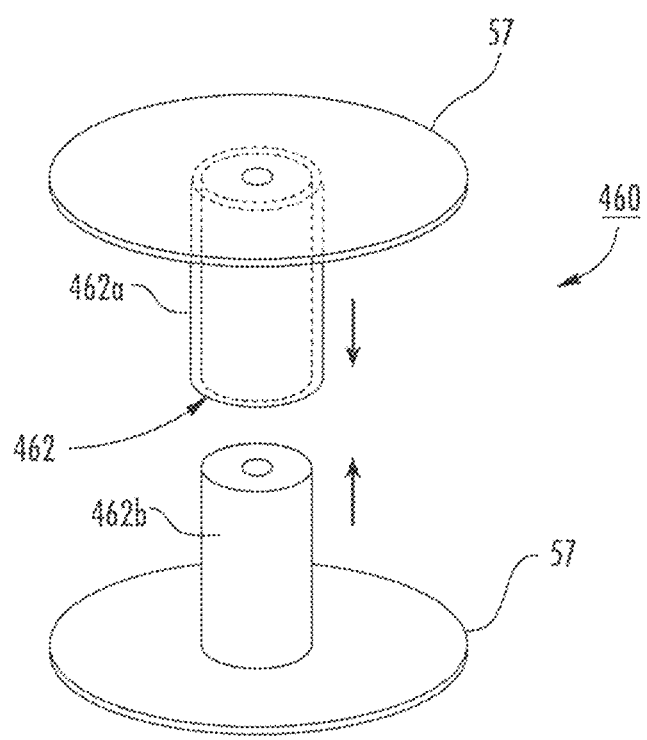
FIG. 37 is the same view as FIG. 33 of yet another alternative embodiment thereof.

In another alternative embodiment, an anchor 460 has an elongated member 462 made of complementary sections 462a and 462b (FIG. 37). These sections snap together in a lengthwise adjustable fashion, such that one section may be inserted from the esophagus and one section from the stomach. Once engaged, further pressure causes a snap retention of the sections together to a desired length. Optionally, the length may be elongatable as well. Each section 642a and 642b may include a plate 57 or an attachment mechanism (not shown).

Figure 38:
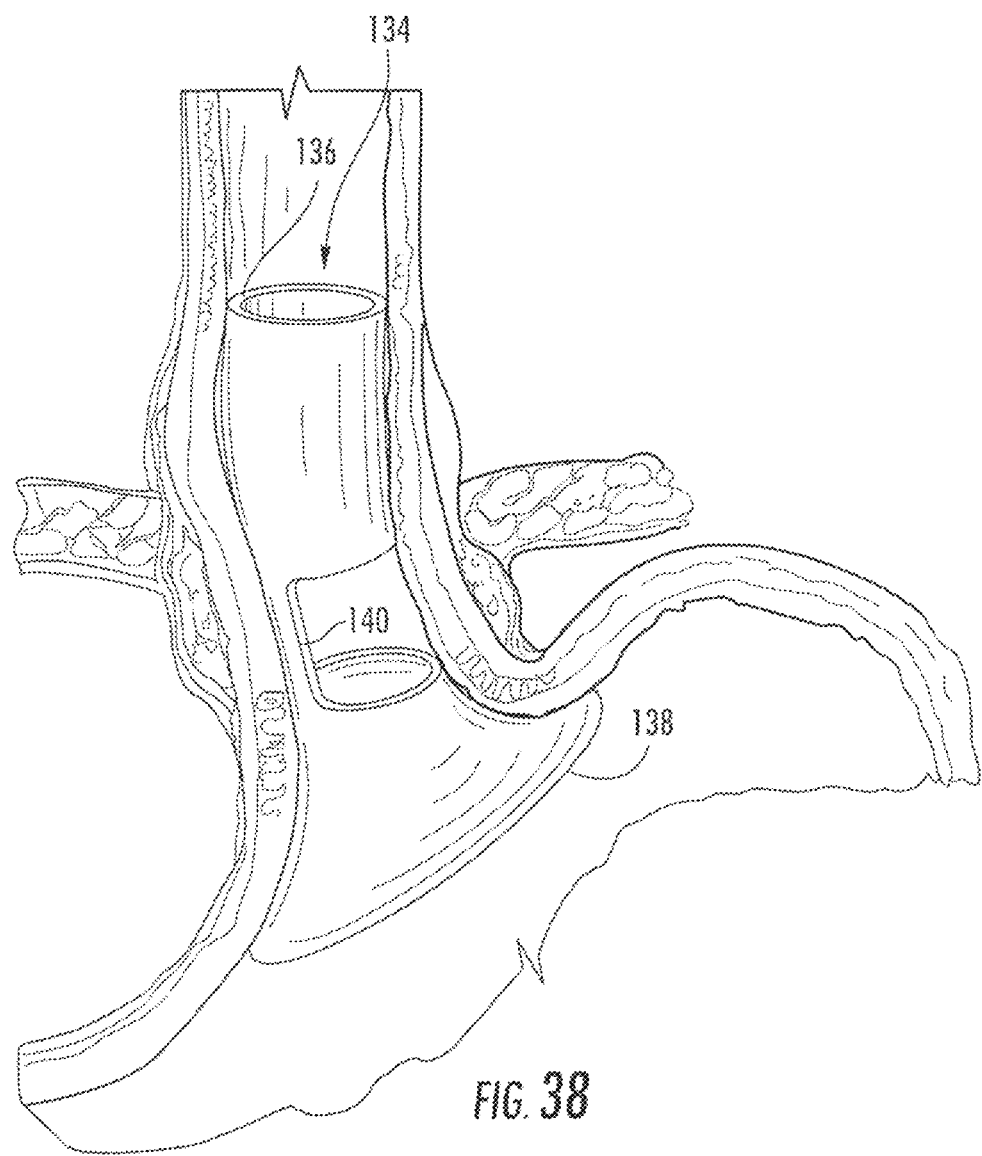
FIG. 38 is a perspective view of another alternative embodiment of a bariatric device.

An alternative bariatric device 134 includes an esophageal member 136, a cardiac member 138 and a connector 140 (FIG. 38). In bariatric device 134, connector 140 is a strap that is sufficiently rigid to properly position cardiac member 138 against the cardia without the requirement for a tether or other connecting member. However, a tether may also be used.

Figure 39:
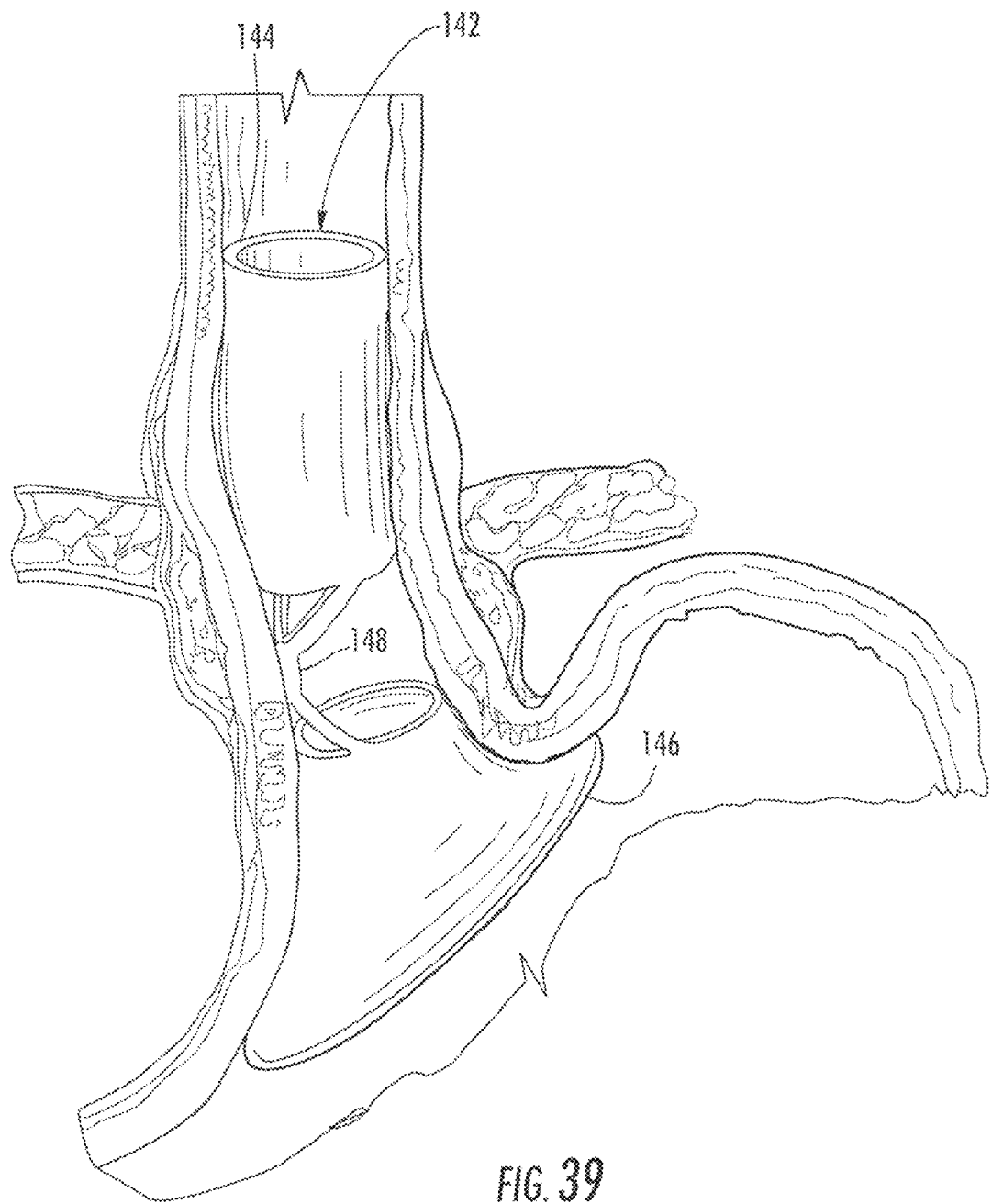
FIG. 39 is a perspective view of another alternative embodiment of a bariatric device.

An alternative bariatric device 142 includes an esophageal member 144, a cardiac member 146, and a connector 148 (FIG. 39). Connector 148 is X-shaped with the center of the X positioned at the pseudo-sphincter of the GE junction. This allows the tension force to be distributed around more of the circumference of the esophageal member 144 and the cardiac member 146. As with bariatric device 134, the connector 148 for bariatric device 142 is a single-strap assembly that may be used with or without the use of a tether.

Figure 40:
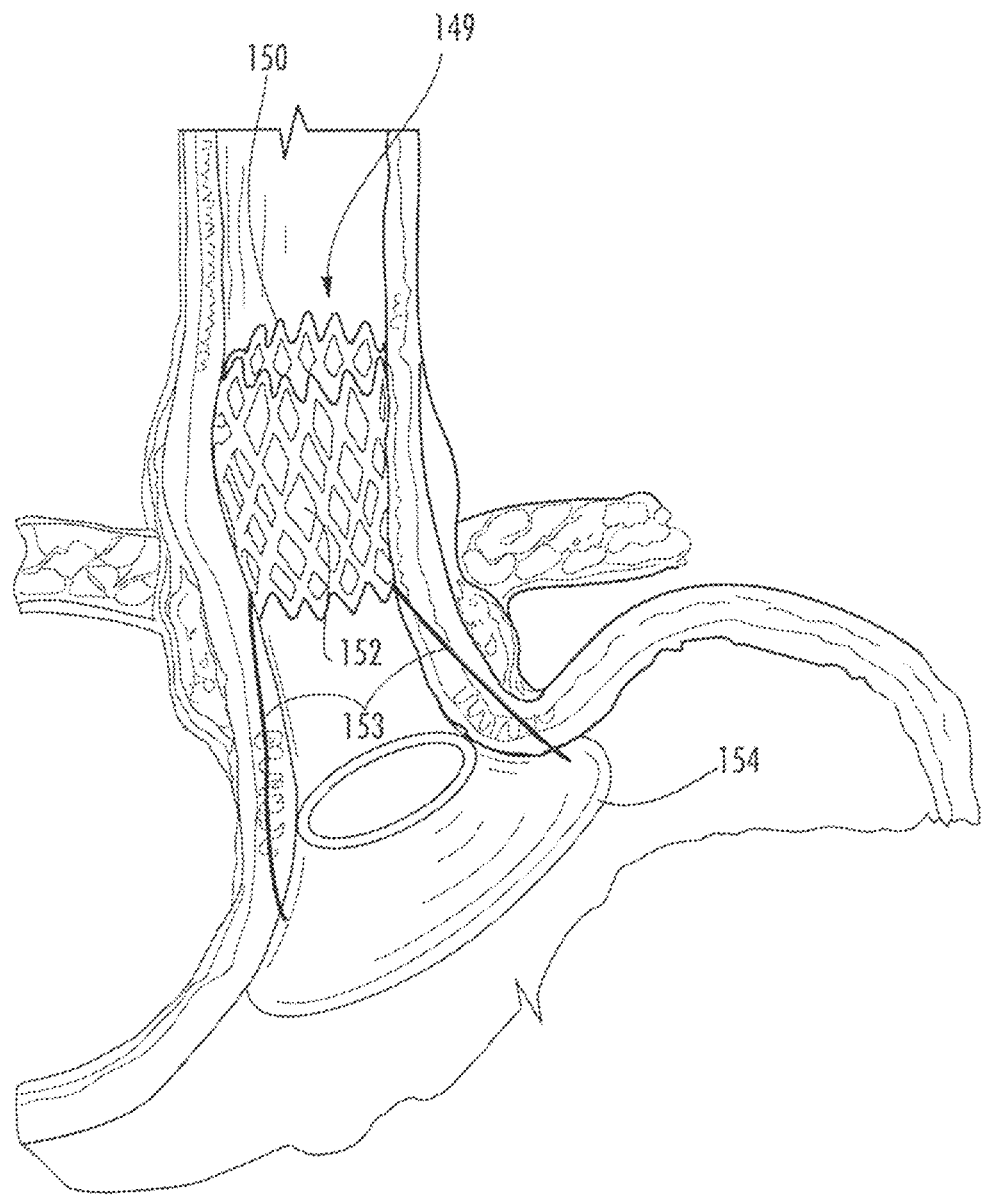
FIG. 40 s a perspective view of another alternative embodiment of a bariatric device.

An alternative bariatric device 149 includes an esophageal member 150 and a cardiac member 154 (FIG. 40). Esophageal member 150 may include tissue ingrowth openings 152 distributed along substantially the entire surface of the wall defining the esophageal member. This promotes tissue ingrowth along substantially the entire inner surface of the esophageal member. Bariatric device 149 includes a connector made up of two or more tethers 153 placed opposite each other across the GE junction. The tethers pass external the GE junction and allow substantially unrestrained operation of the pseudo-sphincter. Although only two tethers 153 are illustrated, more may be used and distributed around the GE junction.

Figure 41:
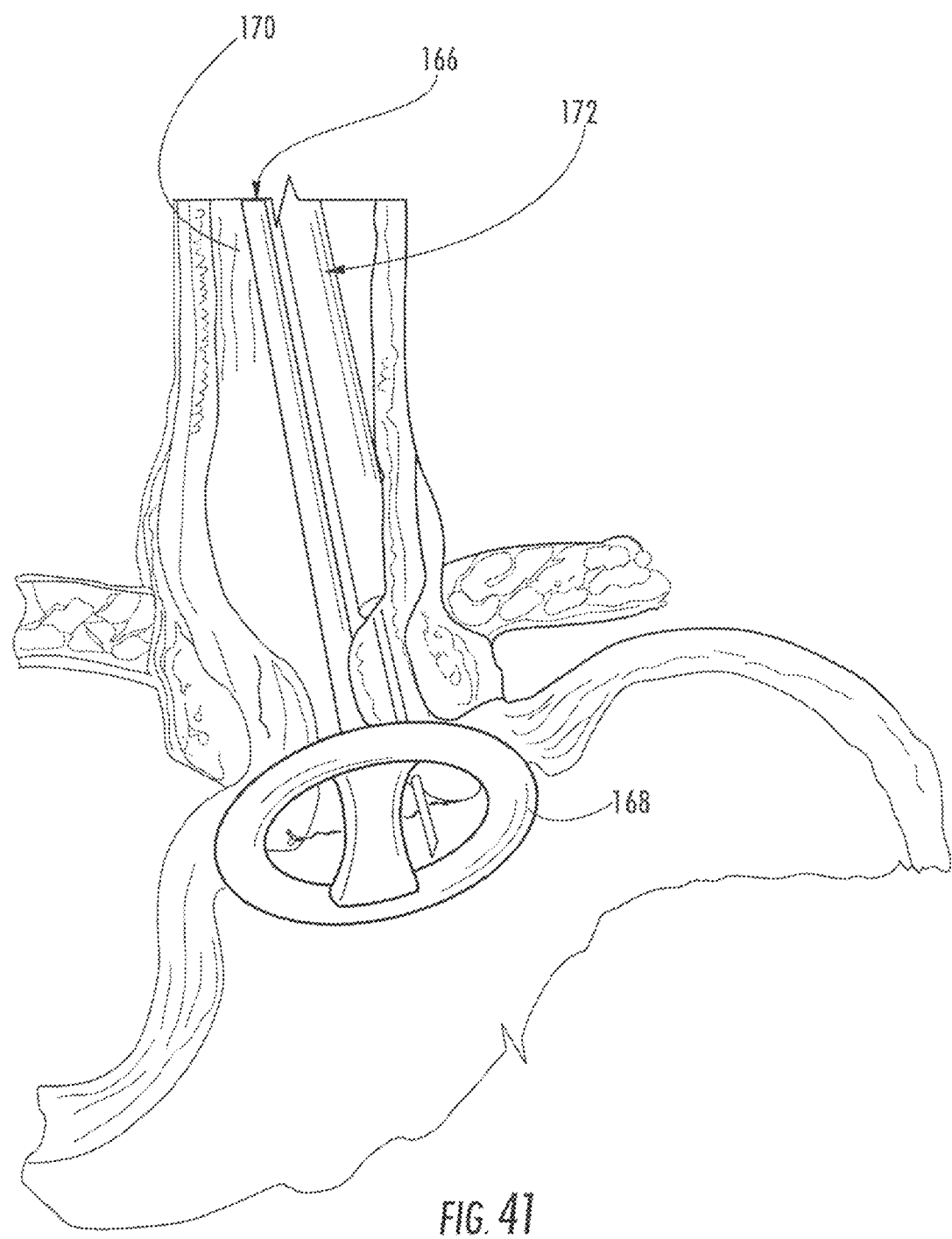
FIG. 41 a perspective view of another alternative embodiment of a bariatric device.

An alternative bariatric device 166 and an alternative embodiment of a deployment procedure for bariatric device 166 include a cardiac member 168 and an elongated shaft 170 for positioning the cardiac member against the cardia (FIG. 41). Proximal force on shaft 170 causes a bulge to be created at the GE junction to facilitate deployment of one or more tethers. An alternative tether assist device 172 is shown placing a tether needle through the GE junction and engaging cardiac member 168. Once the tether(s) is attached to cardiac member 168, the shaft 170 can be removed and any esophageal member (not shown) positioned in the esophagus and connected with the tether(s). Tether deployment device 172 may be used as shown or in combination with a vacuum to draw in the tissue of the GE junction in order to produce a bulge facilitate firing the tether pin through the tissue.

Figure 42:
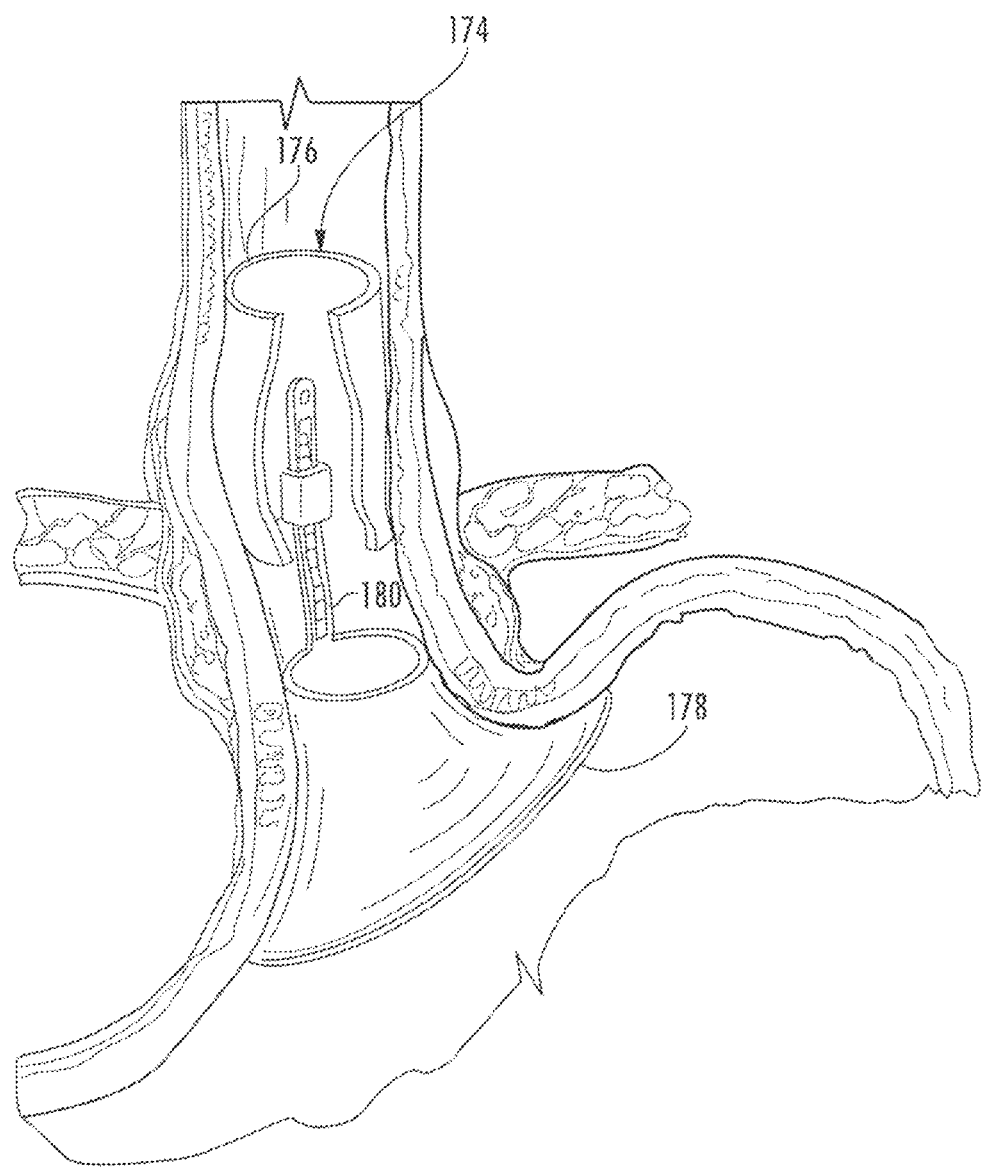
FIG. 42 is a perspective view of another alternative embodiment of a bariatric device.
Figure 43:
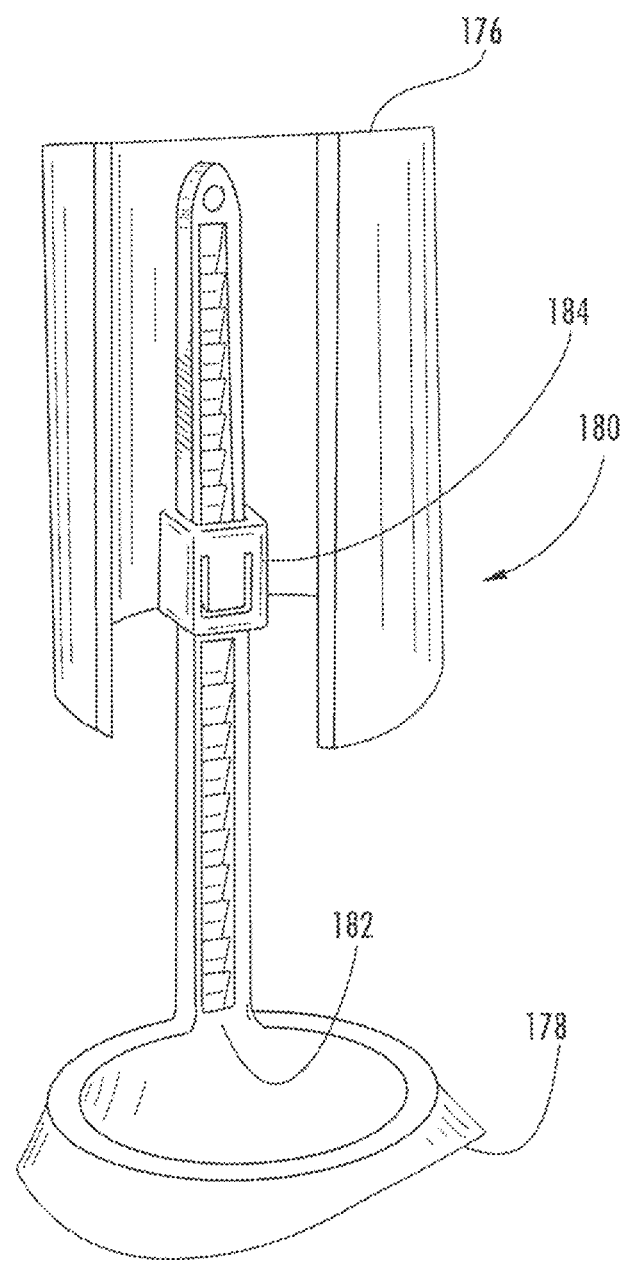
FIG. 43 is an enlarged view of a portion of the bariatric device in FIG. 42.

An alternative bariatric device 174 includes an esophageal member 176, a cardiac member 178, and a connector 180 that is adjustable (FIGS. 42 and 43). Connector 180 includes an adjustment system, such as a strap, 182 connected with cardiac member 178 and an adjustment mechanism 184 at the esophageal member that adjusts the relative position of esophageal member 176 with respect to the strap. It would be understood by the skilled artisan that strap 182 could be fixed to esophageal member 176, and the adjustment mechanism 184 fixed at cardiac member 178. Connector 180 allows the position of the cardiac member 178 to be adjusted relative to the esophageal member. This allows the amount of strain applied to the cardia to be increased or decreased after bariatric device 174 is deployed. This allows the amount of satiety to be adjusted if the recipient is experiencing too much or too little satiety. Also, adjustment may be made at the time of deployment of bariatric device 174. Alternatively, connector 180 may be adjusted by a control of the type disclosed in International Publication No. WO 2006/044640 A1 entitled BARIATRIC DEVICE AND METHOD, the disclosure of which is hereby incorporated herein by reference in its entirety.

Figure 44:
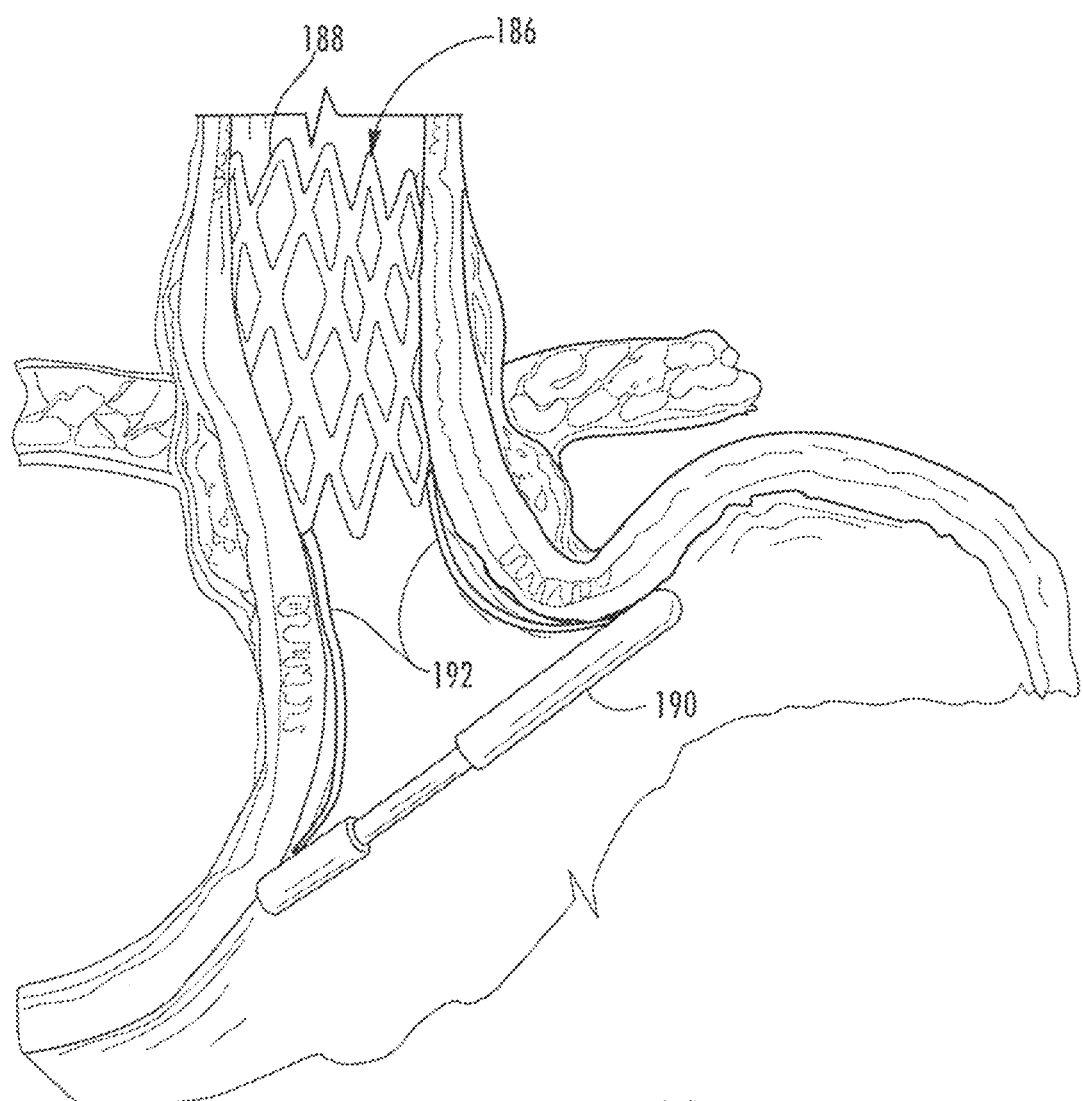
FIG. 44 is a perspective view of another alternative embodiment of a bariatric device.
Figure 45:
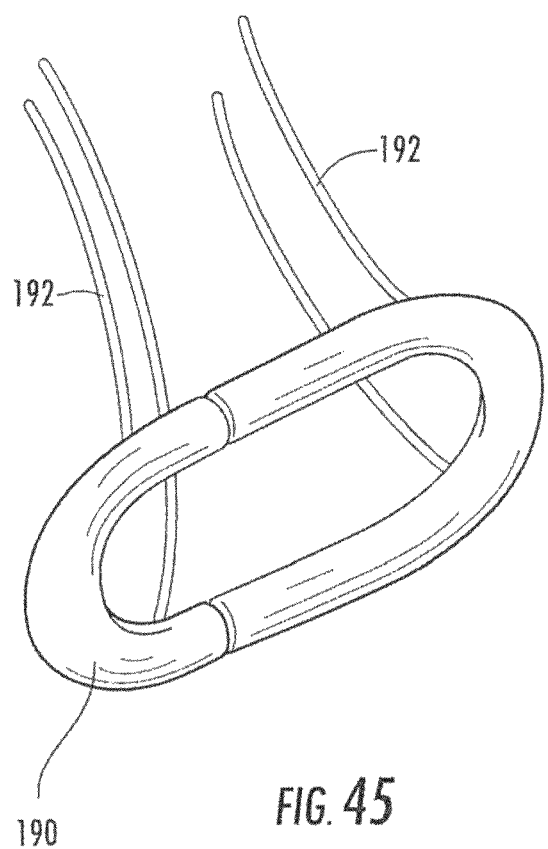
FIG. 45 a perspective view of the cardiac member of the bariatric device in FIG. 44.

An alternative bariatric device 186 includes an esophageal member 188, a cardiac member 190 and a connector 192 (FIGS. 44 and 45). Cardiac member 190 is a ring-shaped member. As best seen by comparing FIG. 44 and FIG. 45, cardiac member 190 may be compressed in length during deployment and elongated after being deployed to the stomach. This may not only ease deployment of cardiac member 190, but also may allow cardiac member 190 to apply strain in the form of elongation to the cardiac region in addition to pressure against the cardiac region. Connector 192 may be made up of a plurality of tethers that are placed inside of the GE junction, although they could also be placed external of the GE junction in a manner previously described. Because of their flexibility and placement, tether(s) 192 leaves a continuous portion of gastroesophageal junction substantially unrestrained.

Figure 46:
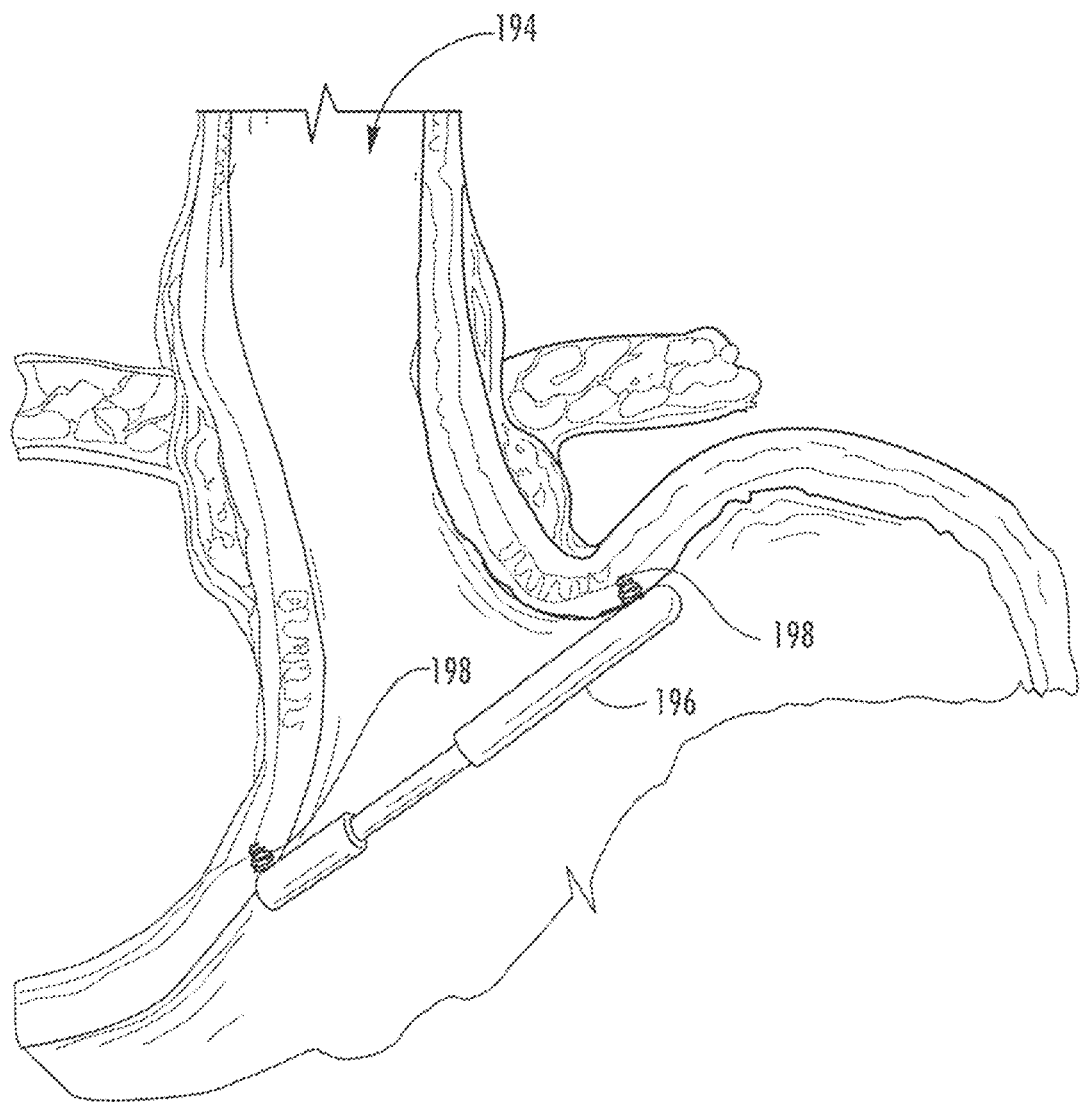
FIG. 46 a perspective view of another alternative embodiment of a bariatric device.

An alternative bariatric device 194 includes a cardiac member 196 that may be similar to cardiac member 190 (FIG. 46). However, cardiac member 196 may be anchored to the cardia, such as by utilizing an anchor, such as a spiral tacker, 198 engaging the cardia, or the like. This applies shear force to the cardia, thus stimulating both the tension receptors and the stretch receptors more directly. While not shown, bariatric device 194 may optionally include an esophageal member and a connector between the esophageal member and the cardiac member 196.

Figure 47:
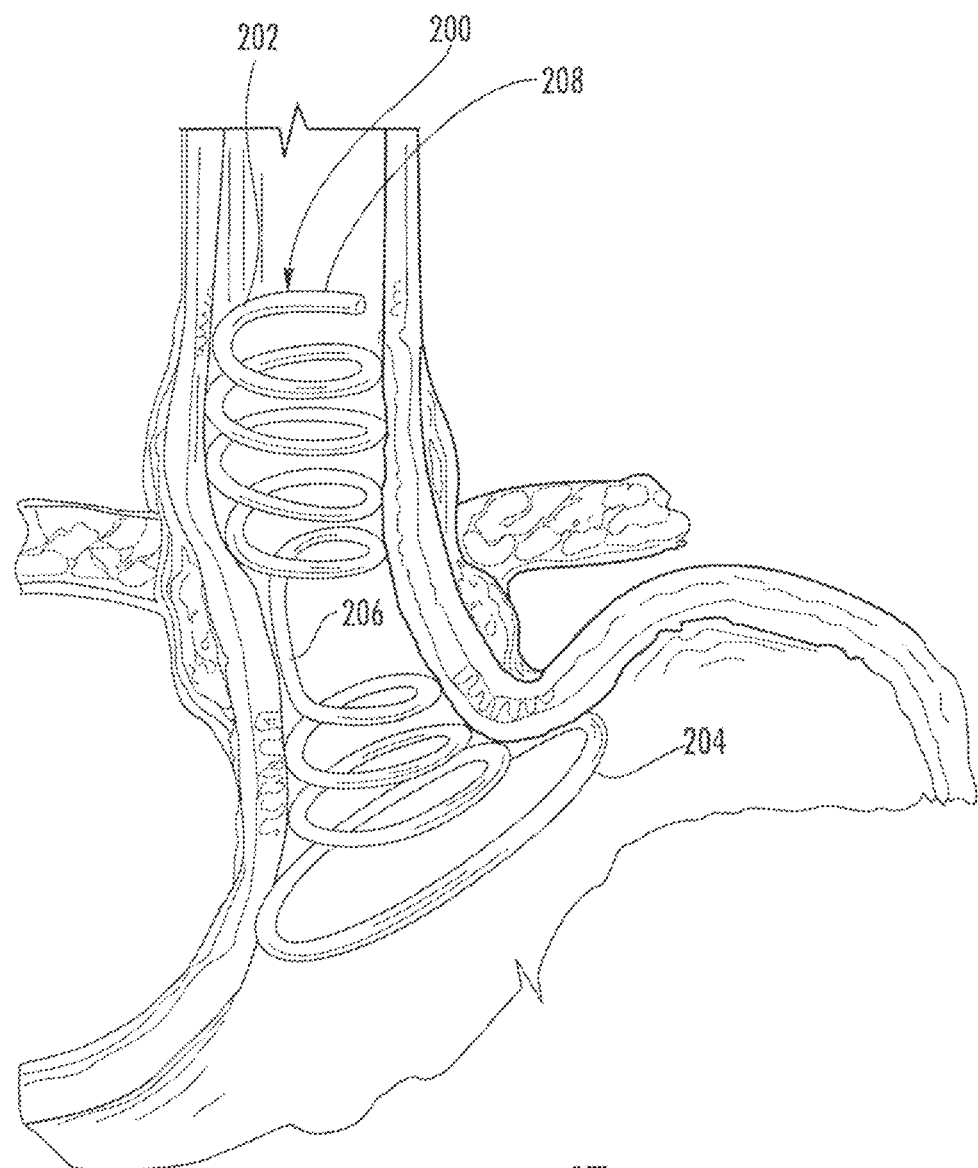
FIG. 47 is a perspective view of another alternative embodiment of a bariatric device.
Figure 48:
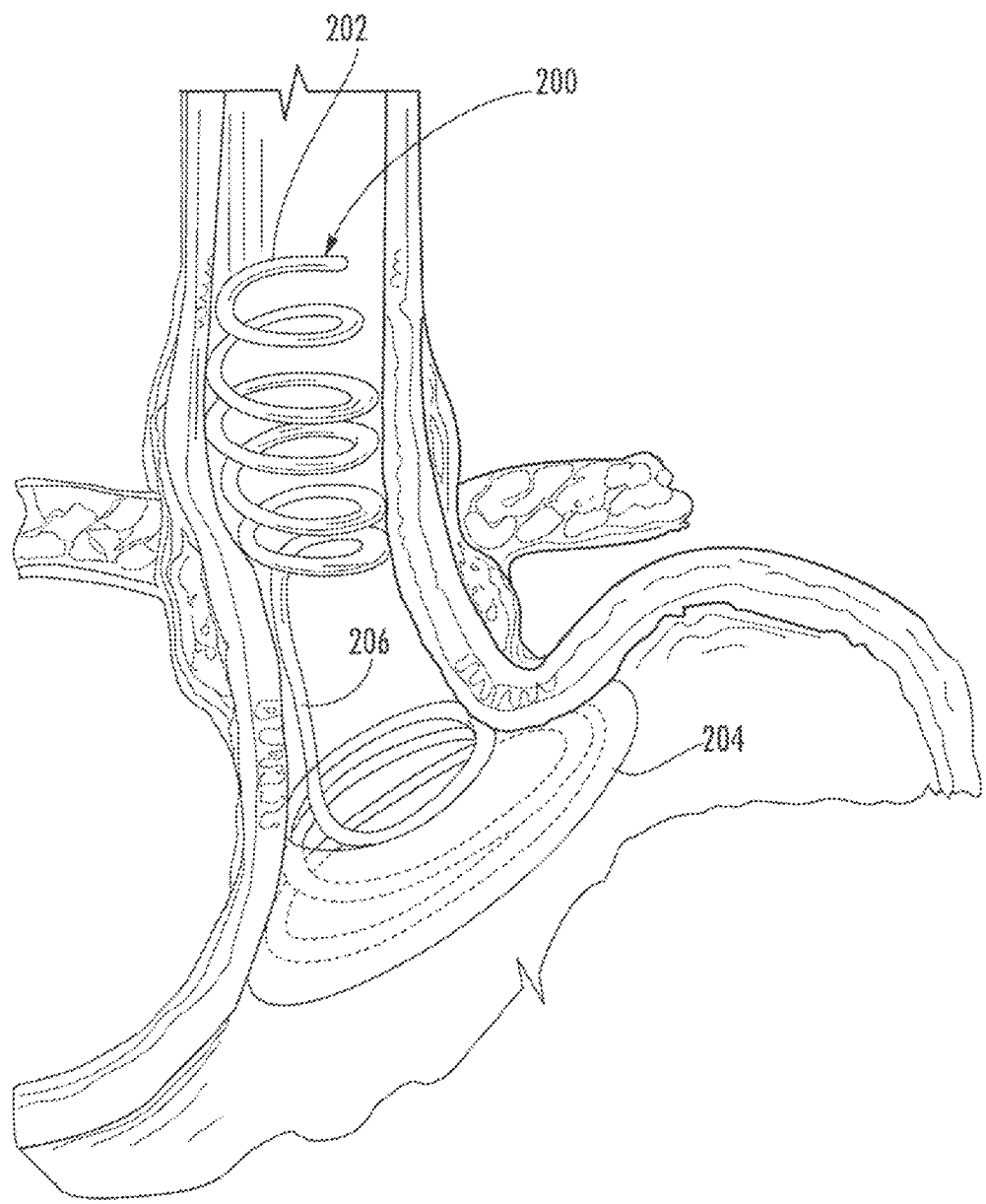
FIG. 48 is the same view as FIG. 47 including an outer surface cover for the cardiac member.

An alternative bariatric device 200 includes an esophageal member 202, a cardiac member 204, and a connector 206 that are commonly formed from an elongated member 208 (FIG. 47). Elongated member 208 is formed into a spiral to form esophageal member 202, is axially extending in order to form connector 206, and is formed into another spiral in order to form cardiac member 204. Elongated member 208 may be a wire, such as a Nitinol wire, a carbon filament, or the like. As best seen in FIG. 48, esophageal member 202 and/or cardiac member 204 may be covered with a sleeve, such as silicone, in order to form a substantially smooth external surface in order to reduce erosion to the recipient's esophagus or cardia.

Figure 49:
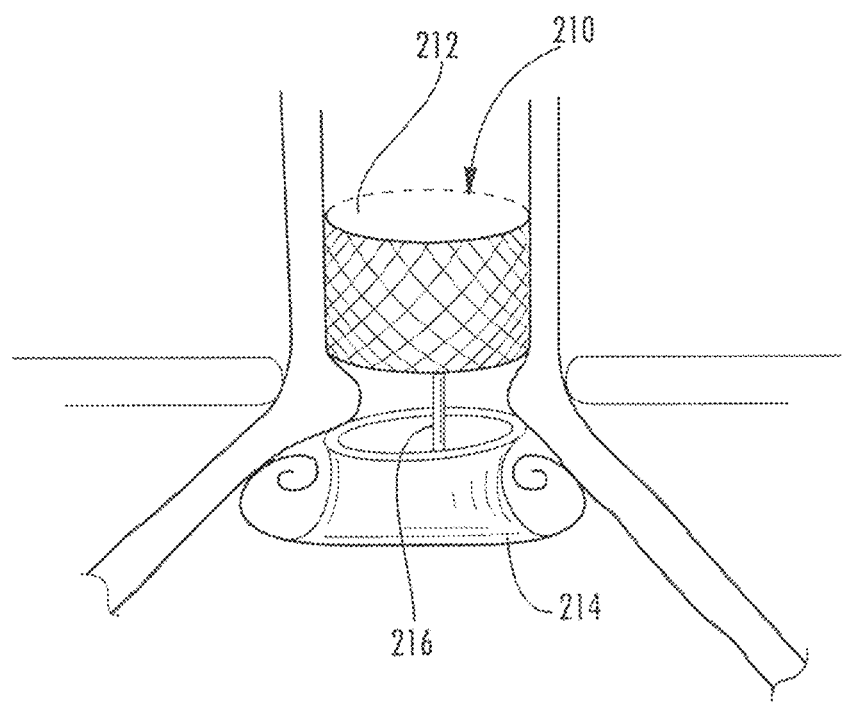
FIG. 49 is a perspective view of another alternative embodiment of a bariatric device.

An alternative bariatric device 210 may include an esophageal member 212, a cardiac member 214, and a connector 216 (FIG. 49). Cardiac member 214 may be made from a relatively planar member that has memory, whereby the planar member may be collapsed to pass through the recipient's esophagus and self-expanded to the shape illustrated in FIG. 49 in order to engage the cardia.

Figure 50:
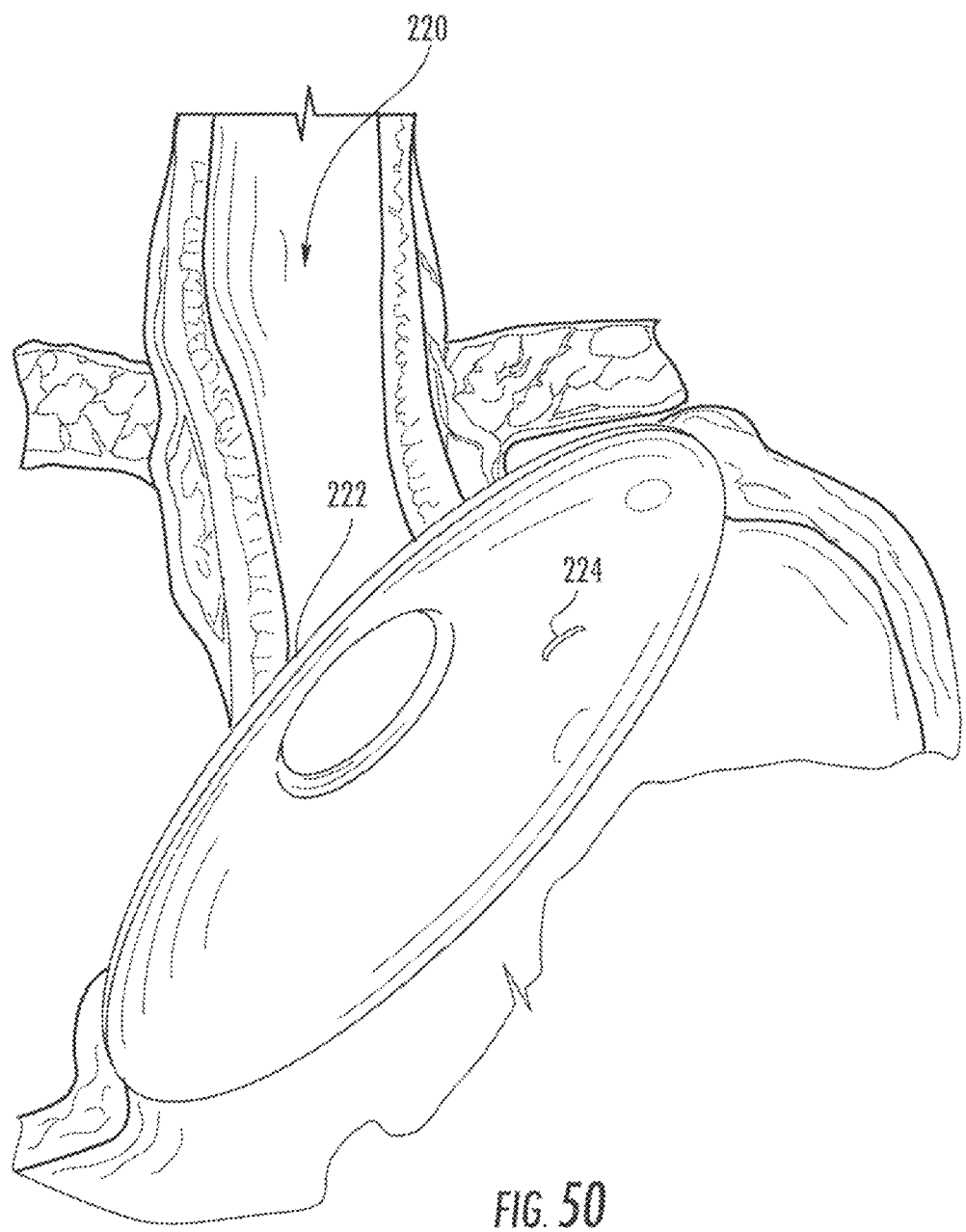
FIG. 50 is a perspective view of another alternative embodiment of a bariatric device.

An alternative bariatric device 220 is in the form of a disk-shaped body 222, which is fastened to the cardia by anchors at points 224 around its perimeter (FIG. 50). Such fastening may be in the form of a spiral tacker, or other anchor. The presence of periphery anchoring is to provide shear strain as well as pressure strain to the cardia. An esophageal member and connector may optionally be used.

Figure 51:
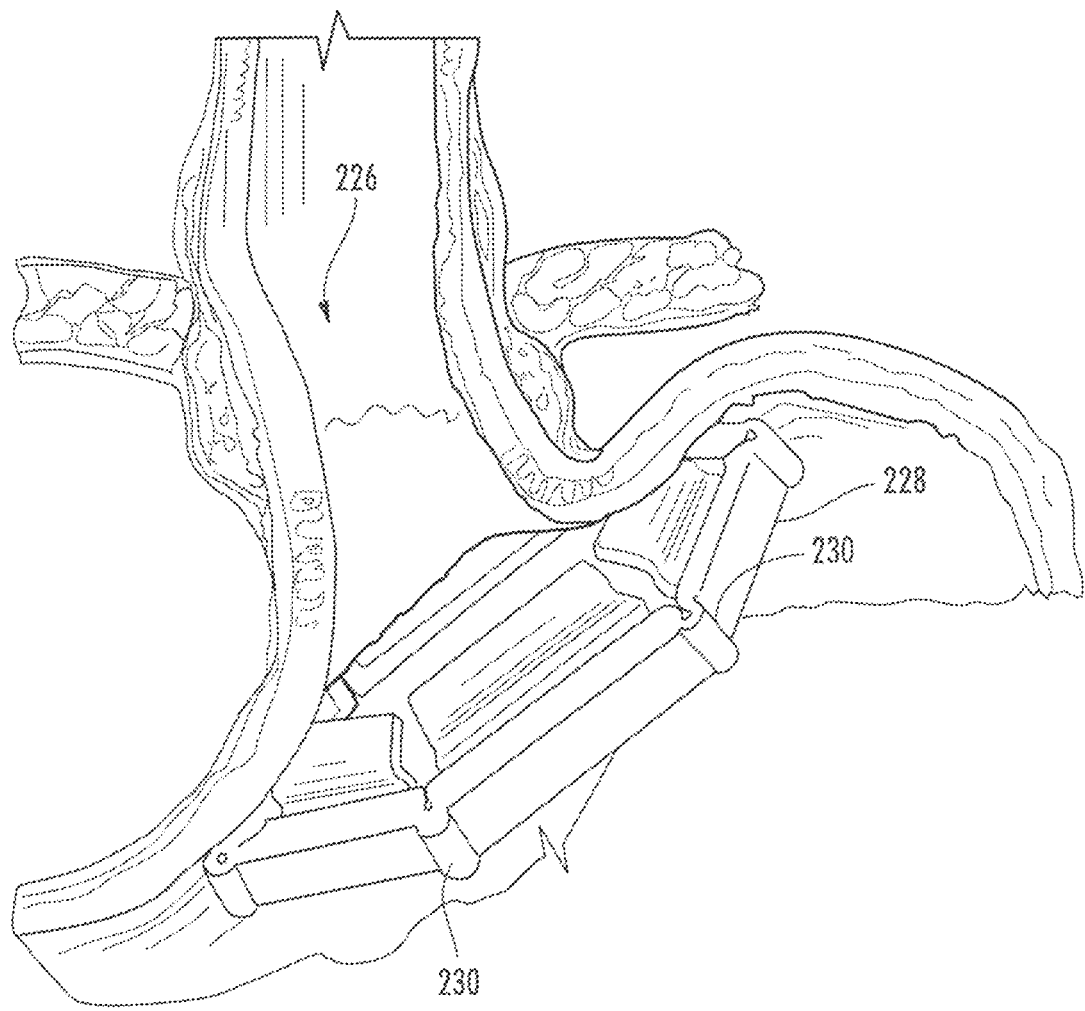
FIG. 51 is a perspective view of another alternative embodiment of a bariatric device.
Figure 52:
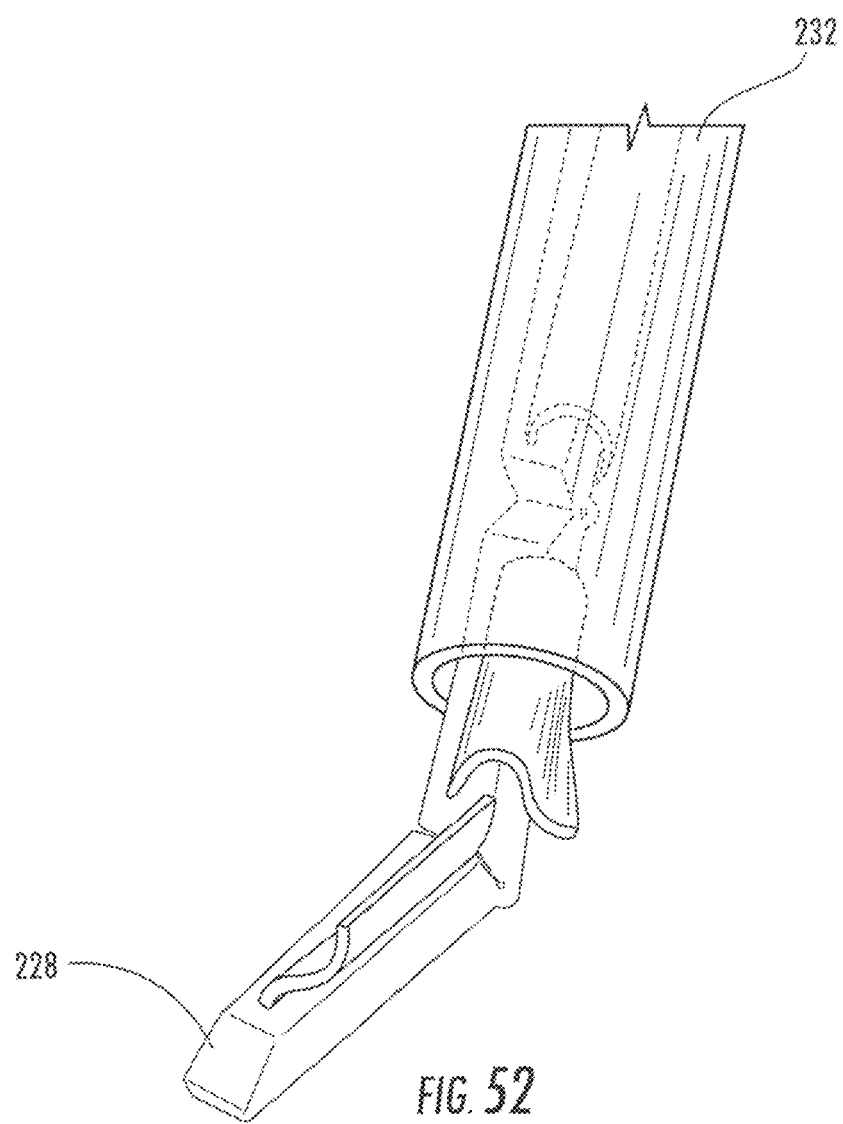
FIG. 52 is a perspective view illustrating deployment of the bariatric device of FIG. 51.

An alternative bariatric device 226 is made up of a series of articulated segments 228, which can be deployed in a linear fashion as illustrated in FIG. 52, but which form a ring-shaped device upon deployment, as illustrated in FIG. 51. Segments 228 can be interconnected by living hinges 230, which may be biased into the circular orientation of FIG. 51. The segments may be deployed through a delivery tube 232.

Figure 53:
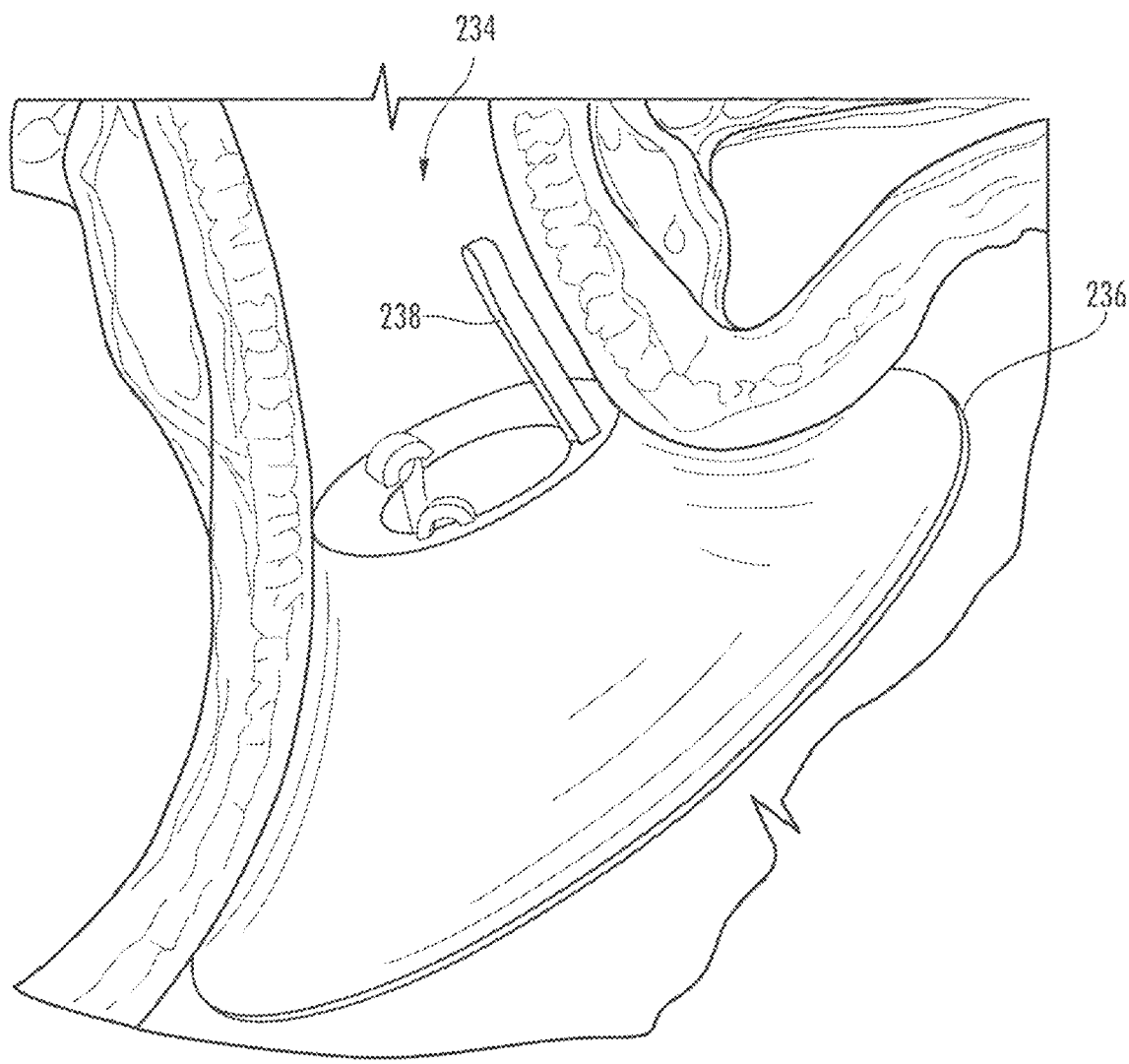
FIG. 53 is a perspective view of an alternative embodiment of a bariatric device.
Figure 54:
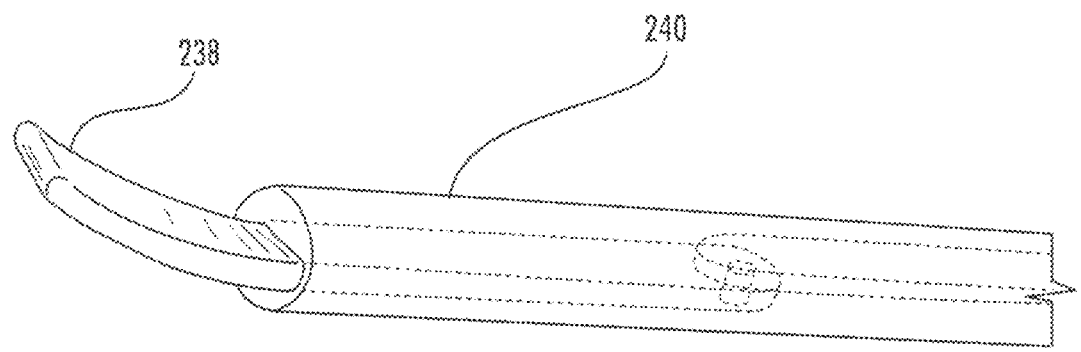
FIG. 54 is a perspective view of deployment of the bariatric device illustrated in FIG. 53.

An alternative bariatric device 234 includes an esophageal member (not shown), a cardiac member 236, and a connector 238 that connects the esophageal member and the cardiac member (FIGS. 53 and 54). Connector 238 is made up of one or more straps that are removable. This allows the physician to substitute a strap having more or less flexibility for another strap. This allows the stiffness of the connector to be tailored to the recipient as well as adjusted after a period of time, as needed. Also, different length straps may be substituted. An insertion tool 240 may be provided in order to insert the strap into the cardiac member 236 and the esophageal member (not shown).

Figure 55:
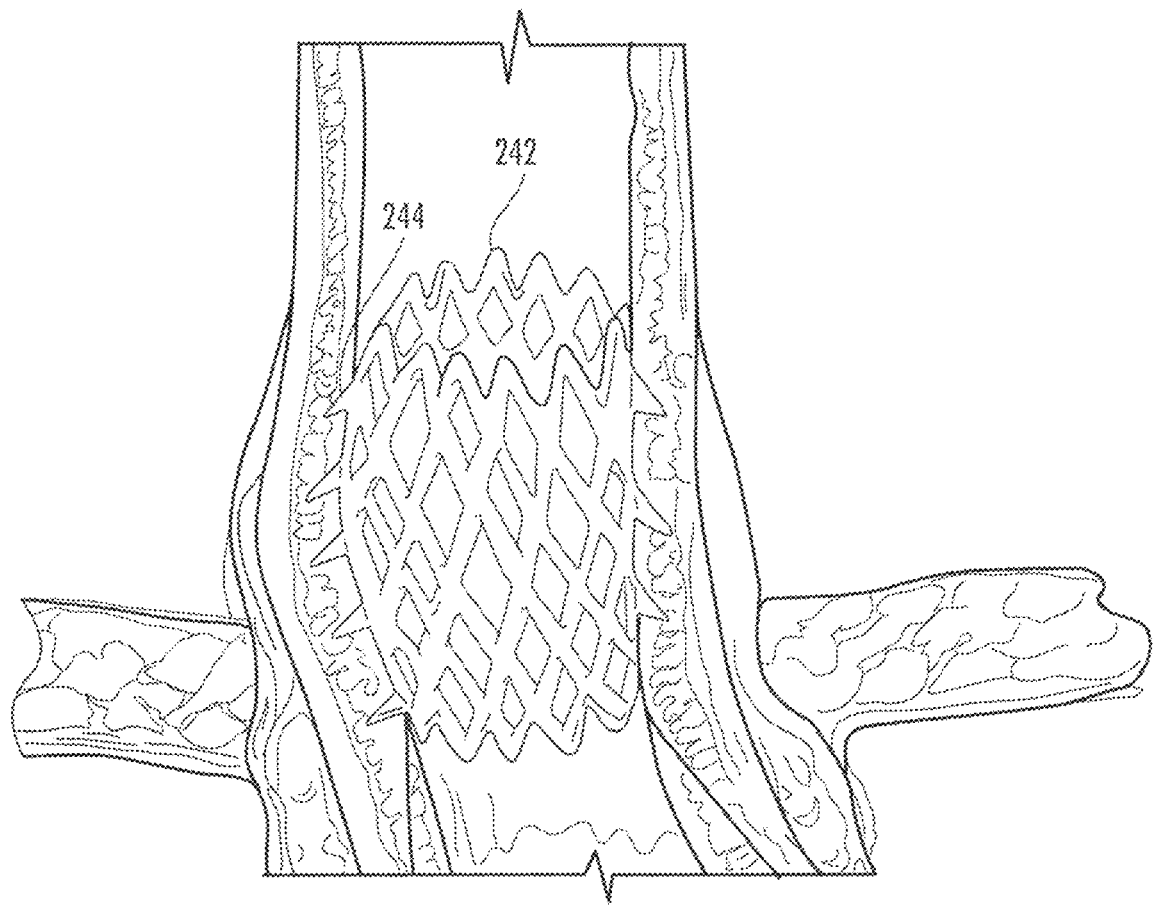
FIG. 55 is a perspective view of an alternative embodiment of an esophageal member.

An alternative esophageal member 242 includes a series of peripheral tines 244 that assist in anchoring the esophageal member in the tissue at, or adjacent to, the GE junction (FIG. 55).

Figure 56:
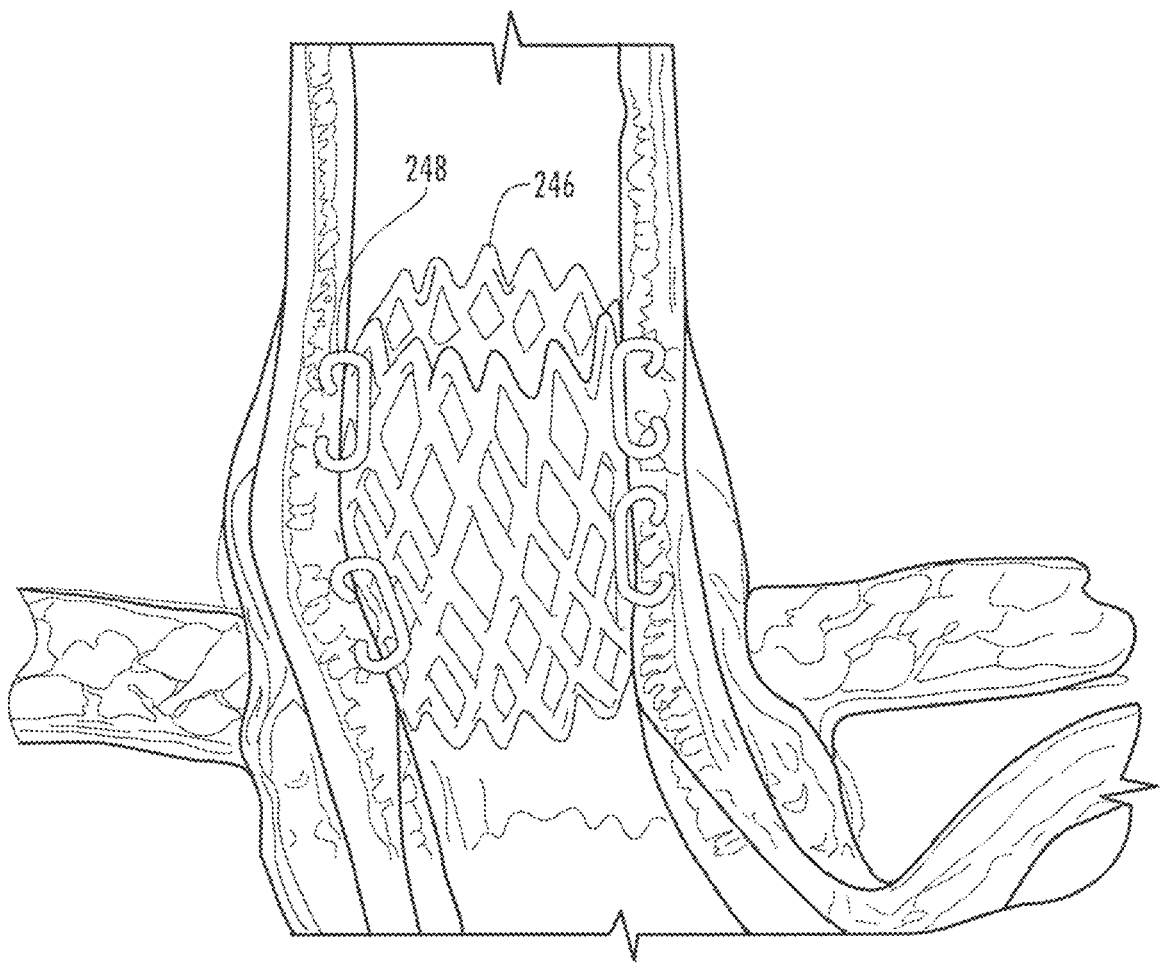
FIG. 56 is a perspective view of another alternative embodiment of an esophageal member.

An alternative esophageal member 246 is anchored at or adjacent the GE junction by a series of barbs or staples 248 that are applied after the esophageal member is deployed (FIG. 56).

Figure 57:
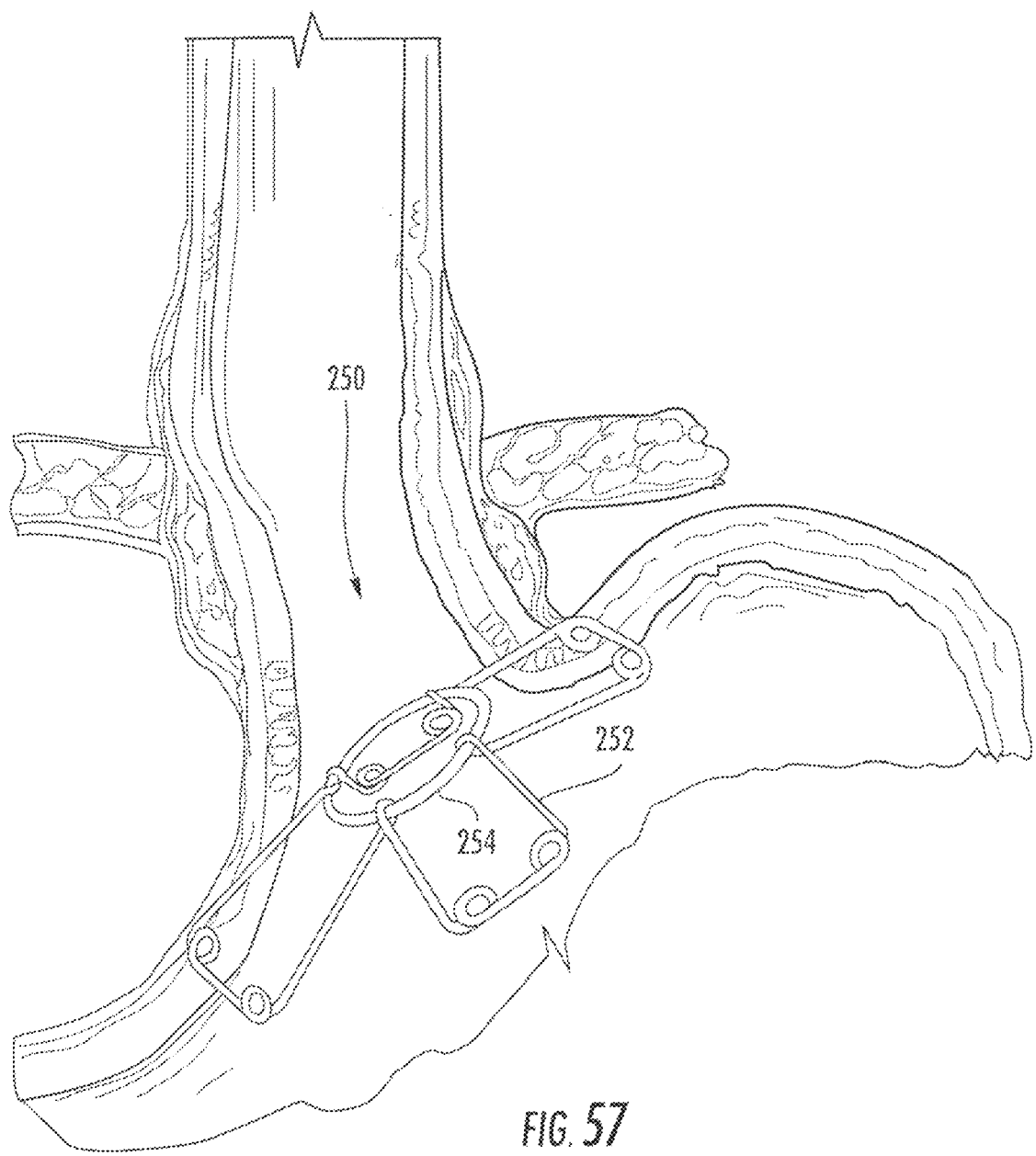
FIG. 57 is a perspective view of an alternative embodiment of a cardiac member.

An alternative bariatric device 250 has a cardiac surface that is made up of a series of leafs 252 that are interconnected by a central ring 254. Leafs 252 are spring-biased into the position illustrated in FIG. 57, but may be folded for deployment. The leafs 252 are illustrated as being formed from an elongated member, such as Nitinol wire. They may be covered by a sleeve, or the like, in order to reduce mucosal erosion.

Figure 58:
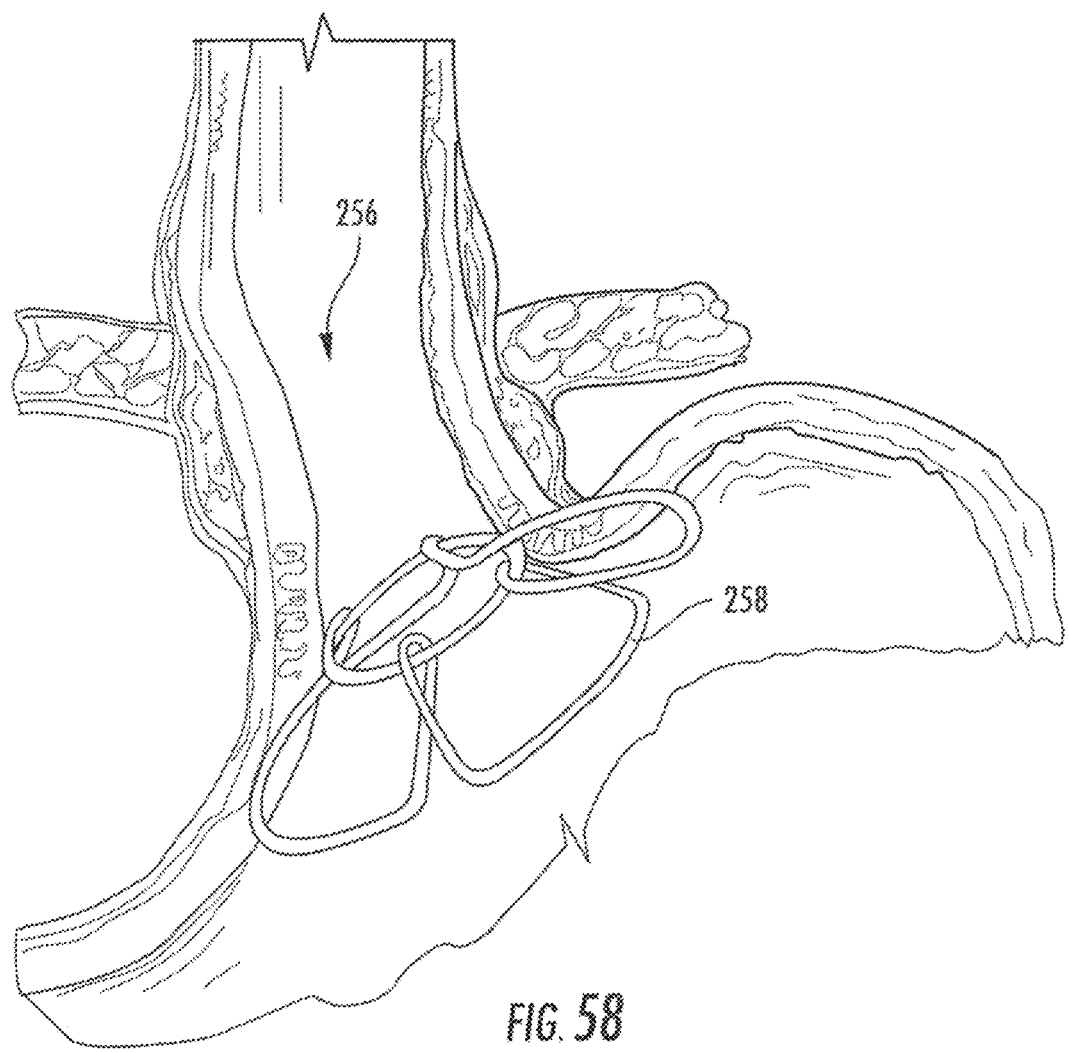
FIG. 58 is a perspective view of another alternative embodiment of a cardiac member.

An alternative bariatric device 256 is similar to cardiac member 250 except that leafs 258 are formed from a continuous elongated member, such as Nitinol wire (FIG. 58). However, leafs 258 may be folded for deployment and self-expand to the form shown in FIG. 40 after deployment.

Figure 59:
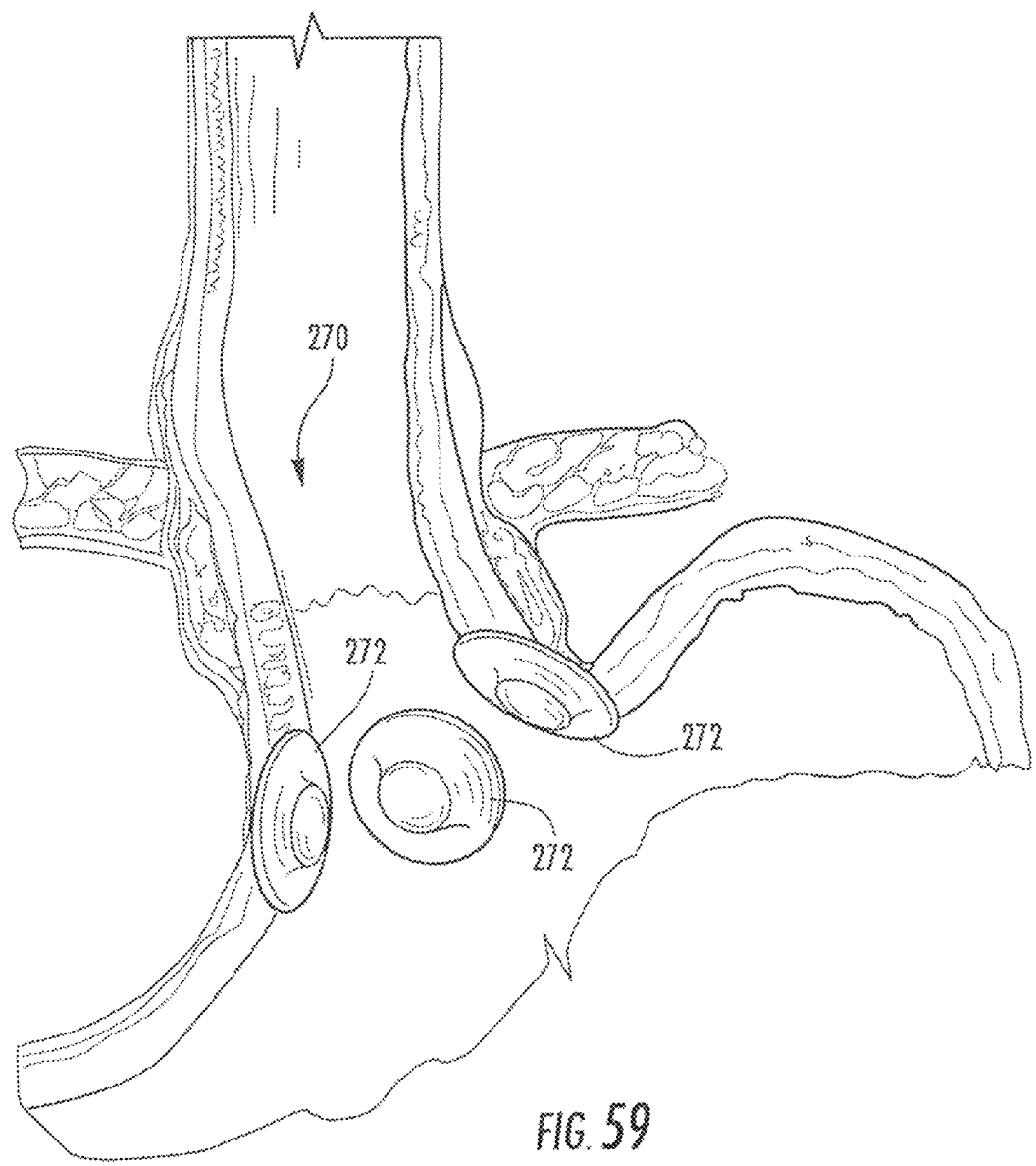
FIG. 59 is a perspective view of another alternative embodiment of a bariatric device.
Figure 60:
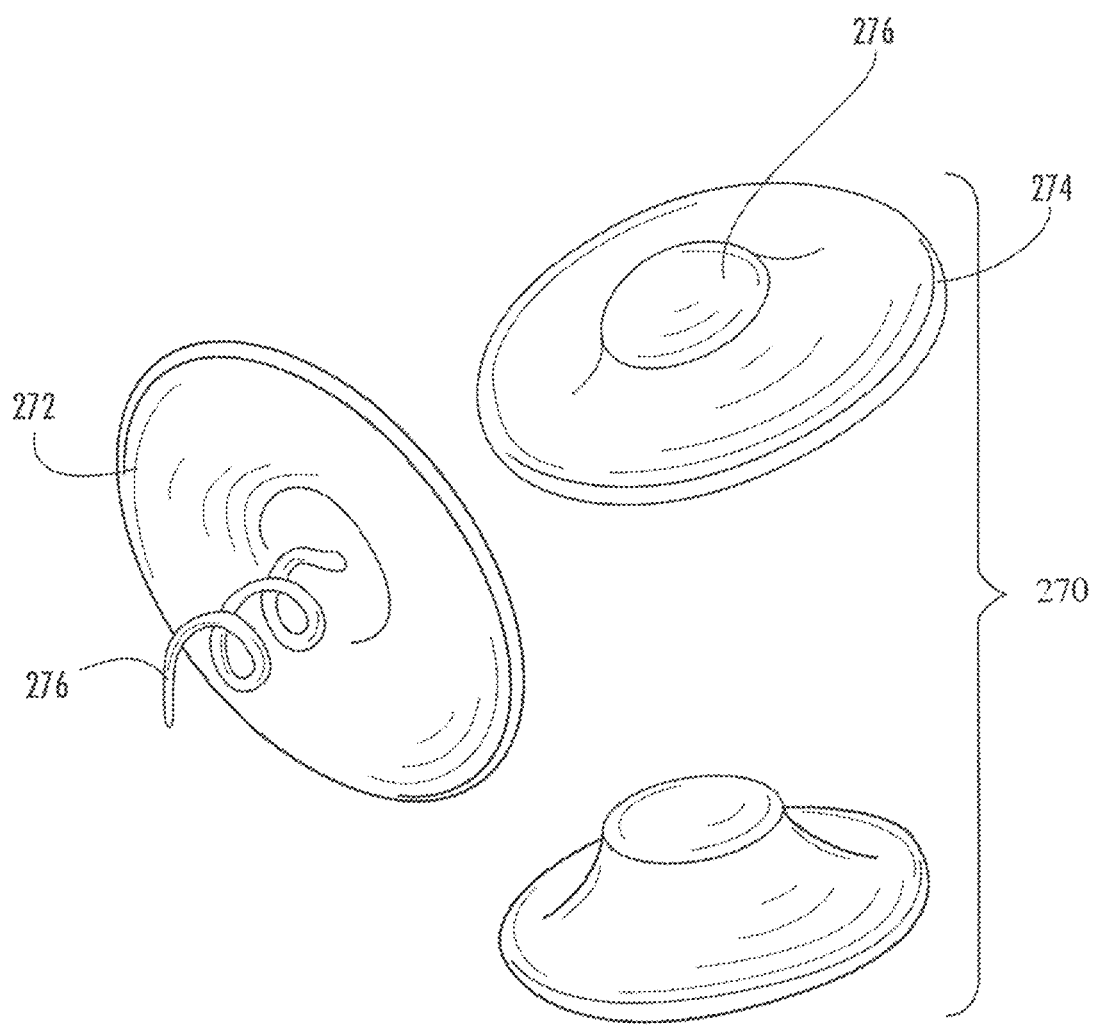
FIG. 60 is a perspective view of the bariatric device of FIG. 59.

An alternative bariatric device 270 is in the form of a series of pressure patches 272 (FIGS. 59 and 60). Each pressure patch 272 includes a resilient disk 274 and an anchor 276. The anchor is configured to engage the cardia and press the disk against the cardia. This allows each pressure patch 272 to stimulate a portion of the cardia by applying pressure to the cardia. Anchor 276 may be in the form of a spiral fastener, although others would be apparent to the skilled artisan.

Figure 61:
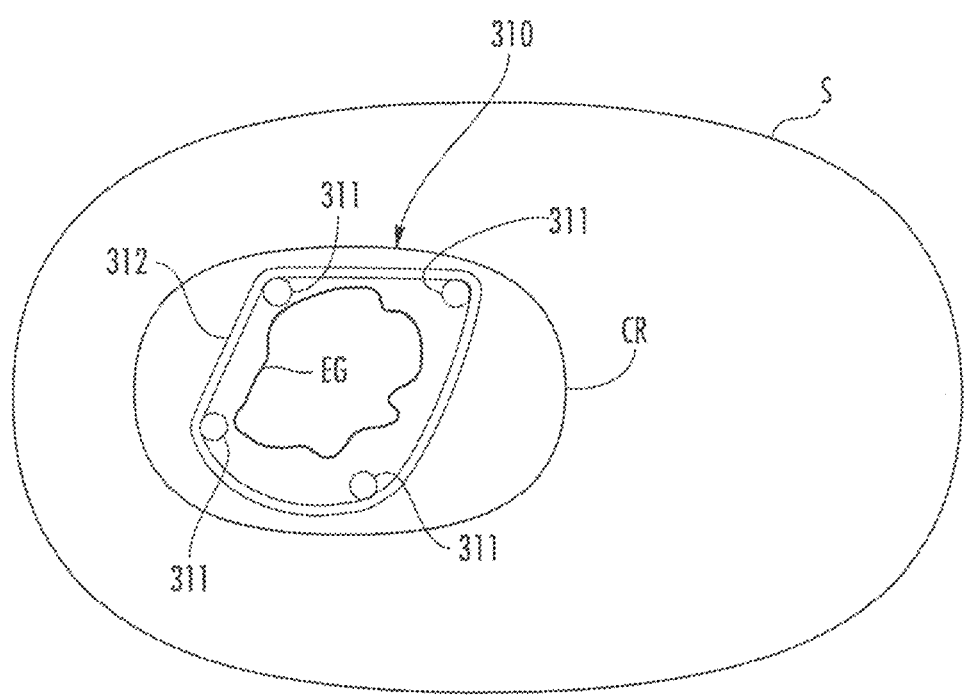
FIG. 61 is a distal view of another alternative embodiment of a bariatric device.
Figure 62:
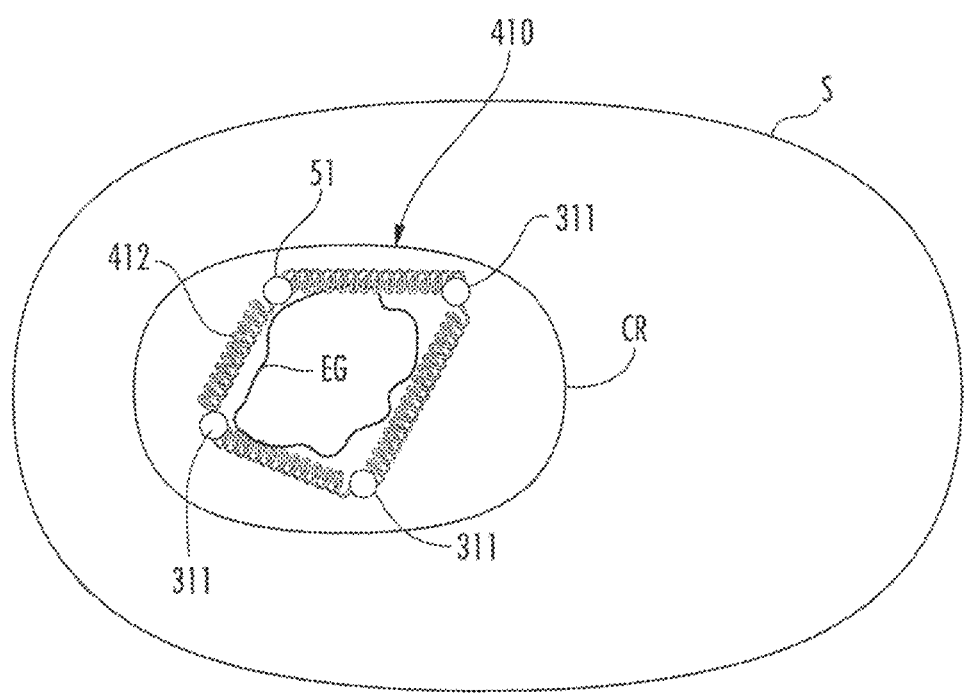
FIG. 62 is the same view as FIG. 61 of another alternative embodiment of a bariatric device.
Figure 63:
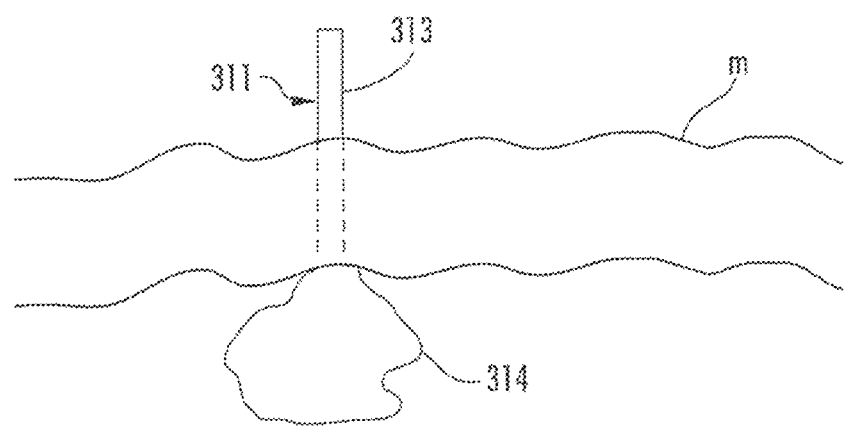
FIG. 63 is an elevation of a stud used in FIGS. 62 and 63.
Figure 64:
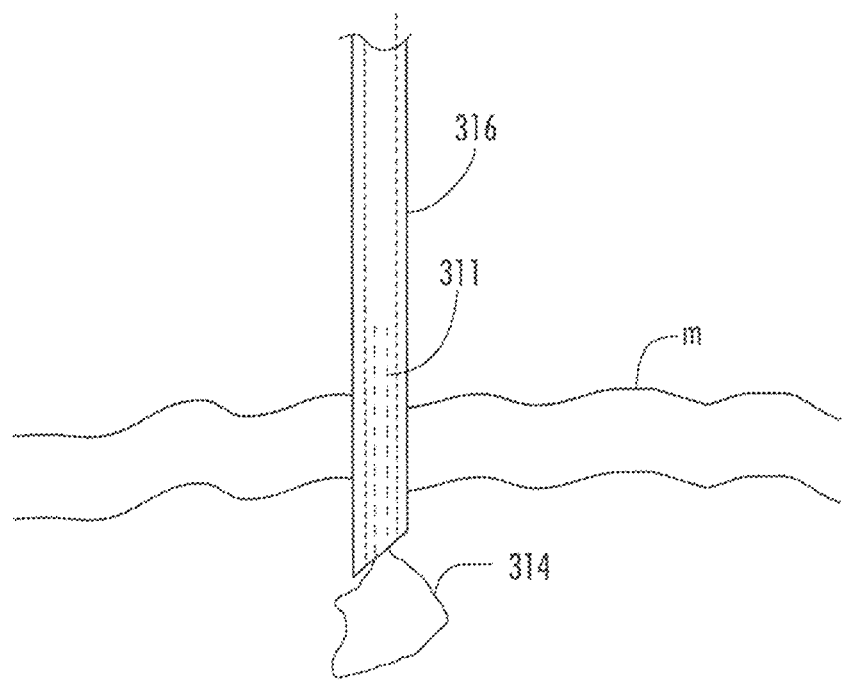
FIG. 64 is the same view as FIG. 63 illustrating installation of the stud.
Figure 65:
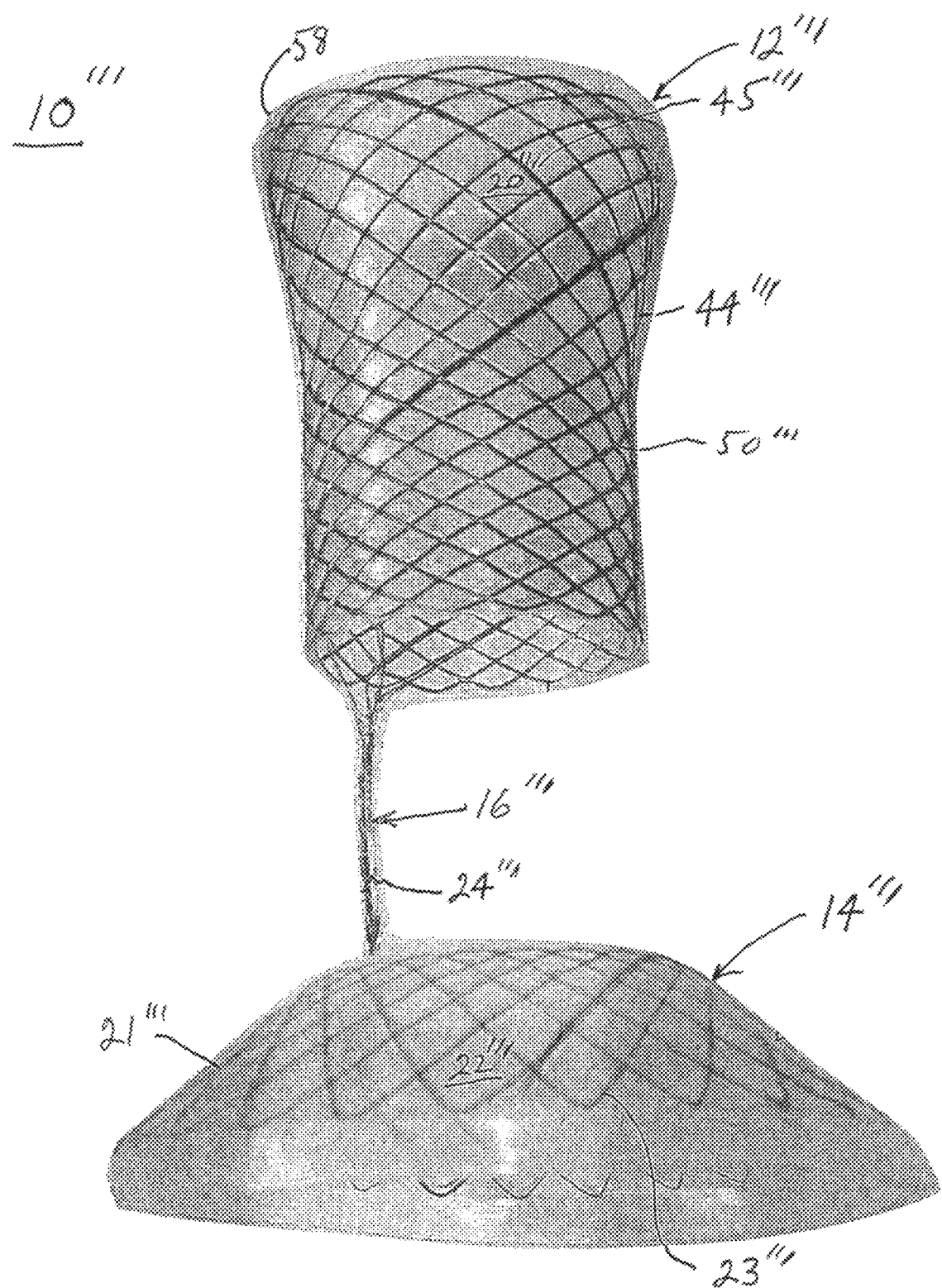
FIG. 65 is a perspective view of another alternative embodiment of a bariatric device.
Figure 66:
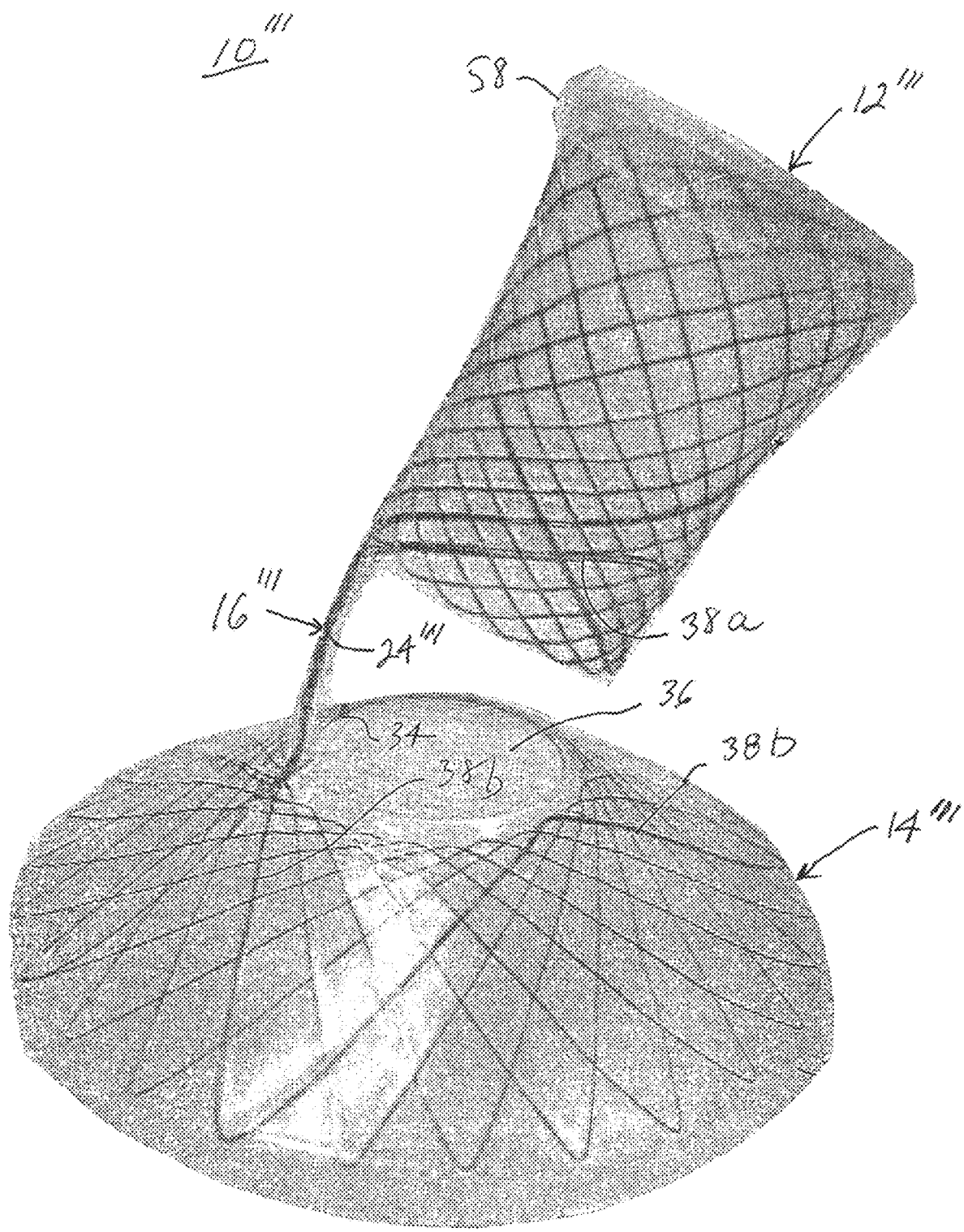
FIG. 66 is another perspective view of the bariatric device of FIG. 65.
Figure 67:
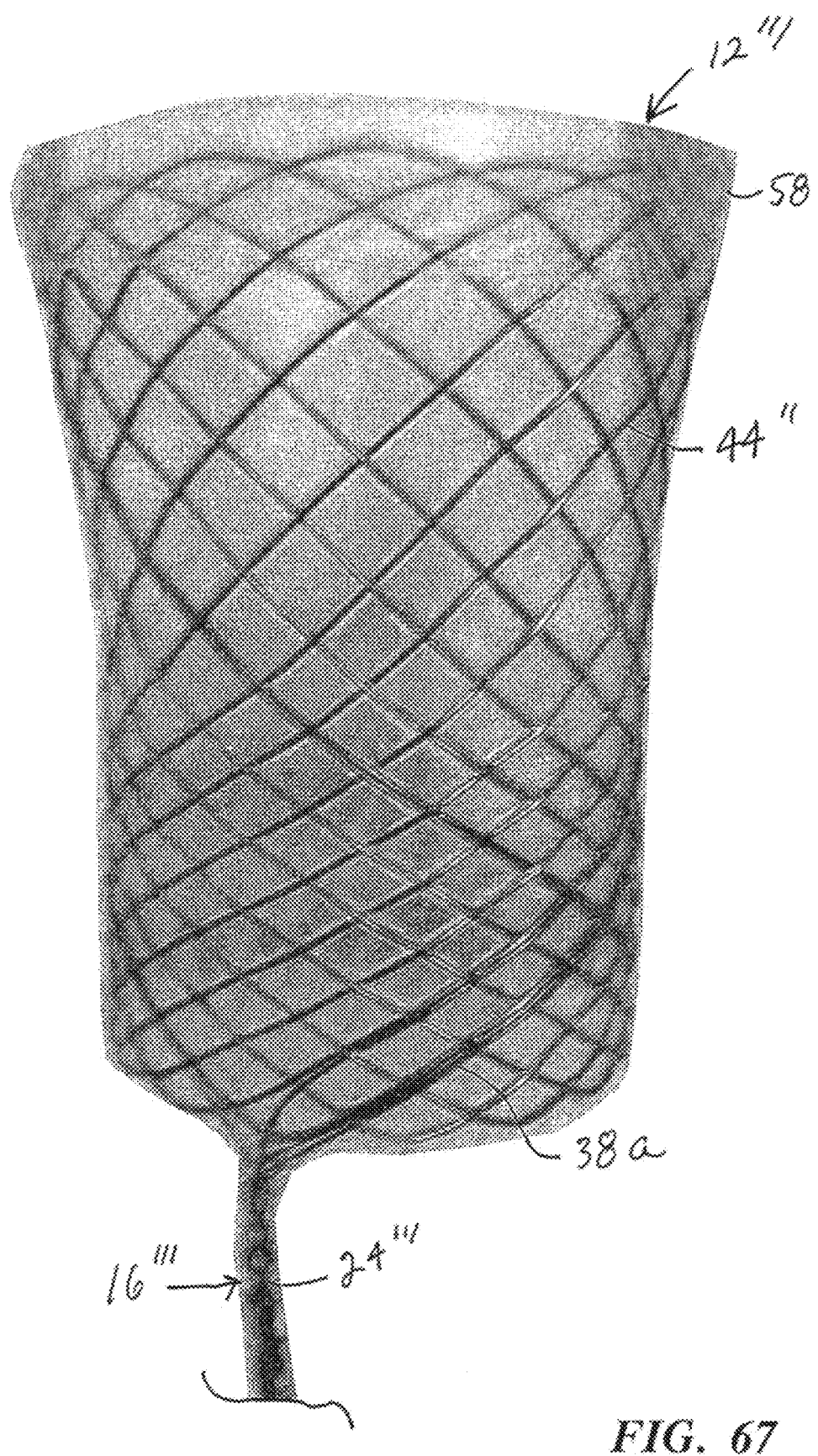
FIG. 67 is an enlarged perspective view of the esophageal member of the bariatric device of FIG. 65.
Figure 68:
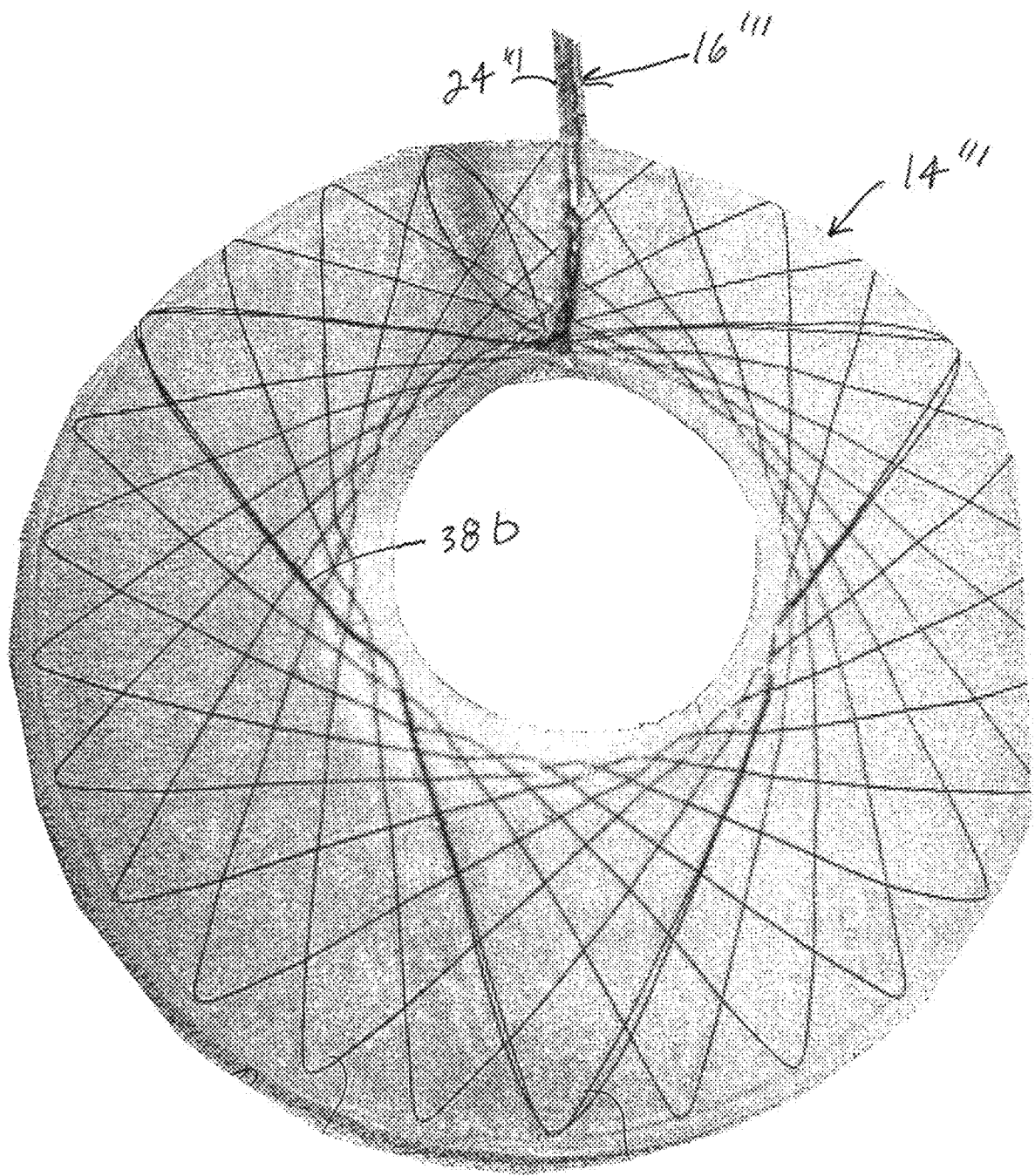
FIG. 68 is an enlarged perspective view of the cardiac member of the bariatric device of FIG. 65.

A bariatric device 310 according to an alternative embodiment may, alternatively, apply a stretch force, such as a proximal/distal force, to the abdominal portion of the esophagus, the esophageal-gastric junction, and/or the cardia. In the illustrative embodiment, bariatric device 310 includes a plurality of anchors, or studs, 311 positioned about or around the cardiac region CR of the stomach (FIG. 61). Bariatric device 310 additionally includes a cardiac member in the form of a band 312 which applies a lateral force against studs 311. Band 312 may be elastic and stretched upon application to apply a laterally inward force on studs 311, as illustrated in FIG. 61. Alternatively, band 312 may be elastic and compressed upon application to apply a laterally outward force on studs 311. An optional mechanism, such as a clip, or the like, may be used to hold band 312 to studs 311. Studs may be generally stiff or may be flexible according to the application.

In the illustrated embodiment, each stud 311 has a post 313 extending into the stomach and a support, such as a mesh 314 anchored in the stomach wall. The mesh may have tissue ingrowth, tissue attachment or mucosal capture openings to promote fixation to the mucosa, submucosa and/or muscularis. The studs may be applied in a separate procedure before the band 312 is applied to allow time for the studs to be firmly supported. Alternatively, studs may be provided as disclosed in U.S. Pat. No. 6,991,643 B2 entitled MULTI-BARBED DEVICE FOR RETAINING TISSUE IN APPOSITION AND METHODS OF USE and U.S. Pat. No. 7,160,312 B2 entitled IMPLANTABLE ARTIFICIAL PARTITION AND METHOD OF USE, the disclosures of which are hereby incorporated herein by reference. Studs 311 may be deployed using a pointed deployment tool 316. This may be accomplished endoscopically.

Another alternative bariatric device 410 is similar to bariatric device 310 in that it utilizes a plurality of anchors, or studs, 311 positioned about the cardiac region CR of the recipient. A cardiac member in the form of a series of expansion members, such as expansion springs 412, may be applied between adjacent studs 311 to apply a lateral force to the studs to apply a strain to the cardiac region to stimulate receptors there.

Another alternative bariatric device 10''' includes an esophageal member 12''' and a cardiac member 14''' that may be made of a generally resilient material having sufficient flexibility to allow it to be compacted to pass through the esophagus while having sufficient rigidity to allow it to transmit strain from a connector 16''' to the cardiac region of the stomach, such as in the form of an outwardly directed force (FIGS. 65-68). In the illustrated embodiment, body 21''' of cardiac member 14''' is made from a molded silicone, embedded weave 23''' of flexible wire, such as Nitinol wire. The weave increases tear resistance and stiffness. Body 21''' may include a proximally raised portion 34 defining a flange. Flange 34 is configured to fit against the GE junction. This causes food to be directed through-opening 36 in body 21''' while resisting the food passing between cardiac surface 22''' and the wall of the stomach. In the illustrated embodiments, body 21''' may be made from a material, such as a type of molded silicone that is substantially transparent to light. This allows the physician deploying device 10 to be able to better visualize placement of the device during its deployment as would be understood by the skilled artisan.

Esophageal member 12''' may apply a tension to the distal esophagus, such as an outwardly directed force over the area of surface 20'''. Esophageal member 12''' may include a cage 44''' and an impervious wall 45''' covering cage 44'''. Wall 45''' may be made from molded silicone, which, in the same manner as body 21''', may be substantially transparent to light to enhance visibility during deployment. Cage 44''' may be made from an elongated member 50''', which, in the illustrated embodiment, is an elastic member, such as Nitinol wire. Member 50''' is formed as an interwoven spiral. Esophageal member 12''' additionally includes a cover 58 over the proximal end of cage 44'''. Cover 58 provides additional flexibility to the distal end of member 12''' to further minimize the potential for erosion or ulceration as well as to provide a better engagement with the esophageal wall.

Connector 16''' includes a tension member 24''' may pass through opening 36 and has a distal extension 38b that gets incorporated into body 21''' of the cardiac member and a proximal extension 38a that gets incorporated into esophageal member 12'''. Tension member 24''' is defined by one or more strands of flexible wire, such as Nitinol wire covered with a molded silicone layer. Proximal extension 38a and distal extension 38b are extensions of the wire defining tension member 24''. While extensions 38a, 38b are illustrated as woven with weave 23''' and cage 44''', it should be understood that they may also be an extension of the wires defining weave 23''' and cage 44'''. Indeed, it is contemplated that cage 44, tension member 24, and weave 23 may be made from a single strand of flexible wire, such as Nitinol wire. While only one tension member 24''' is illustrated, it would be possible to add a second one that is radially opposite with respect to opening 36. The addition of a second such tension member may reduce the likelihood of cardiac member 14''' being displaced during deployment by resisting torsional forces placed on the cardiac member. This may help to keep esophageal member 12''' and cardiac member 14''' in better alignment, notwithstanding such forces. However, the presence of a second tension member may undesirably impede normal functioning of the pseudo sphincter at the GE junction.

Figure 69:
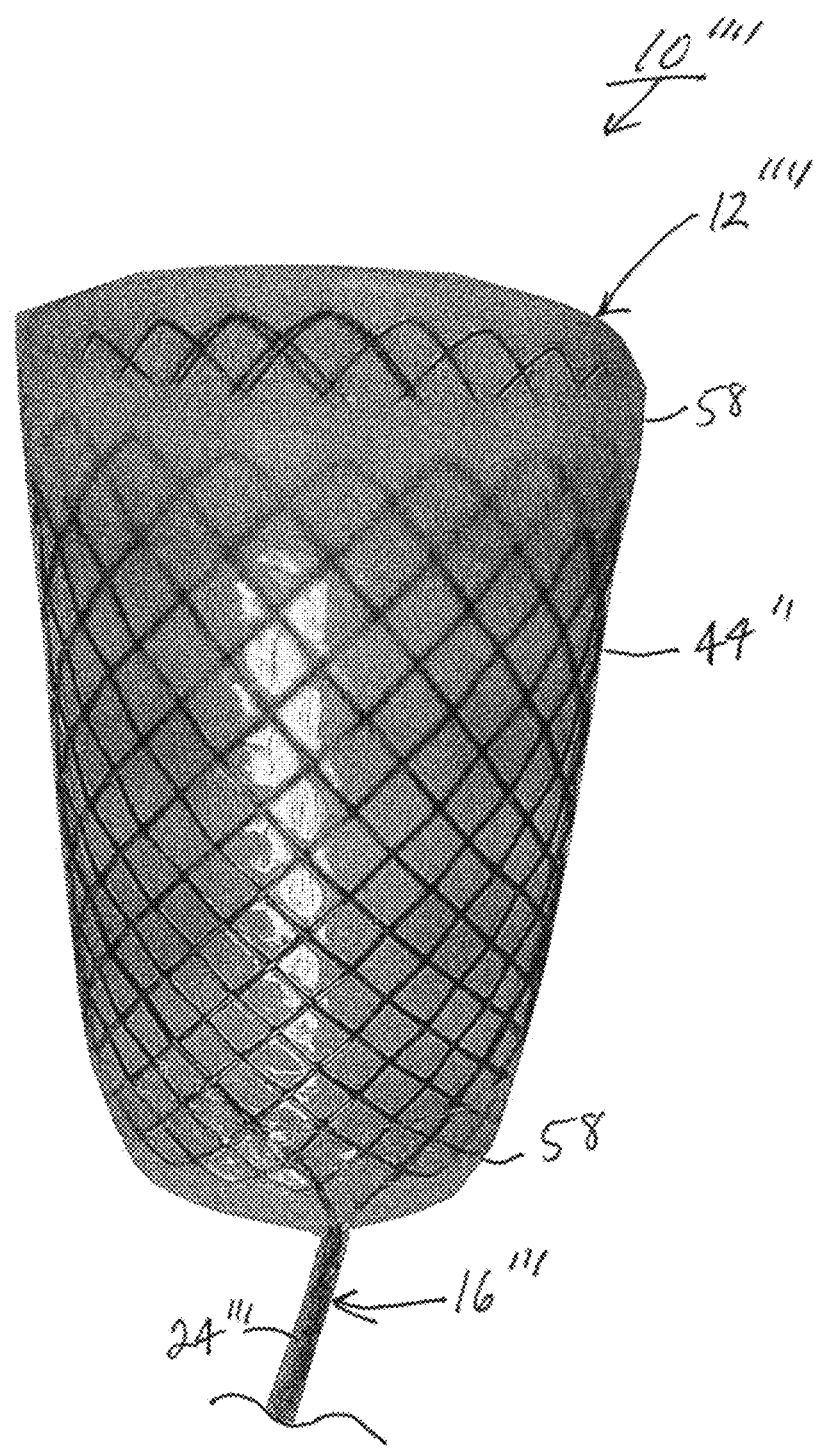
FIG. 69 is an enlarged perspective view of an esophageal member of another alternative embodiment of a bariatric device.
Figure 70:
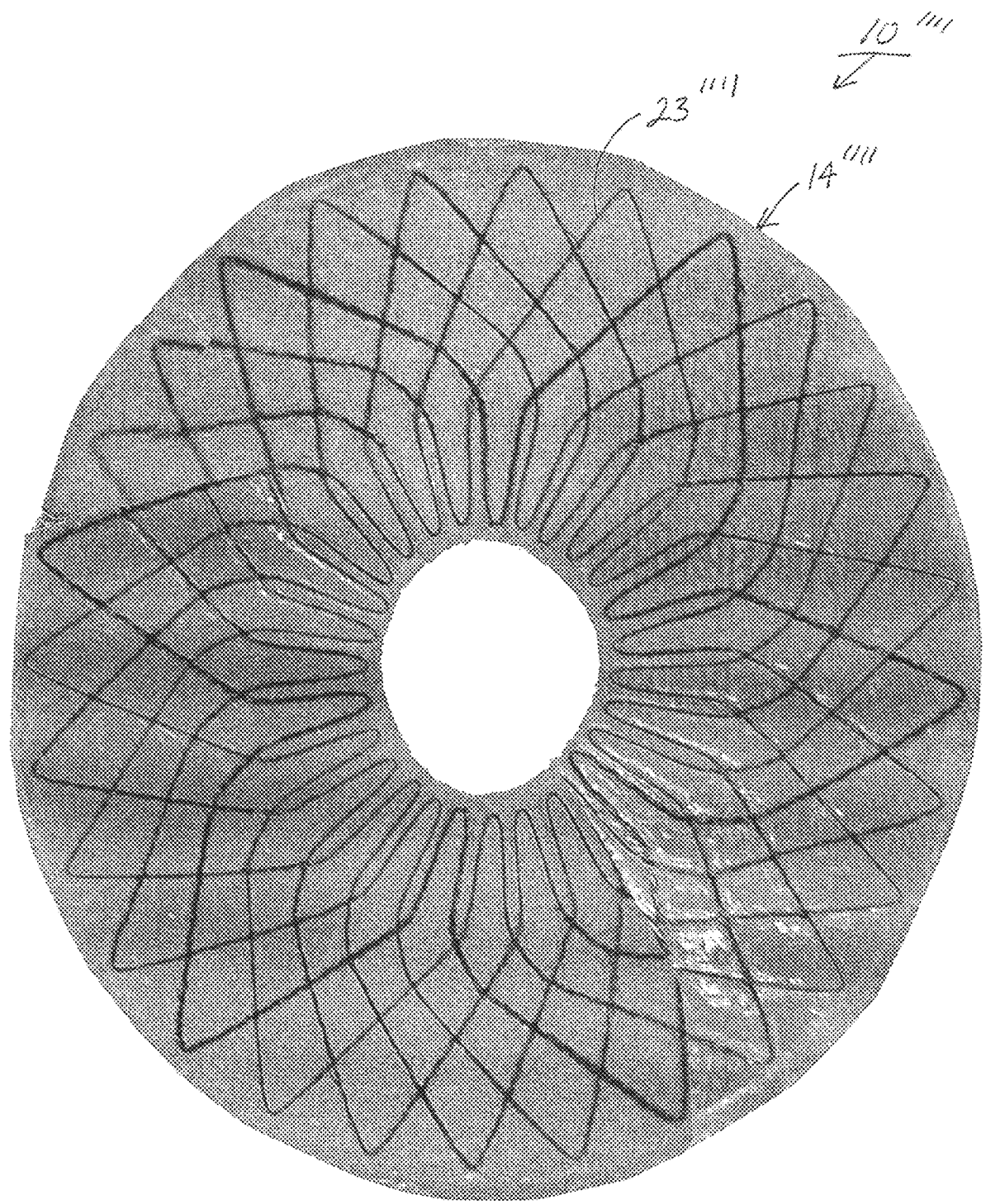
FIG. 70 is an enlarged perspective view of the cardiac member of the bariatric device of FIG. 69.

An alternative bariatric device 10'''' includes an esophageal member 12'''' and cardiac member 14'''' (FIGS. 69 and 70). Esophageal member 12'''' is similar to esophageal member 12''' except that it includes a cover 58 distally as well as one proximally. Cardiac member 14'''' is similar to cardiac member 14''' except that it includes a mesh 23'''' of different weave from mesh 23'''. In the illustrative embodiment, esophageal member 12'''' has a length of 35 mm, a proximal diameter of 25 mm and a distal diameter of 20 mm. It includes a connector 16''' with a tension member 24''' having a length of 17 mm.

Figure 71:
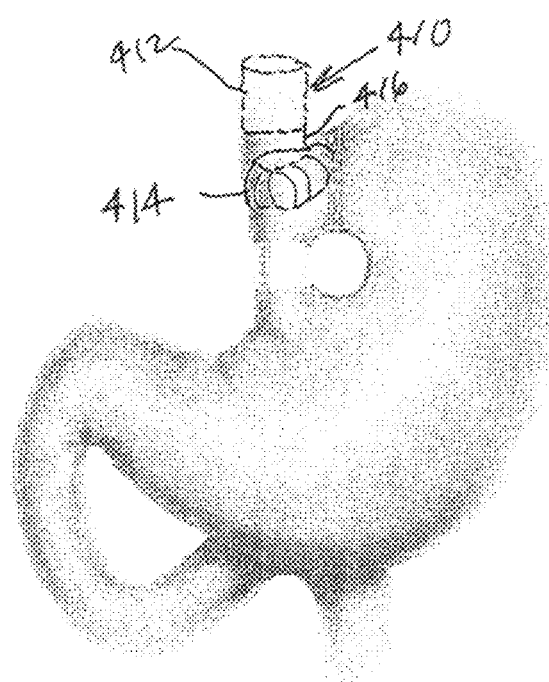
FIG. 71 is a perspective view illustrating deployment of another alternative embodiment of a bariatric device deployed in a recipient that underwent a vertical banded gastroplasty.
Figure 72:
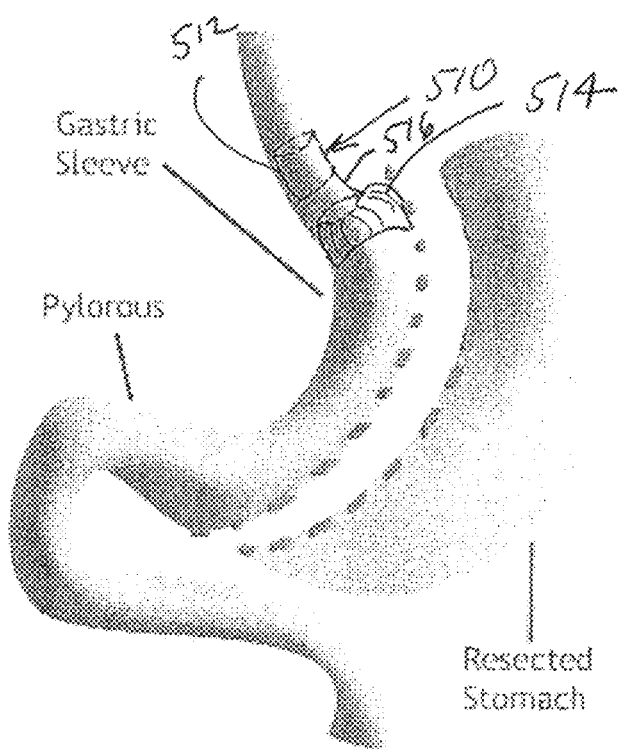
FIG. 72 is a perspective view illustrating deployment of another alternative embodiment of a bariatric device deployed in a recipient that underwent a sleeve gastrorectomy.
Figure 73:
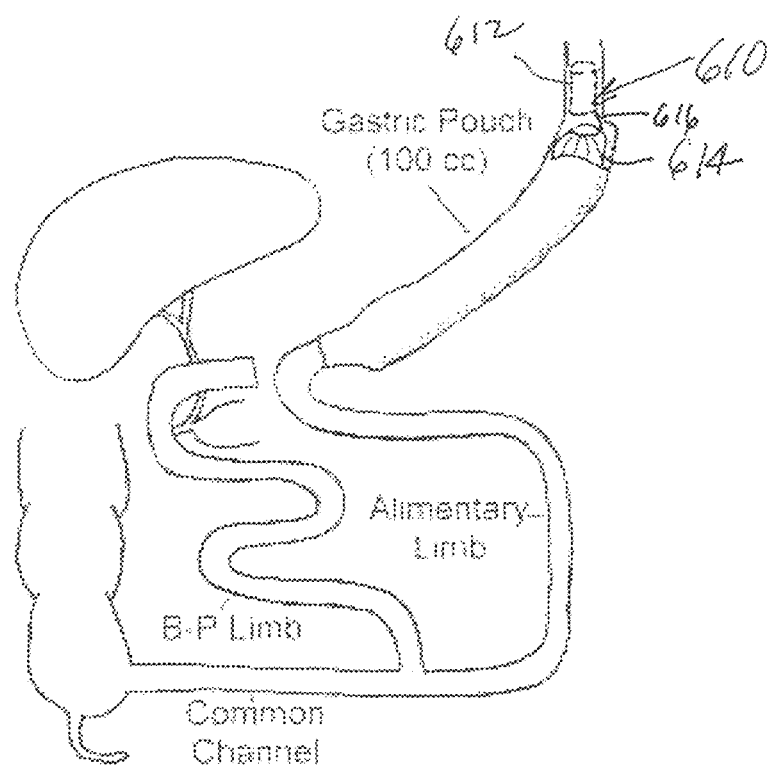
FIG. 73 is a perspective view illustrating deployment of another alternative embodiment of a bariatric device deployed in a recipient that underwent a duodenal switch.
Figure 74:
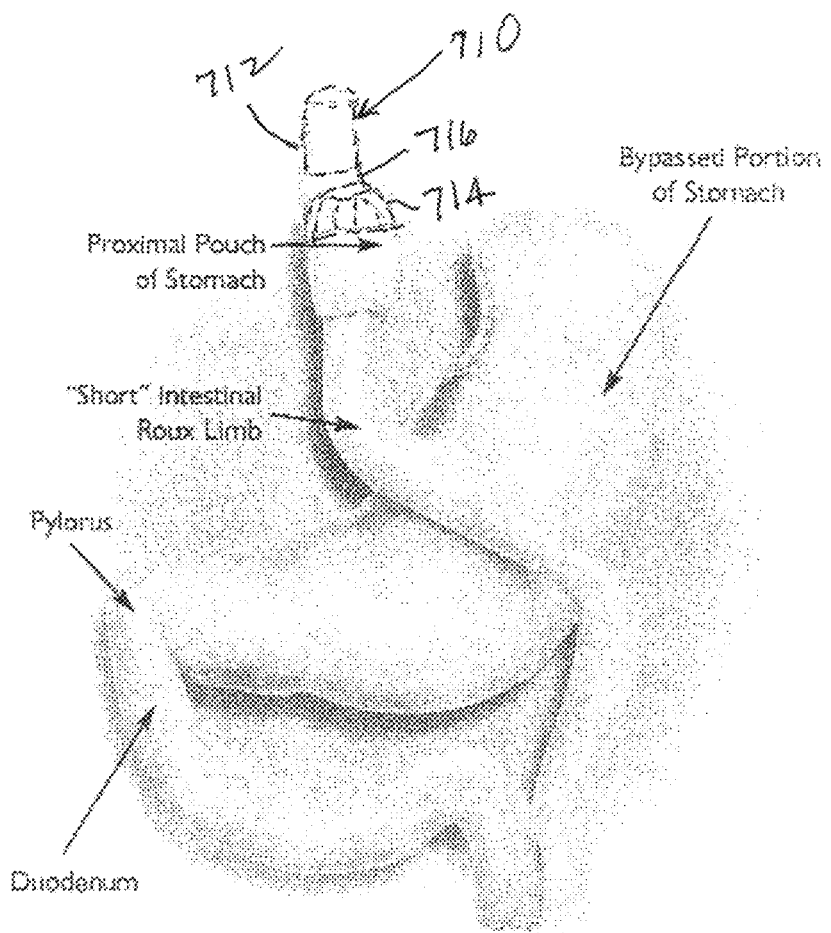
FIG. 74 is a perspective view illustrating deployment of another alternative embodiment of a bariatric device deployed in a recipient that underwent a gastric bypass procedure.

While previously described bariatric devices are illustrated as deployed in a recipient of unaltered anatomy, a modified form of such bariatric devices could perform the same function in a stomach that has been altered by surgery, such as bariatric surgery. Thus, the size and shape of the cardiac member, in particular, would be modified to the configuration of the stomach component of the altered anatomy to provide a tension, such as an outward pressure, similar to the bariatric device used with an unaltered anatomy. For example, a bariatric device 410 is shown having an esophageal member 412 having a wall configured to the size and shape of a portion of the esophagus connected by a connector 416 with a cardiac member 414 having a wall configured to the size and shape of the cardiac region of a stomach that has undergone vertical banded gastroplasty (FIG. 71). A bariatric device 510 is shown having an esophageal member 512 having a wall configured to the size and shape of a portion of the esophagus connected by a connector 516 with a cardiac member 514 having a wall configured to the size and shape of the cardiac region of a stomach that has undergone a sleeve gastrectomy (FIG. 72). A bariatric device 610 is shown having an esophageal member 612 having a wall configured to the size and shape of a portion of the esophagus connected by a connector 616 with a cardiac member 614 having a wall configured to the size and shape of the cardiac region of a stomach that has undergone a duodenal switch (FIG. 73). A bariatric device 710 is shown having an esophageal member 712 having a wall configured to the size and shape of a portion of the esophagus connected by a connector 716 with a cardiac member 714 having a wall configured to generally conform to the size and shape of the cardiac region of the proximal pouch of a recipient that has undergone a gastric bypass procedure, also known as a roux-en-y procedure (FIG. 74). Other examples will become apparent to the skilled practitioner. Previously described tethers may be deployed as part of connectors 416, 516, 616 and 716.

The bariatric devices disclosed herein may be made in whole or in part from bioabsorbable materials or from non-absorbable materials.

The strain exerted by the bariatric device influences the neurohormonal feedback mechanism present at the esophagus and/or stomach to cause weight loss. The strain that influences the neurohormonal feedback mechanism present at the abdominal portion of the esophagus, the esophageal-gastric junction and/or the cardiac portion of the stomach is intended to be relatively consistent over as large an area as reasonably possible. In contrast to prior proposed devices, such as restriction devices, which require that the recipient ingest food in order to influence neurohormonal feedback mechanisms, the embodiments of the bariatric device disclosed herein are effective in the absence of food. It also augments fullness caused by food.

The tissue attachment, tissue ingrowth and/or mucosal capture, which results from the tissue essentially at least partially incorporating certain embodiments of the bariatric device into the anatomy of the recipient, may provide resistance to the formation of microbial biofilm and thereby reduces the potential for infection, odor, and the like. As with all fixation techniques described herein, these may be used in combination with other fixation techniques. These anchoring techniques may be used to promote long-term deployment by incorporating the device into the body of the recipient.

Although various embodiments are illustrated herein, it should be understood that the features disclosed in each embodiment may be combined as would be apparent to the skilled artisan. In addition to influencing a neurohormonal feedback mechanism of the recipient to cause weight loss, the bariatric devices embodied herein may be capable of being anchored to the recipient and being retained in place for an extended period of time. Moreover, the various embodiments of the bariatric device, once deployed, are of a size and shape that would resist entering the pylorus should the bariatric device distally migrate outside of the esophagus into the stomach or are sufficiently small to pass through the intestines. This reduces the risk to the recipient. The recipient would likely be aware of the distal migration of the device because the recipient would, once again, experience increased hunger as a result of a reduction in satiety and/or metabolism. The physician could then insert an overtube in the recipient and reposition the bariatric device as previously described. Thus, it is unlikely that the bariatric device would migrate without notice and, would unlikely harm the recipient should the device migrate.

The embodiments of a bariatric device disclosed herein can be used for weight control in animals as well as humans. It can be used for weight control in children and adolescents as well as adults. It can be used with overweight and mildly obese recipients as well as with morbidly obese recipients.

Thus, it is seen that the disclosed embodiment provides a new category of weight loss techniques. The embodiment advantageously utilizes mechanoreceptors, such as tension receptors, stretch receptors and/or baroreceptors, such as those located at the abdominal portion of the esophagus and/or esophageal-gastric junction and/or the cardiac portion of the stomach of the recipient to cause weight loss. The disclosed embodiments provide a non-invasive or minimally invasive technique. The disclosed embodiments facilitate burping and vomiting and do not substantially interfere with other functions of the GE junction pseudo-sphincter.

Changes and modifications in the specifically described embodiments can be carried out without departing from the principles of the invention which is intended to be limited only by the scope of the appended claims, as interpreted according to the principles of patent law including the doctrine of equivalents.

The embodiments of the invention in which an exclusive property or privilege is claimed are defined as follows:

1. A method of deploying a bariatric device in a recipient having an esophagus and a stomach, the bariatric device having an esophageal member that is configured to generally conform to the shape and size of a portion of the esophagus, a cardiac member that is configured to generally conform to the shape and size of a cardiac portion of the stomach, and a connector connected with the esophageal member and the cardiac member, said method comprising:
    guiding a distal end portion of a deployment device to the stomach, wherein at least a portion of the bariatric device is disposed at the distal end portion;
    at least partially deploying the bariatric device including the cardiac member from the deployment device in the stomach;
    positioning the cardiac member of the bariatric device against the cardiac portion of the stomach by proximately withdrawing the deployment device to pull the cardiac member against the cardiac portion of the stomach; and
    further deploying the bariatric device from the deployment device in the esophagus.

2. The method as claimed in claim 1, including guiding the deployment device transorally into the stomach via a guide wire.

3. The method as claimed in claim 1, wherein the deployment device comprises a tubular member having a cross section configured to be smaller than the recipient's esophagus.

4. The method as claimed in claim 3, wherein, prior to guiding the deployment device to the stomach, the bariatric device is compressed within the tubular member of the deployment device.

5. The method as claimed in claim 4, wherein deploying the bariatric device in the stomach includes unfurling the cardiac member from the tubular member.

6. The method as claimed in claim 4, wherein the cardiac member unfolds from a compressed state to an expanded state when the cardiac member is clear from the distal end portion of the tubular member.

7. The method as claimed in claim 3, wherein the further deploying the bariatric device includes unfurling the esophageal member from the tubular member.

8. The method as claimed in claim 1, wherein the bariatric device is at least partially deployed from the distal end portion of the deployment device in the stomach utilizing a pusher inserted within the deployment device.

9. The method as claimed in claim 1, further including deploying the esophageal member in the esophagus.

10. The method as claimed in claim 1, wherein after deploying the cardiac member in the stomach, the deployment device is withdrawn proximally to position the cardiac member against the cardiac portion of the stomach.

11. The method as claimed in claim 1, wherein the deployment device is withdrawn proximally to deploy the esophageal member from the deployment device.

12. The method as claimed in claim 1, wherein prior to deploying the esophageal member, the cardiac member is oriented in the stomach by rotating the deployment device.

13. The method as claimed in claim 12, wherein the cardiac member is oriented in the stomach by visualizing a marker on the deployment device.

14. The method as claimed in claim 12, wherein the cardiac member is oriented in the stomach utilizing fluoroscopy.

15. The method as claimed in claim 1 including anchoring the bariatric device to the recipient after deploying the bariatric device.

16. The method as claimed in claim 15, wherein the recipient includes a gastro-esophageal junction pseudo-sphincter between the esophagus and the stomach and wherein said anchoring comprises passing at least one tether through the esophageal member, outside of the gastro-esophageal junction pseudo-sphincter through the walls of the esophagus and stomach and through the cardiac member.

17. The method as claimed in claim 15, wherein said anchoring comprises growing tissue in openings in the bariatric device.

18. A method of deploying a bariatric device in a recipient having an esophagus and a stomach, the bariatric device having an esophageal member that is configured to generally conform to the shape and size of a portion of the esophagus, a cardiac member that is configured to generally conform to the shape and size of a cardiac portion of the stomach, and a connector connected with the esophageal member and the cardiac member, said method comprising:
    guiding a distal end portion of a deployment device to the stomach, wherein at least a portion of the bariatric device is disposed at the distal end portion;
    at least partially deploying the bariatric device including the cardiac member from the deployment device in the stomach;
    positioning the cardiac member of the bariatric device against the cardiac portion of the stomach; and
    further deploying the bariatric device from the deployment device in the esophagus, wherein the deployment device comprises a tubular member and wherein the bariatric device is folded into the tubular member with the cardiac member rolled and the esophageal member radially compressed.

19. A method of deploying a bariatric device in a recipient having an esophagus and a stomach, the bariatric device having an esophageal member that is configured to generally conform to the shape and size of a portion of the esophagus, a cardiac member that is configured to generally conform to the shape and size of a cardiac portion of the stomach, and a connector connected with the esophageal member and the cardiac member, said method comprising:

guiding a distal end portion of a deployment device to the stomach, wherein at least a portion of the bariatric device is disposed at the distal end portion;

at least partially deploying the bariatric device including the cardiac member from the deployment device in the stomach;

positioning the cardiac member of the bariatric device against the cardiac portion of the stomach;

further deploying the bariatric device from the deployment device in the esophagus; and causing strain to be applied by the cardiac member to the cardiac portion of the stomach in the absence of food, including anchoring the esophageal member to the esophagus of the recipient to resist distal migration of the esophageal member with respect to the esophagus, wherein the connector transmits force between the esophageal member and the cardiac member.

20. A method of deploying a bariatric device in a recipient having an esophagus and a stomach, the bariatric device having an esophageal member that is configured to generally conform to the shape and size of a portion of the esophagus, a cardiac member that is configured to generally conform to the shape and size of a cardiac portion of the stomach, and a connector connected with the esophageal member and the cardiac member, said method comprising:

guiding a distal end portion of a deployment device to the stomach, wherein at least a portion of the bariatric device is disposed at the distal end portion;

at least partially deploying the bariatric device including the cardiac member from the deployment device in the stomach;

positioning the cardiac member of the bariatric device against the cardiac portion of the stomach;

further deploying the bariatric device from the deployment device in the esophagus; and positioning the cardiac member with respect to the cardiac portion of the stomach with at least one line extending outside of the recipient from the bariatric device, wherein at least one line comprises suture material.

21. The method as claimed in claim 20, including removing at least one line after said positioning.

22. A method of deploying a bariatric device in a recipient having an esophagus and a stomach, the bariatric device having an esophageal member that is configured to generally conform to the shape and size of a portion of the esophagus, a cardiac member that is configured to generally conform to the shape and size of a cardiac portion of the stomach, and a connector connected with the esophageal member and the cardiac member, said method comprising:

guiding a distal end portion of a deployment device to the stomach, wherein at least a portion of the bariatric device is disposed at the distal end portion;

at least partially deploying the bariatric device including the cardiac member from the deployment device in the stomach;

positioning the cardiac member of the bariatric device against the cardiac portion of the stomach;

further deploying the bariatric device from the deployment device in the esophagus; and positioning the cardiac member with respect to the cardiac portion of the stomach with at least one line extending outside of the recipient from the bariatric device, wherein said at least one line is attached to the esophageal member and is used to snug the cardiac member against the cardiac portion of the stomach.

23. A method of deploying a bariatric device in a recipient having an esophagus and a stomach, the bariatric device having an esophageal member that is configured to generally conform to the shape and size of a portion of the esophagus, a cardiac member that is configured to generally conform to the shape and size of a cardiac portion of the stomach, and a connector connected with the esophageal member and the cardiac member, said method comprising:

guiding a distal end portion of a deployment device to the stomach, wherein at least a portion of the bariatric device is disposed at the distal end portion;

at least partially deploying the bariatric device including the cardiac member from the deployment device in the stomach;

positioning the cardiac member of the bariatric device against the cardiac portion of the stomach;

further deploying the bariatric device from the deployment device in the esophagus; and positioning the cardiac member with respect to the cardiac portion of the stomach with at least one line extending outside of the recipient from the bariatric device, wherein said at least one line is attached to cardiac member and is used to laterally adjust the cardiac member.

* * * * *